US011278292B2

(12) United States Patent
Gorochow et al.

(10) Patent No.: US 11,278,292 B2
(45) Date of Patent: Mar. 22, 2022

(54) INVERTING BRAIDED ANEURYSM TREATMENT SYSTEM AND METHOD

(71) Applicant: DePuy Synthes Products, Inc., Raynham, MA (US)

(72) Inventors: Lacey Gorochow, Raynham, MA (US); Ruijiao Xu, Miami Lakes, FL (US); Shawn Kallivayalil, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 17/071,565

(22) Filed: Oct. 15, 2020

(65) Prior Publication Data
US 2021/0085333 A1    Mar. 25, 2021

Related U.S. Application Data

(63) Continuation-in-part of application No. 16/865,116, filed on May 1, 2020, and a continuation-in-part of
(Continued)

(51) Int. Cl.
*A61B 17/12* (2006.01)

(52) U.S. Cl.
CPC .. *A61B 17/12113* (2013.01); *A61B 17/12031* (2013.01); *A61B 17/12145* (2013.01); *A61B 2017/1205* (2013.01)

(58) Field of Classification Search
CPC ........ A61B 17/12113; A61B 17/12031; A61B 17/12145; A61B 2017/1205;
(Continued)

(56) References Cited

U.S. PATENT DOCUMENTS 2,849,002 A   8/1958   Oddo
3,480,017 A   11/1969  Shute
(Continued)

FOREIGN PATENT DOCUMENTS

CA   2395796 A1   7/2001
CA   2 431 594 A1   9/2002
(Continued)

OTHER PUBLICATIONS

Extended European Search Report issued in corresponding European Patent Application No. 20 21 2968 dated May 11, 2021.
(Continued)

*Primary Examiner* — Wade Miles
*Assistant Examiner* — Mikail A Mannan
(74) *Attorney, Agent, or Firm* — Troutman Pepper Hamilton Sanders LLP

(57) ABSTRACT

An example system can include a tubular braid, a catheter, and an embolic coil. The tubular braid can have an open end, a pinched end, and a predetermined shape. In the predetermined shape, the tubular braid can have two inversions and a middle segment extending between the two inversions that forms a sack. The tubular braid can be implanted in an implanted shape based on the predetermined shape. A distal end of the catheter can be inserted into the sack when the tubular braid is implanted. The embolic coil can be delivered through the catheter into the sack. The opening to the sack can correspond to a constricted columnar segment of the middle segment when the braid is in the predetermined shape.

9 Claims, 55 Drawing Sheets

Related U.S. Application Data application No. 16/865,165, filed on May 1, 2020, said application No. 16/865,116 is a continuation-in-part of application No. 16/748,877, filed on Jan. 22, 2020, said application No. 16/865,165 is a continuation-in-part of application No. 16/748,877, filed on Jan. 22, 2020, said application No. 16/865,116 is a continuation-in-part of application No. 16/853,135, filed on Apr. 20, 2020, said application No. 16/865,165 is a continuation-in-part of application No. 16/853,135, filed on Apr. 20, 2020, said application No. 16/748,877 is a continuation-in-part of application No. 16/418,199, filed on May 21, 2019, now Pat. No. 10,653,425, said application No. 16/853,135 is a continuation-in-part of application No. 16/418,199, filed on May 21, 2019, now Pat. No. 10,653,425, application No. 17/071,565, which is a continuation-in-part of application No. 16/703,973, filed on Dec. 5, 2019.

(58) Field of Classification Search
CPC ........ A61B 17/12022; A61B 17/12109; A61B 17/1213; A61B 17/12168; A61B 17/12172
See application file for complete search history.

(56) References Cited

U.S. PATENT DOCUMENTS

| | | |
|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,891,128 A | 4/1999 | Gia et al. |
| 5,916,235 A | 6/1999 | Guglielmi |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |
| 8,454,633 B2 | 6/2013 | Amplatz et al. |
| 8,523,897 B2 | 9/2013 | van der Burg et al. |

(56) References Cited

U.S. PATENT DOCUMENTS

| | | |
|---|---|---|
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,992,568 B2 | 3/2015 | Duggal et al. |
| 8,998,947 B2 | 3/2015 | Aboytes et al. |
| 8,974,512 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Bowman |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Gutterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenaugh et al. |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287297 A1 | 11/2009 | Cox |
| 2009/0318911 A1 | 12/2009 | Sepetka |
| 2010/0023046 A1 | 1/2010 | Heidner et al. |
| 2010/0023048 A1* | 1/2010 | Mach ............... A61B 17/12177 606/200 |
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |

(56) References Cited

U.S. PATENT DOCUMENTS

| | | |
|---|---|---|
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1* | 10/2015 | Lorenzo ........... A61B 17/12145 606/200 |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0069313 A1 | 3/2020 | Xu et al. |
| 2020/0268365 A1 | 8/2020 | Hebert et al. |

FOREIGN PATENT DOCUMENTS

| | | |
|---|---|---|
| CA | 2598048 A1 | 5/2008 |
| CN | 204 683 687 U | 7/2015 |
| DE | 102008015781 A1 | 10/2009 |
| DE | 102010053111 A1 | 6/2012 |
| DE | 102009058132 B4 | 7/2014 |
| DE | 102013106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |

(56) References Cited

FOREIGN PATENT DOCUMENTS

| | | |
|---|---|---|
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2016-502925 A | 2/2015 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | WO 2005117718 A1 | 12/2005 |
| WO | WO 2006034149 A2 | 3/2006 |
| WO | WO 2006052322 A2 | 5/2006 |
| WO | 2007076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | 2015073704 A1 | 5/2015 |
| WO | WO 2015160721 A1 | 10/2015 |
| WO | WO 2015166013 A1 | 11/2015 |
| WO | WO 2015171268 A2 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2012/034135 A1 | 3/2021 |

OTHER PUBLICATIONS

Altes et al., Creation of Saccular Aneurysms in the Rabbit: A Model Suitable for Testing Endovascular Devices. AJR 2000; 174: 349-354.

Schaffer, Advanced Materials & Processes, Oct. 2002, pp. 51-54.

* cited by examiner

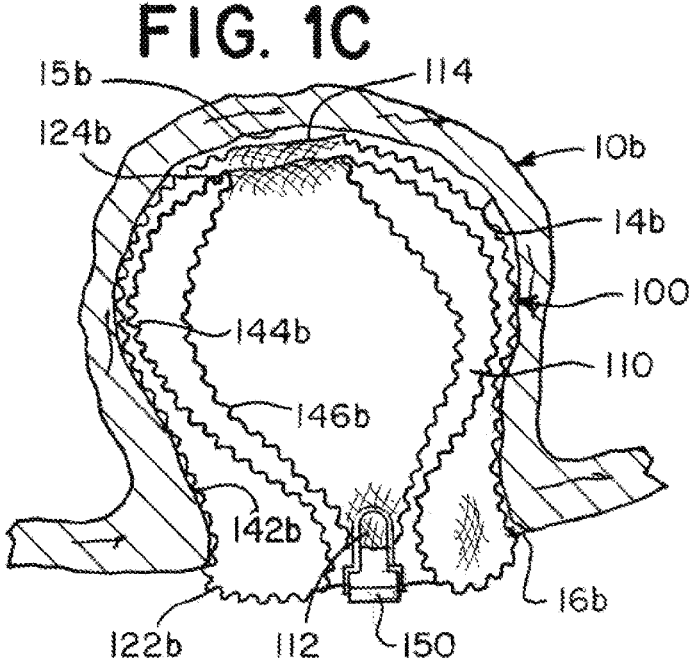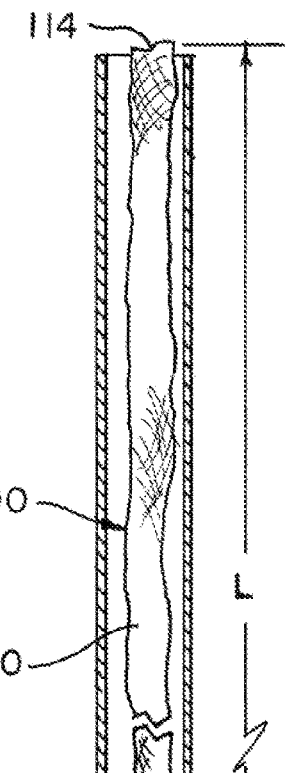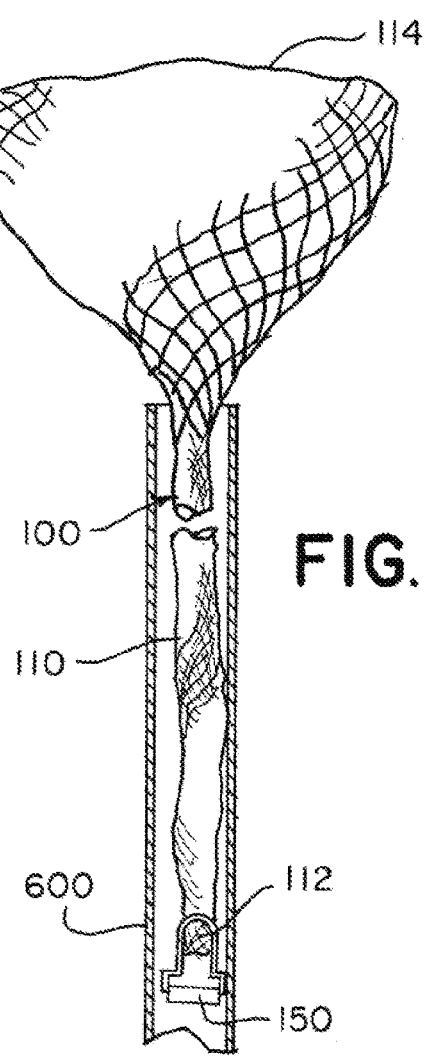

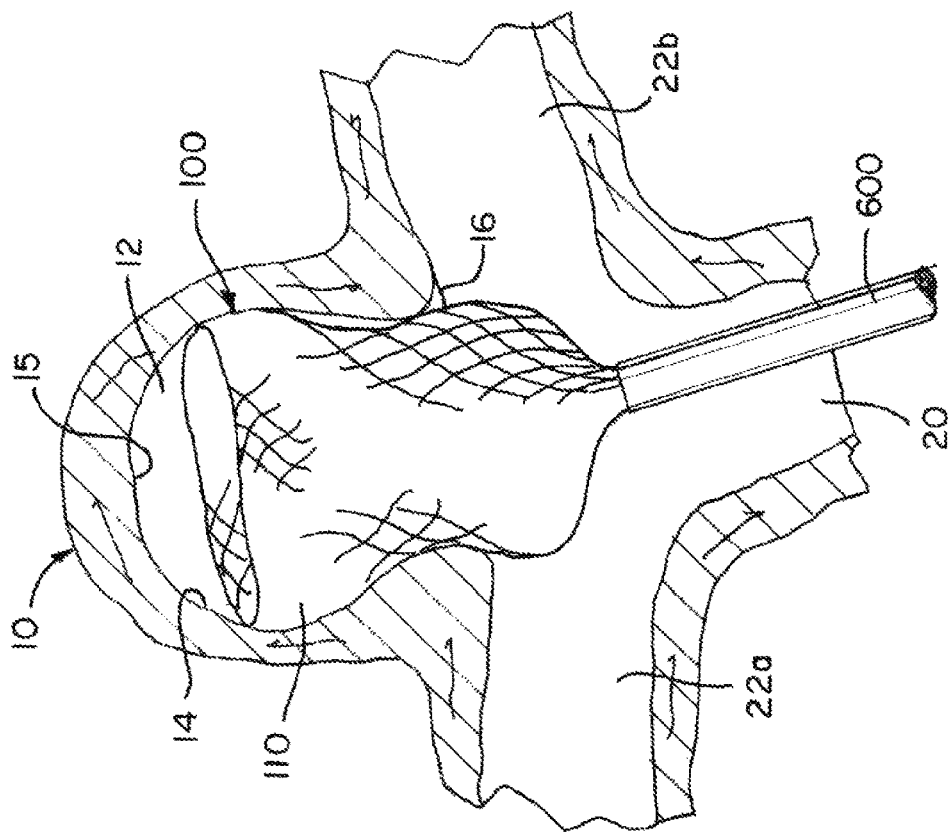
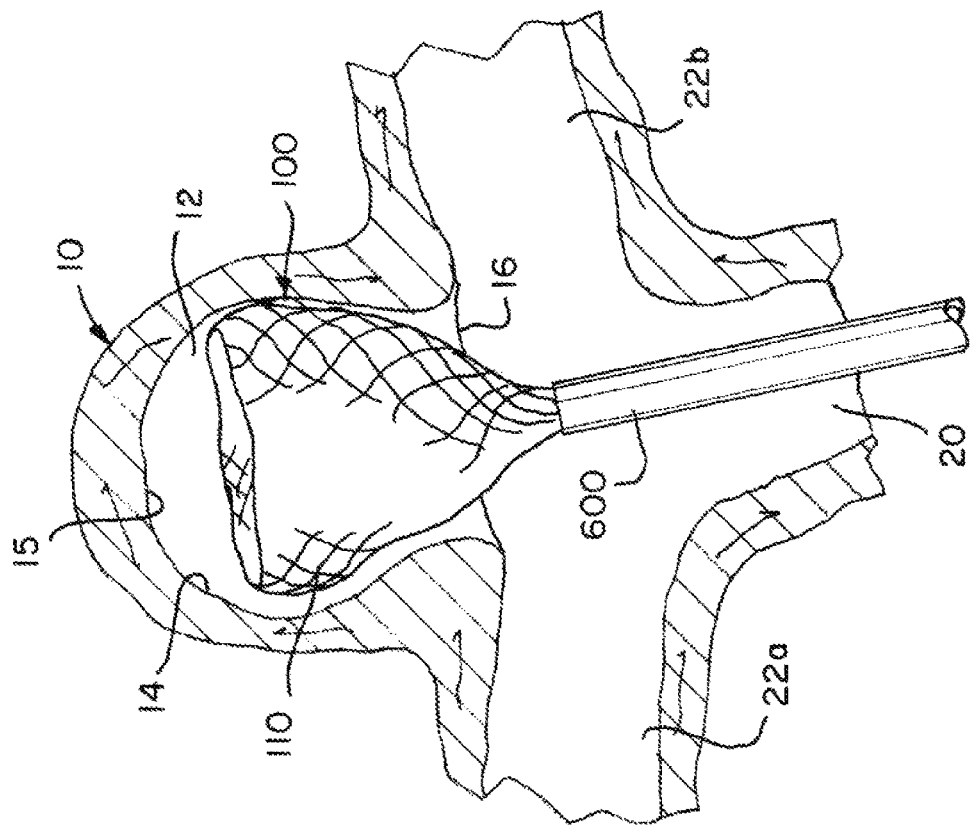

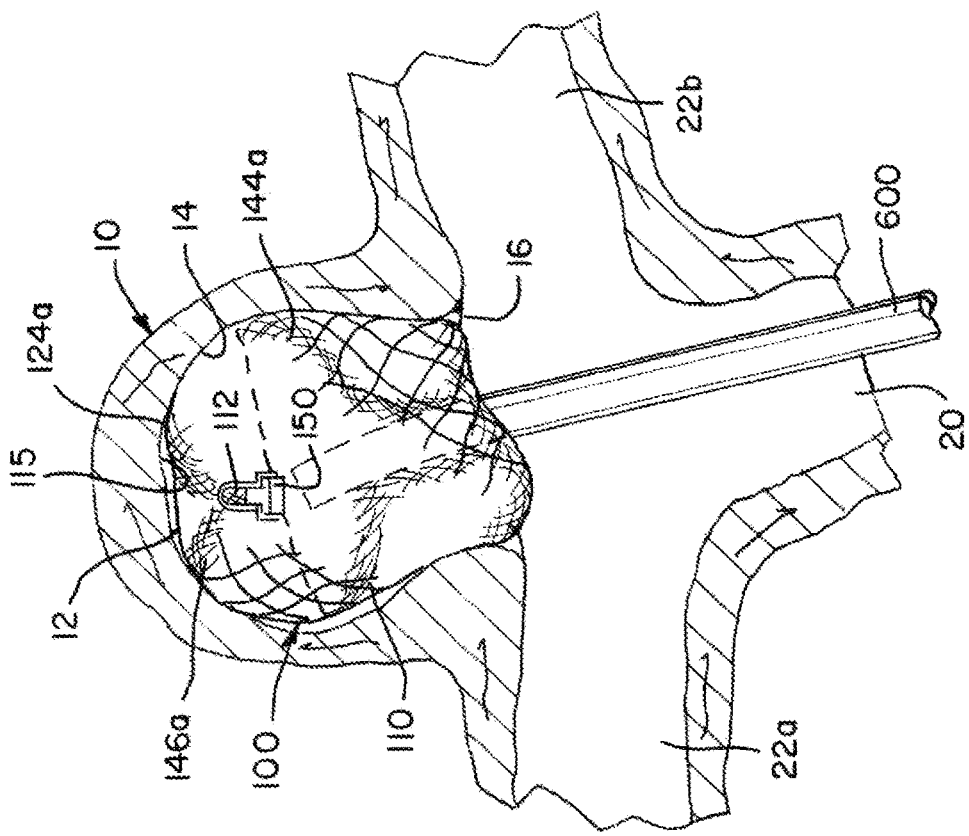
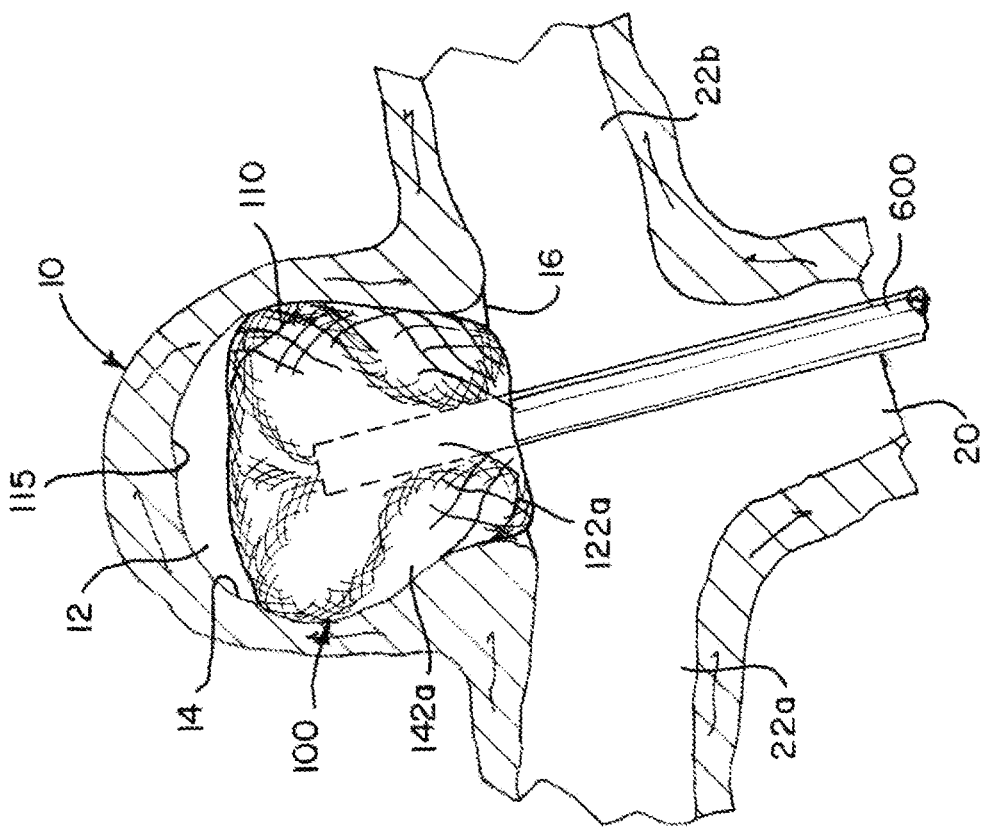

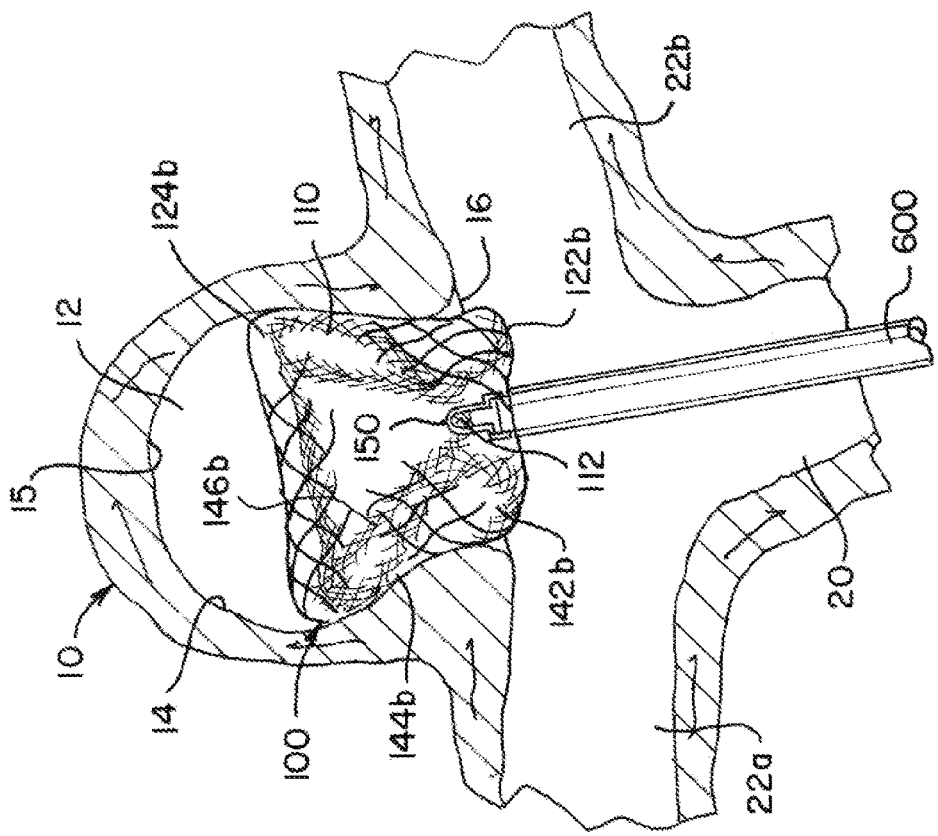
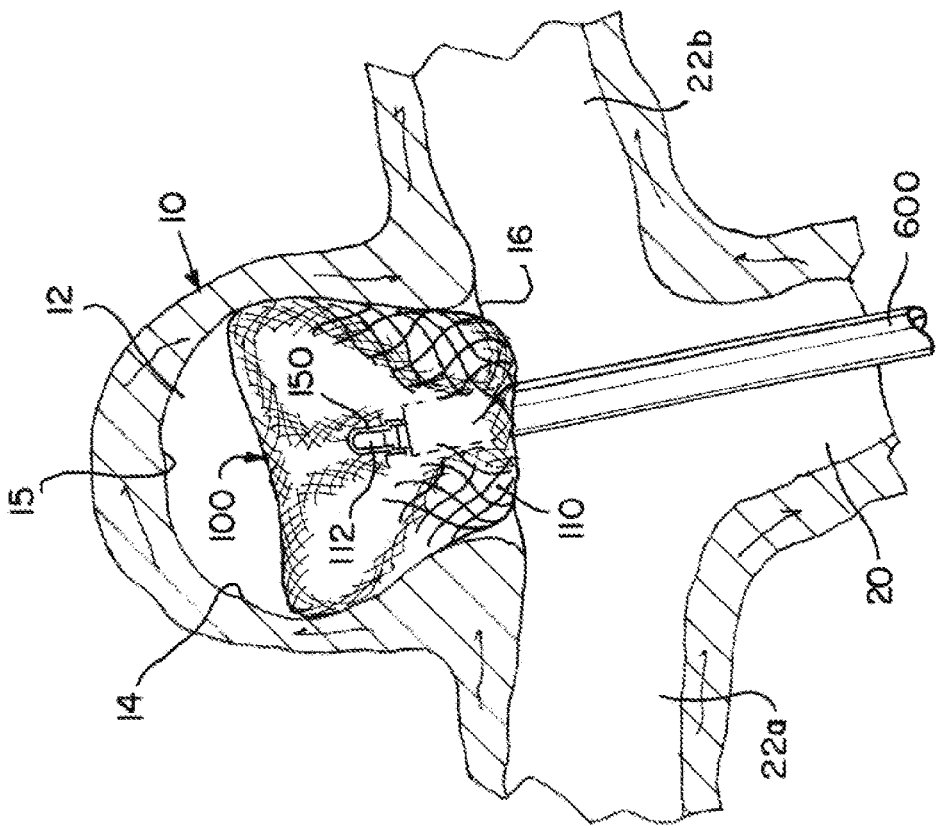

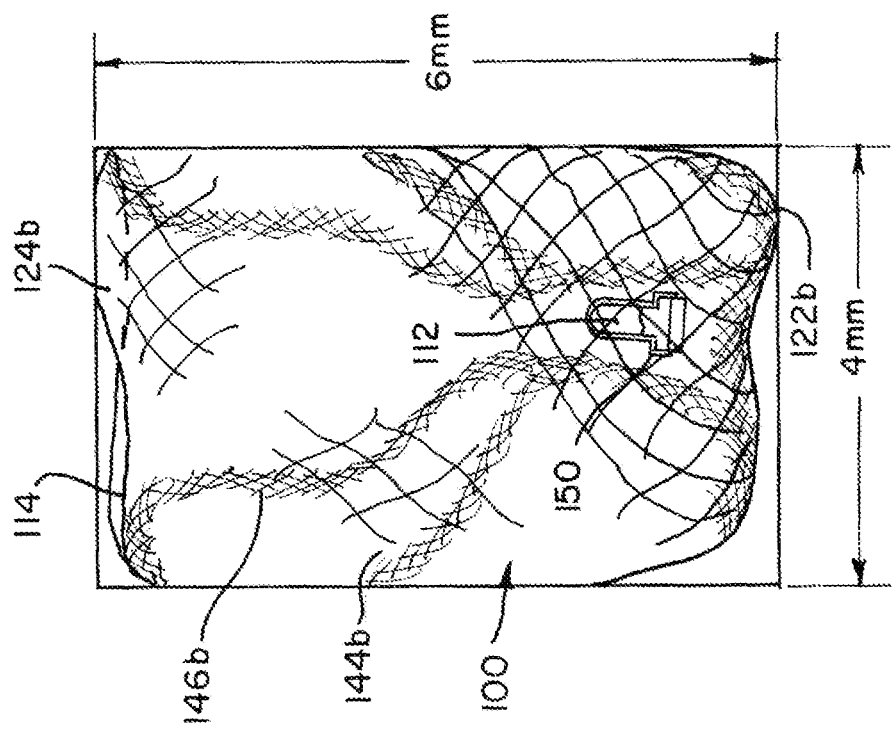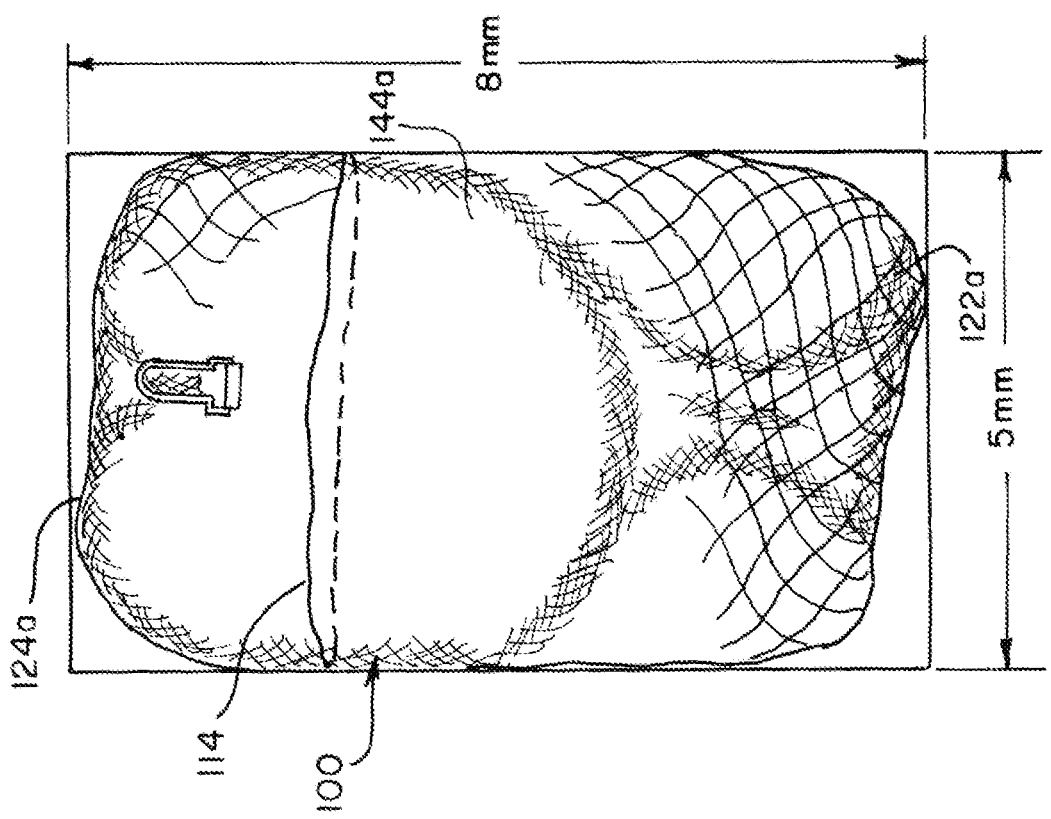

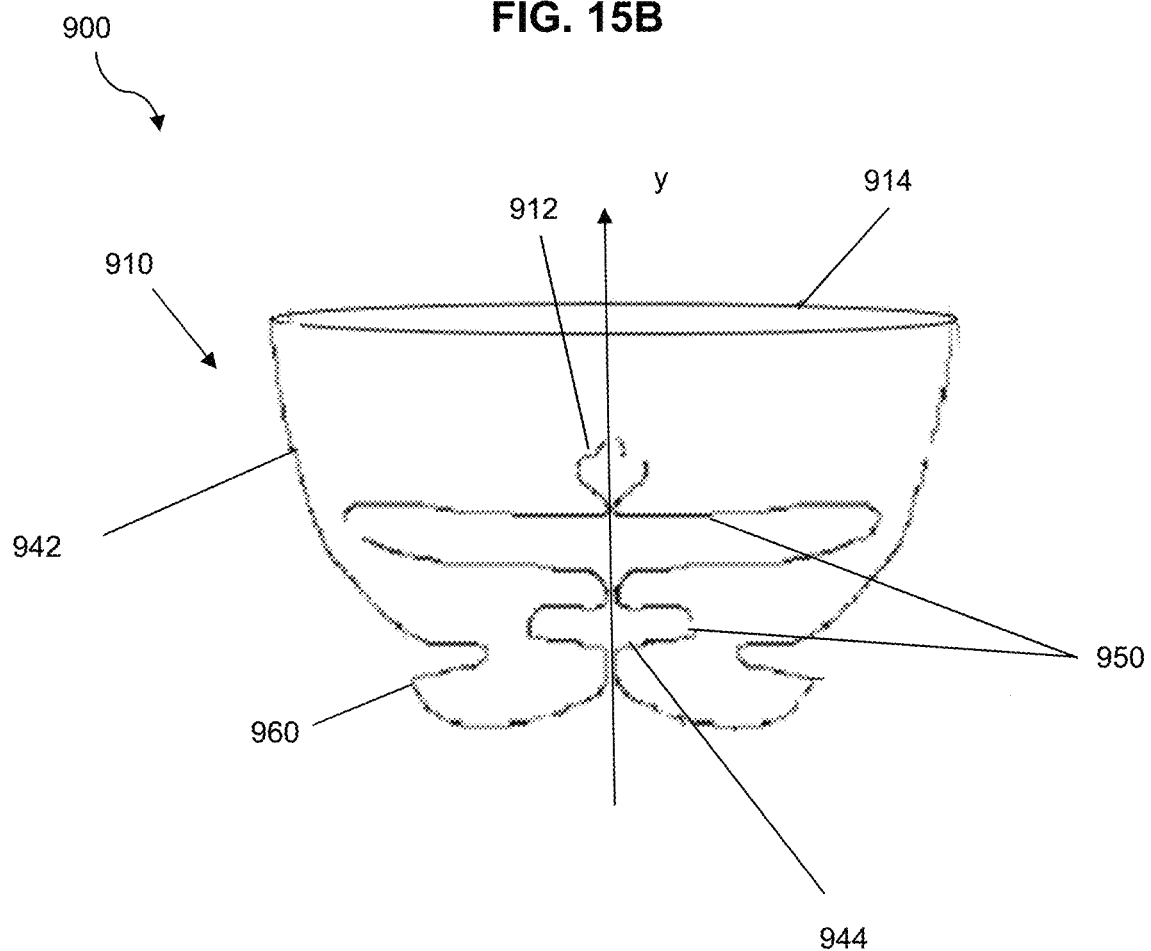

FIG. 18A
FIG. 18B
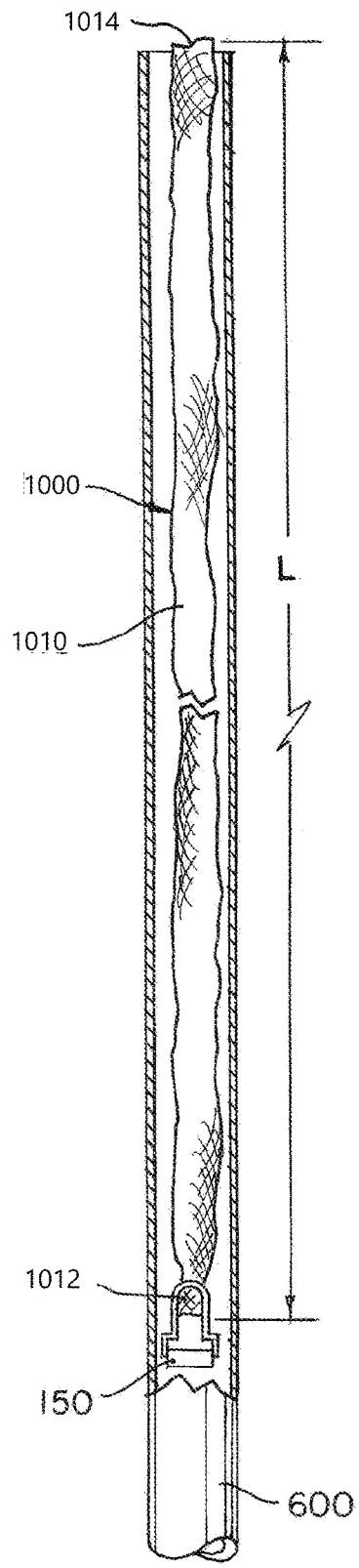
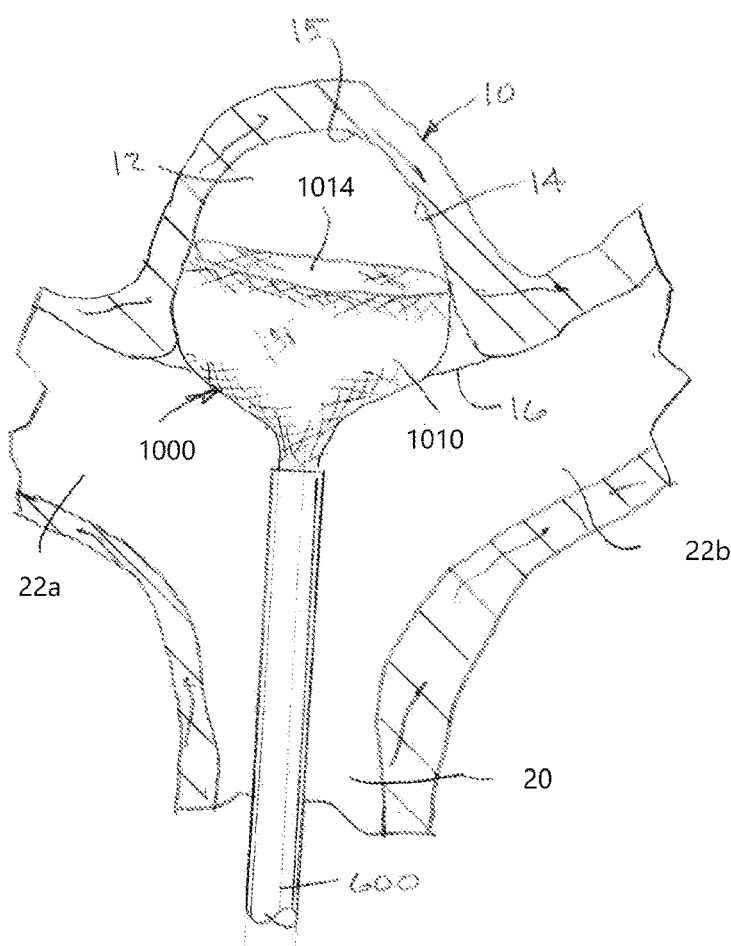

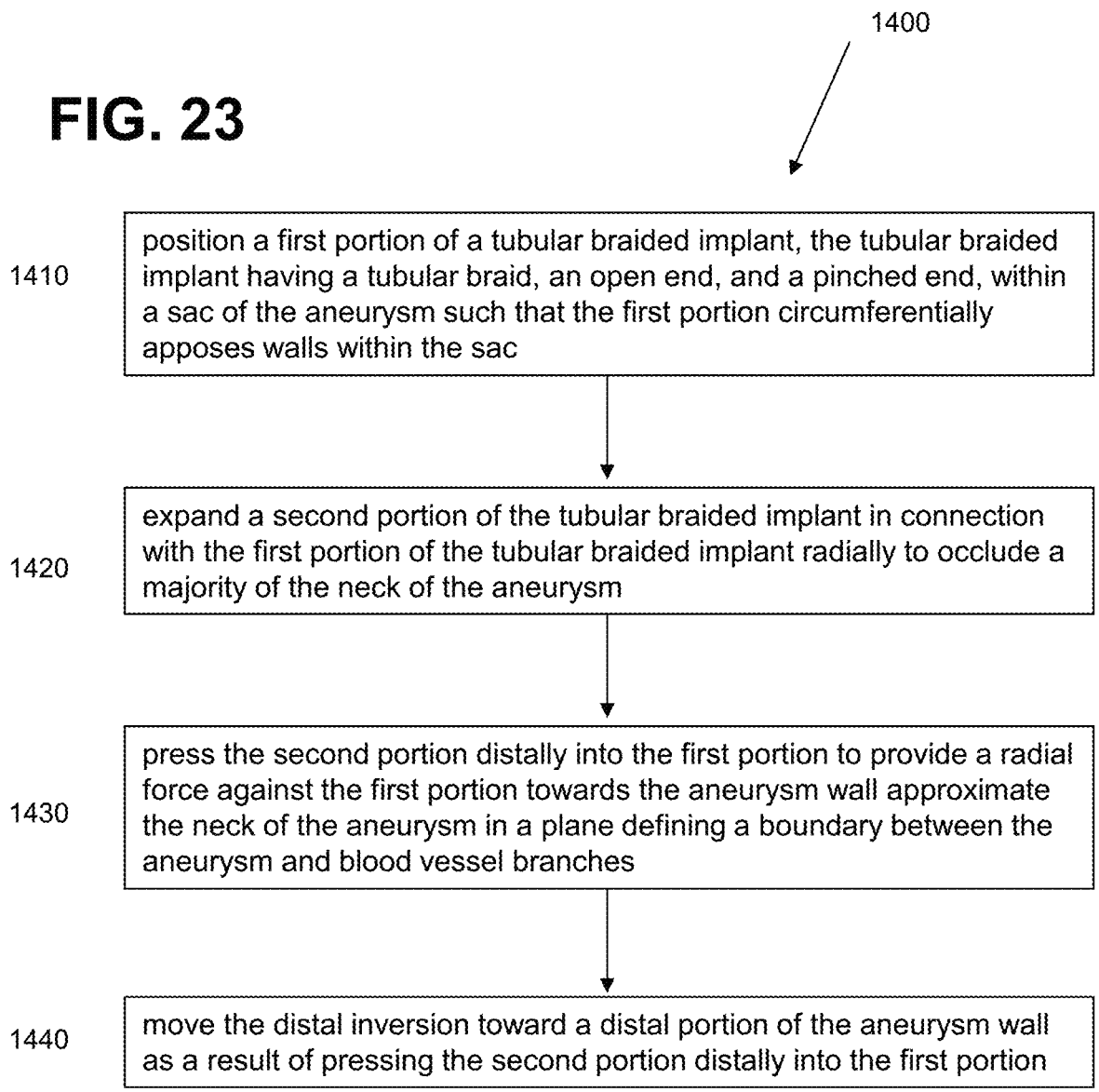

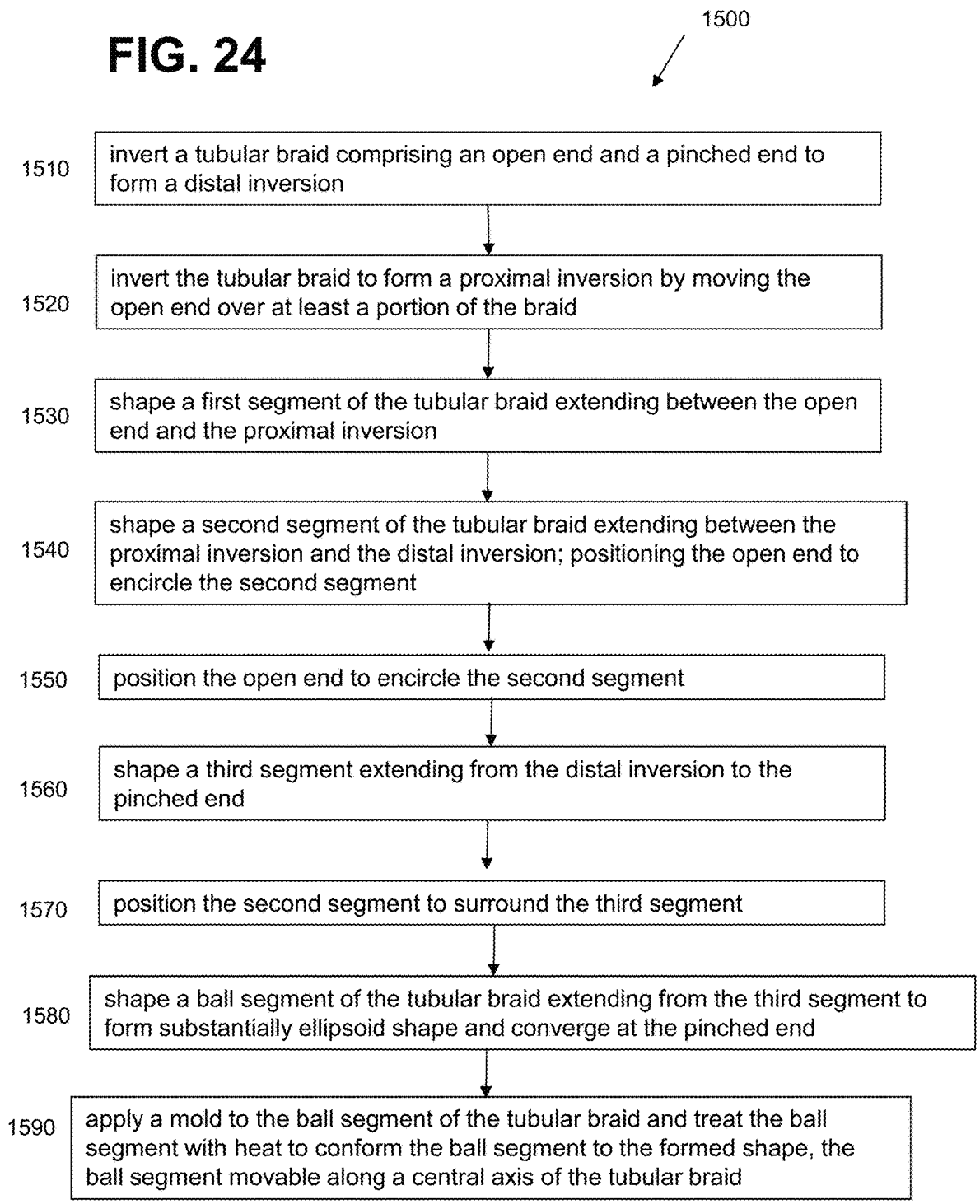

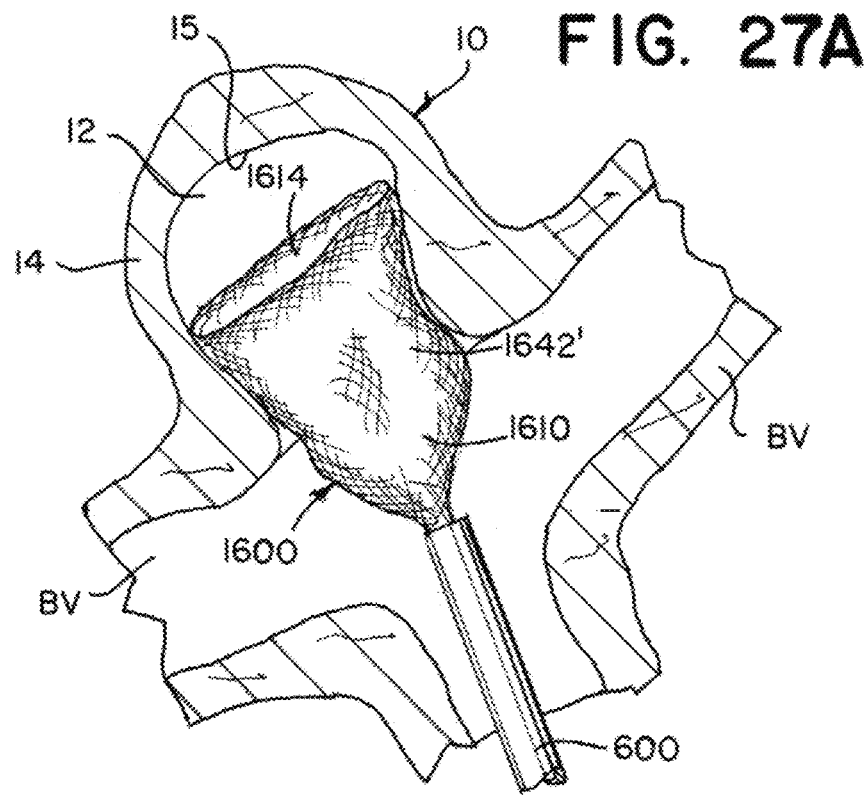
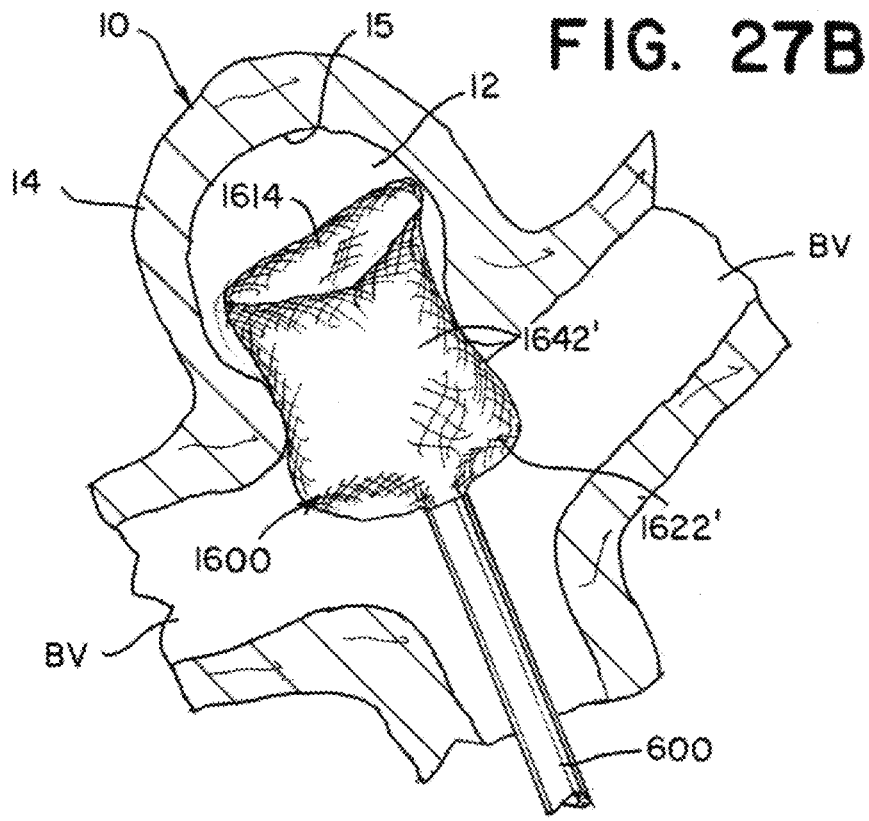

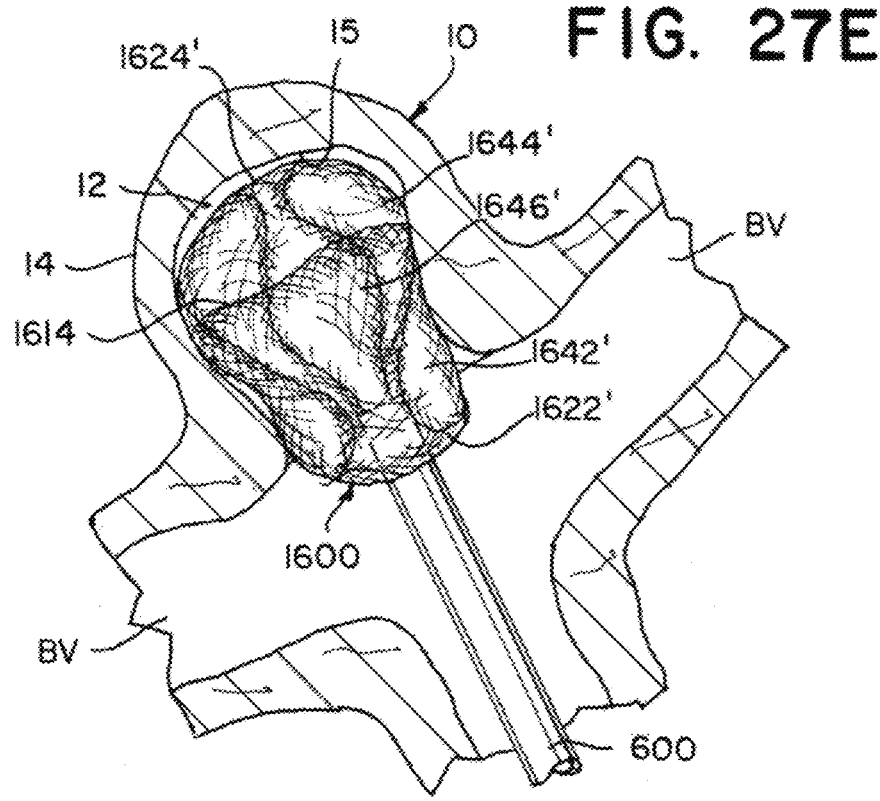
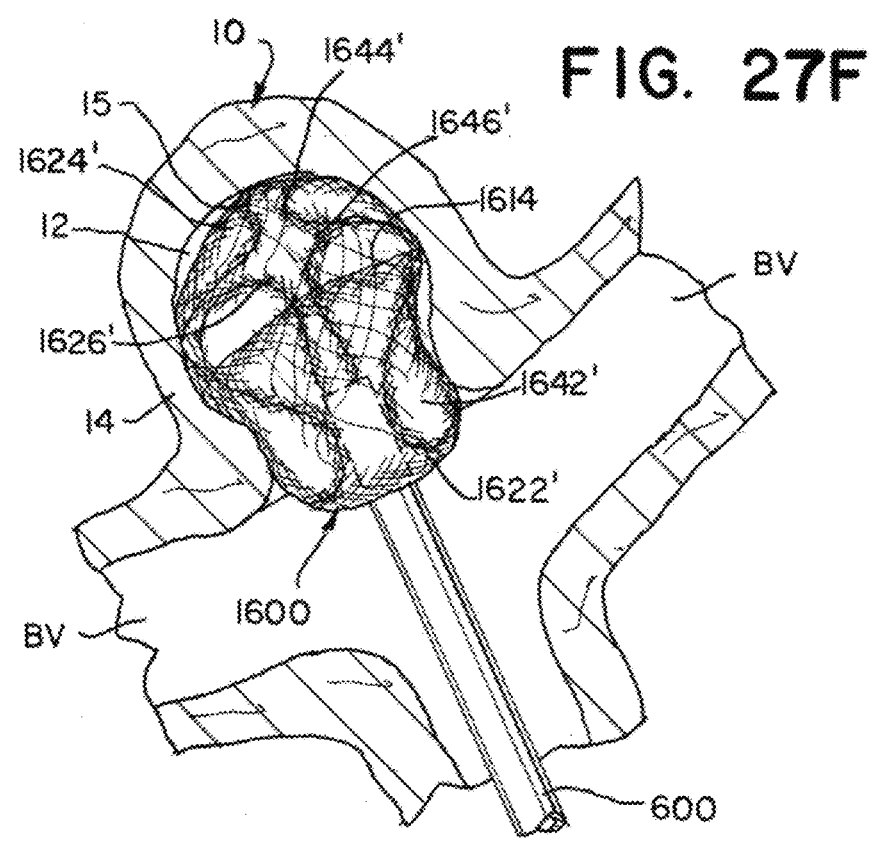

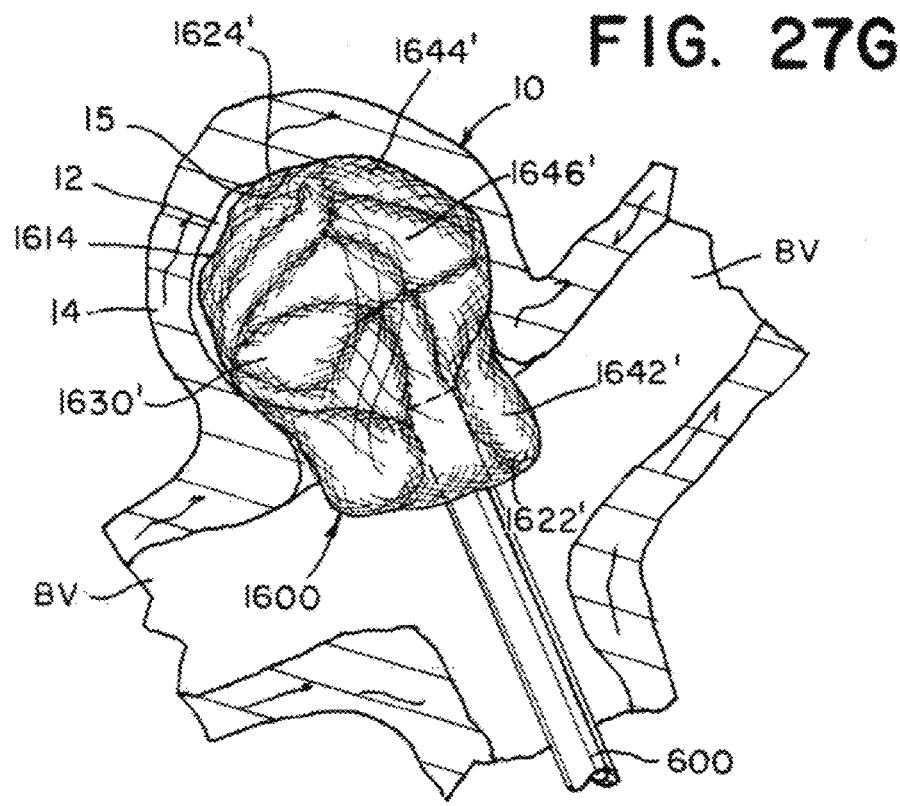
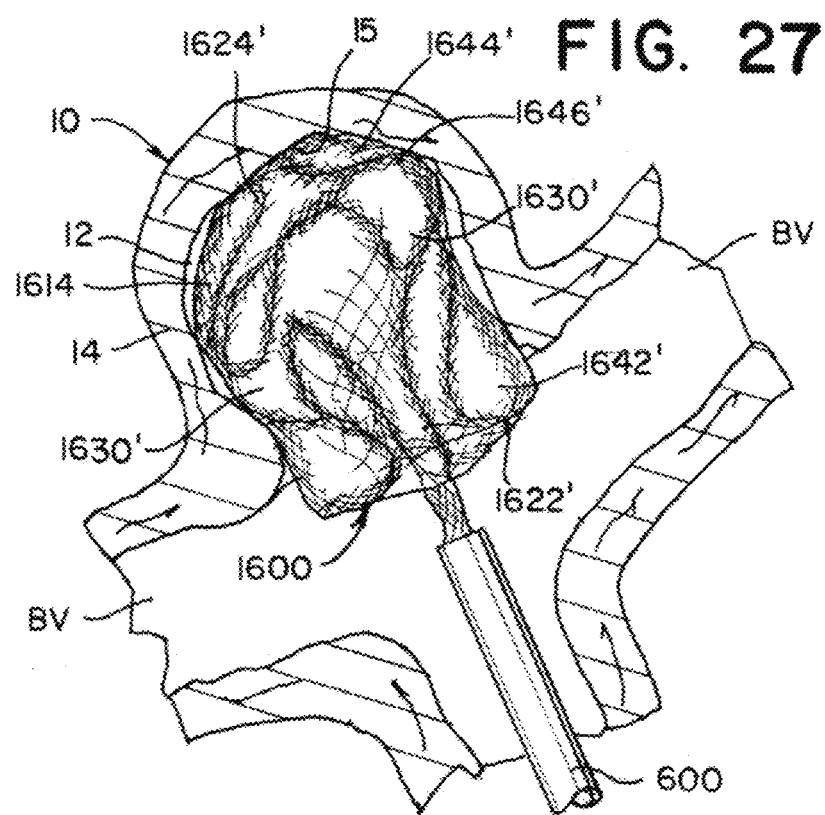

FIG. 30
FIG. 31
FIG. 32
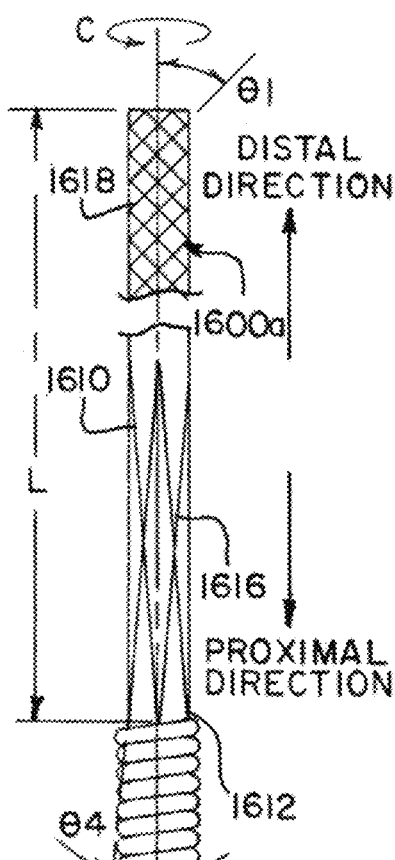
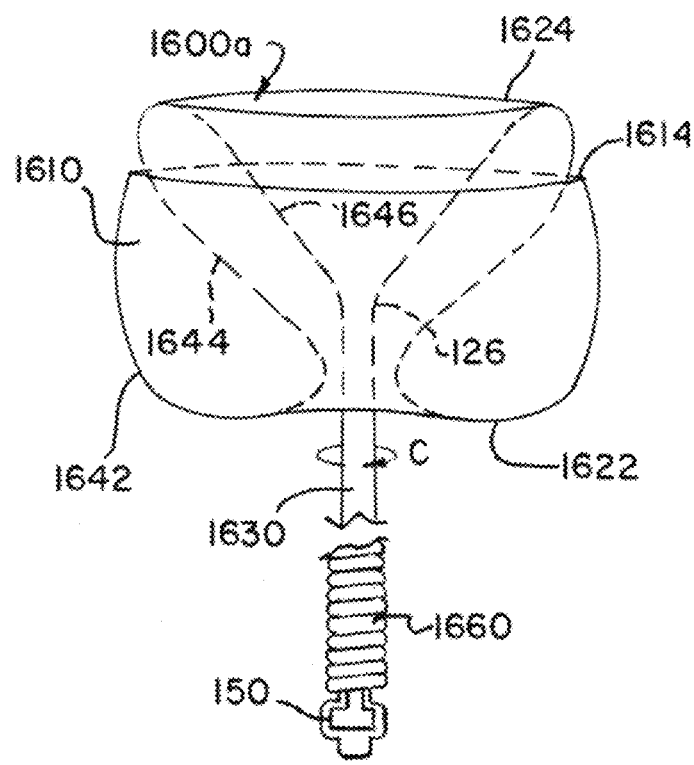
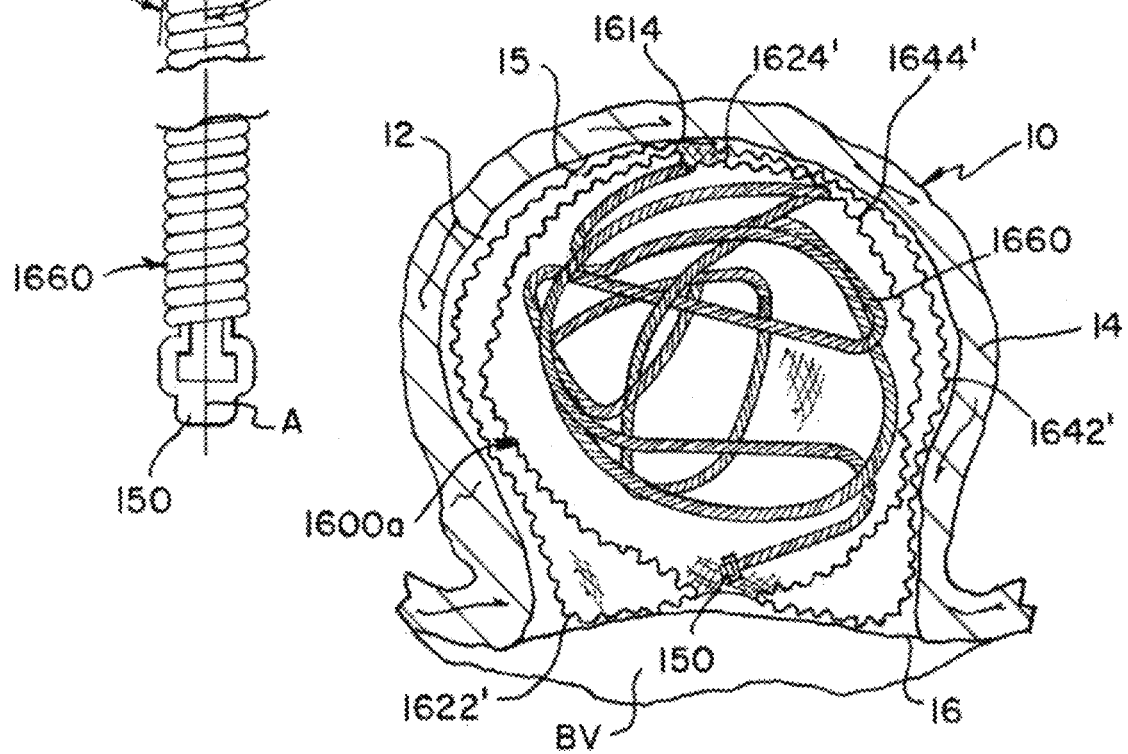

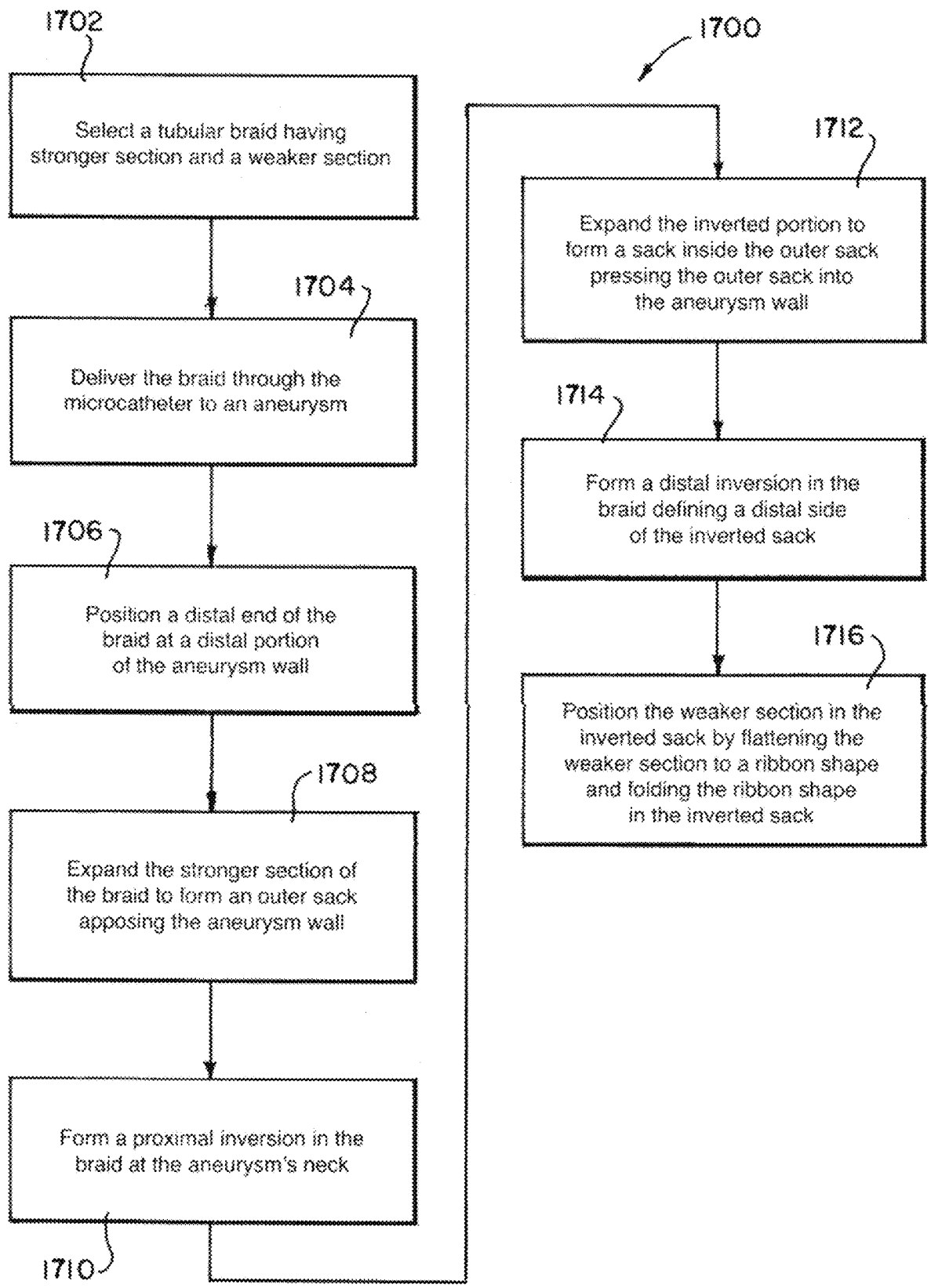

INVERTING BRAIDED ANEURYSM TREATMENT SYSTEM AND METHOD

CROSS-REFERENCE TO RELATED APPLICATIONS

The present application is a continuation-in-part of U.S. patent application Ser. No. 16/865,116 and U.S. patent application Ser. No. 16/865,165 each filed May 1, 2020 and which are each a continuation-in-part of U.S. patent application Ser. No. 16/748,877 filed Jan. 22, 2020 and a continuation-in-part of U.S. patent application Ser. No. 16/853,135 filed Apr. 20, 2020. U.S. patent application Ser. No. 16/748,877 and U.S. patent application Ser. No. 16/853,135 are each a continuation-in-part of U.S. patent application Ser. No. 16/418,199 filed May 21, 2019 and issued as U.S. Pat. No. 10,653,425 on May 19, 2020.

The present application is also a continuation-in-part of U.S. patent application Ser. No. 16/703,973 filed Dec. 5, 2019.

The contents of all of which are incorporated herein by reference in their entirety as if set forth herein.

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material or block the entrance or neck of the aneurysm. Both approaches attempt to prevent blood flow into the aneurysm. When filling an aneurysm sac, the embolic material clots the blood, creating a thrombotic mass within the aneurysm. When treating the aneurysm neck, blood flow into the entrance of the aneurysm is inhibited, inducing venous stasis in the aneurysm and facilitating a natural formation of a thrombotic mass within the aneurysm.

Current intravascularly delivered devices typically utilize multiple embolic coils to either fill the sac or treat the entrance of the aneurysm. Naturally formed thrombotic masses formed by treating the entrance with embolic coils can result in improved healing compared to aneurysm masses packed with embolic coils because naturally formed thrombotic masses can reduce the likelihood of distention from arterial walls and facilitate reintegration into the original parent vessel shape along the neck plane. However, embolic coils delivered to the neck of the aneurysm can potentially have the adverse effect of impeding the flow of blood in the adjoining blood vessel, particularly if the entrance is overpacked. Conversely, if the entrance is insufficiently packed, blood flow can persist into the aneurysm. Treating certain aneurysm morphology (e.g. wide neck, bifurcation, etc.) can require ancillary devices such a stents or balloons to support the coil mass and obtain the desired packing density. Once implanted, the coils cannot easily be retracted or repositioned. Furthermore, embolic coils do not always effectively treat aneurysms as aneurysms treated with multiple coils often recanalize or compact because of poor coiling, lack of coverage across the aneurysm neck, blood flow, or large aneurysm size.

Alternatives to embolic coils are being explored, for example a tubular braided implant is disclosed in U.S. Pat. No. 10,751,066, incorporated herein by reference. Tubular braided implants have the potential to easily, accurately, and safely treat an aneurysm or other arterio-venous malformation in a parent vessel without blocking flow into perforator vessels communicating with the parent vessel. Compared to embolic coils, however, tubular braided implants are a newer technology, and there is therefore capacity for improved geometries, configurations, delivery systems, etc. for the tubular braided implants.

There is therefore a need for improved methods, devices, and systems for implants for aneurysm treatment.

SUMMARY

An example system can include a tubular braid, a catheter, and an embolic coil. The tubular braid can have an open end, a pinched end, and a predetermined shape. In the predetermined shape the braid can have a first segment extending from the open end to a first inversion, a second segment extending from the first inversion to the second inversion, and a third segment surrounded by the second segment and extending from the second inversion to the pinched end. The second segment can form a sack having an opening approximate the first inversion. The catheter can have a lumen therethrough, a distal end, and an outer diameter at the distal end that is sized to be inserted into the sack through the opening of the sack. The embolic coil is detached from the tubular braid and is positioned within the lumen. The embolic coil is configured to exit the distal end of the catheter.

The tubular braid can be stable in an implanted shape, that is based on the predetermined shape, when the tubular braid is constricted by a substantially spherical cavity. In the implanted shape, at least a portion of the first segment can be positioned to contact a cavity wall of the substantially spherical cavity, a proximal inversion corresponding to the first inversion of the predetermined shape can be positioned at an entrance to the substantially spherical cavity, the sack can be positioned within the substantially spherical cavity, the opening of the sack can be accessible at the entrance to the substantially spherical cavity, and the opening can be configured to receive the distal end of the catheter into the sack. In the implanted shape, the braid can have pores near the proximal conversion that are sized such that the catheter can pass through one of the pore so that the distal end of the catheter is positioned between the first segment and the sack.

In the implanted shape, the opening can be resilient to expand to receive the distal end of the catheter and contract when the catheter is removed from the opening.

The embolic coil can be sized to fit within the sack when the tubular braid is in the implanted shape.

In the predetermined shape, the tubular braid can be cylindrically symmetrical about a central axis and the second segment can include a columnar section extending in a proximal direction from the sack, constricted about the central axis, and defining the opening of the sack.

In the predetermined shape, the second segment can include a bend of approximately 90° separating the sack from the columnar section.

A diameter of the columnar section when the braid is in the predetermined shaped can collapse when the braid is in the implanted shape.

The columnar section can be columnar in shape when the tubular braid is in the implanted shape.

The outer profile of the tubular braid in the predetermined shape can be approximately a right cylinder. Alternatively, the outer profile of the tubular braid in the predetermined shape can be approximately pear shaped.

An example tubular braid of an aneurysm implant can have an open end and a pinched end. The tubular braid can have a predetermined shape and an implanted shape in which the tubular braid is stable when constricted by a substantially spherical cavity.

In the predetermined shape the braid can have a first segment extending from the open end to a first inversion, a second segment extending from the first inversion to the second inversion and forming a sack comprising an opening approximate the first inversion, and a third segment surrounded by the second segment and extending from the second inversion to the pinched end. The implanted shape can be based on the predetermined shape. In the predetermined shape, the tubular braid can be cylindrically symmetrical about a central axis and the second segment can include a columnar section extending in a proximal direction from the sack, constricted about the central axis, and defining the opening of the sack.

In the implanted shape at least a portion of the first segment can be positioned to contact a cavity wall of the substantially spherical cavity, a proximal inversion corresponding to the first inversion of the predetermined shape can be positioned at an entrance to the substantially spherical cavity, the sack can be positioned within the substantially spherical cavity, and the opening of the sack is twisted to thereby inhibit access to the sack via the opening. In the implanted shape, the columnar section can be twisted about the central axis.

An example method of treating an aneurysm can include any combination of the steps presented as follows in no particular and can include additional steps not presented herein. A braid can be delivered, in a delivery configuration, via attachment to a delivery system, through a catheter. The braid can include an outer surface in the delivery configuration. A braid sack can be created within an aneurysm sac such that the braided sack includes an interior surface that corresponds to an exterior surface of the braid in the delivery configuration. The braid can be detached from the delivery system, thereby implanting the braid in an implanted shape within the aneurysm sac. After detaching the braid from the delivery system, an embolic coil can be inserted into the braided sack.

The method can further include apposing a first portion of the braid to an aneurysm wall. The method can further include creating a proximal inversion by inverting the braid approximate an aneurysm neck. The method can further include creating a distal inversion by inverting the braid within the aneurysm sac so that the braided sack extends between the proximal inversion and the distal inversion.

The method can further include encircling the braided sack with an open end of the first portion while the braid is within the aneurysm sac in the implanted shape.

The braid can be implanted such that implanted shape is based in part on a predetermined shape of the braid and based in part on the geometry of the aneurysm sac.

The braid can be implanted such that the proximal inversion and the distal inversion correspond to respective inversions of the braid when the braid is in the predetermined shape.

The method can further include allowing the braid to self-anchor within the aneurysm after detaching the braid from the delivery system.

The method can further include expanding the braided sack with the embolic coil.

Detaching the braid from the delivery system can further include releasing a pinched end of the braid from the delivery system so that the pinched end is suspended within the braided sack. Alternatively, detaching the braid from the delivery system can further include releasing a pinched end of the braid from the delivery system so that the pinched end is positioned approximate a plane defined by the aneurysm neck.

The braid can be delivered in the delivery configuration such that, a pinched end of the braid is in contact with the delivery system and the braid extends in a single layer tubular shape in a distal direction from the pinched end to a distal open end of the braid.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1C is an illustration of the example implant with the tubular braid in a second implanted shape according to aspects of the present invention;

FIGS. 2A through 2H are illustrations of an implant having a tubular braid that expands to a predetermined shape similar to as illustrated in FIG. 1A as the tubular braid exits a microcatheter according to aspects of the present invention;

FIGS. 3A through 3H are illustrations of the implant showing the tubular braid expanding to a first implanted shape and a second implanted shape within an aneurysm according to aspects of the present invention;

FIG. 4A is an illustration of the implant showing the tubular braid expanded in the first implanted shape in a tube having a 5 mm diameter according to aspects of the present invention;

FIG. 4B is an illustration of the implant showing the tubular braid expanded in the second implanted shape in a tube having a 4 mm diameter according to aspects of the present invention;

FIGS. 15A to 15C illustrate example implants with one or more corrugated folds in a predetermined shape according to aspects of the present invention;

FIGS. 18A through 18I are illustrations of an implant having a tubular braid that expands to an implanted shape similar to as illustrated in FIG. 17B as the tubular braid exits a microcatheter according to aspects of the present inventions;

FIG. 23 is a flow diagram for a method of treating an aneurysm;

FIG. 24 is a flow diagrams for a method of forming an occlusive device to treat an aneurysm;

FIGS. 27A through 27I are illustrations of steps of an aneurysm treatment process according to aspects of the present invention;

FIG. 30 is an illustration of an implant having a braid and an embolic coil each shaped for delivery through a catheter according to aspects of the present invention;

FIG. 31 is an illustration of an implant having a braid and an embolic coil with the braid in a predetermined shape according to aspects of the present invention;

FIG. 32 is an illustration of an implant having a braid and an embolic coil implanted in an aneurysm according to aspects of the present invention;

FIG. 33 is a flow diagram listing method steps that can be performed according to aspects of the present invention;

DETAILED DESCRIPTION

Examples presented herein generally include a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted.

Figure 1A:
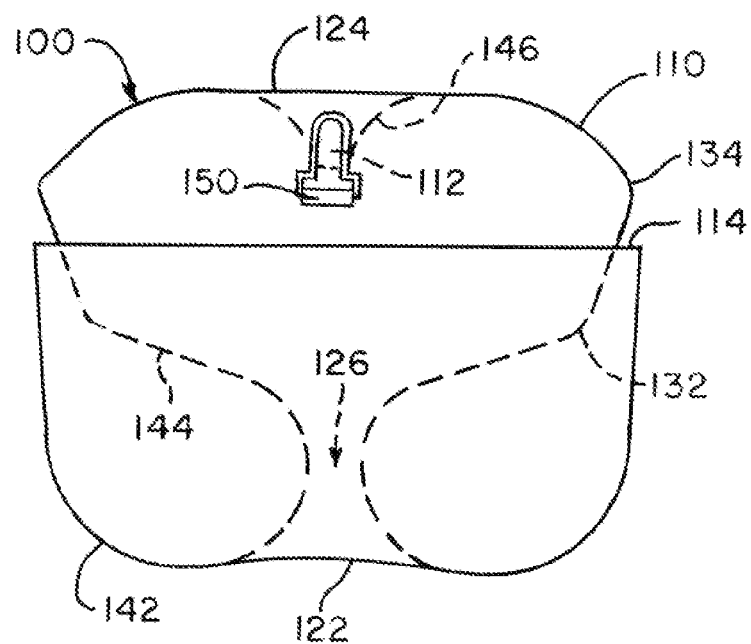
FIG. 1A is an illustration of an example implant having a tubular braid in a predetermined shape according to aspects of the present invention.
Figure 1B:
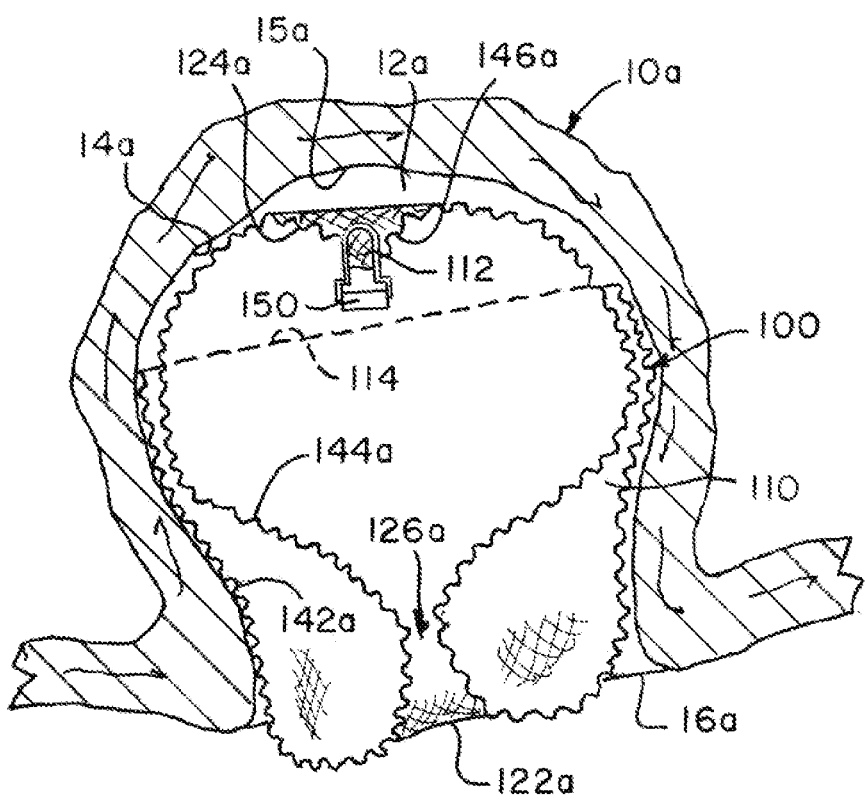
FIG. 1B is an illustration of the example implant with the tubular braid in a first implanted shape according to aspects of the present invention.

FIGS. 1A through 1C are illustrations of an example braided implant 100 that can have a predetermined shape as illustrated in FIG. 1A and two distinct implanted shapes as illustrated in FIGS. 1B and 1C. The implant 100 can treat a range of aneurysm sizes including a larger aneurysm 10a as illustrated in FIG. 1B and a smaller aneurysm 10b as illustrated in FIG. 1C. The implant 100 can have a first implanted shape (FIG. 1B) that can be conducive for treating larger aneurysms 10a and a second implanted shape (FIG. 1C) that can be conducive for treating smaller aneurysms 10b. The implant 100 can include a tubular braid 110 having an open end 114 and a pinched end 112. The implant 100 can include a detachment feature 150 attached to the braid 110 at the pinched end 112. The tubular braid 110 can be formed in the predetermined shape (FIG. 1A), collapsed for delivery through a microcatheter, attached to a delivery system at the detachment feature 150, and implanted in a shape similar to one or the other of the two implanted shapes (FIG. 1B or FIG. 1C).

Referring to FIG. 1A, when in the predetermined shape, the tubular braid 110 can include two inversions 122, 124, dividing the braid 110 into three segments 142, 144, 146. In the predetermined shape, the braid 110 can have an outer segment 142 extending from the open end 114 of the braid 110 to one of the inversions 122, an inner segment 146 extending from the pinched end 112 of the braid 110 to the other of the inversions 124, and a middle segment 144 extending between the two inversions 122, 124. When in the predetermined shape, the tubular braid 110 can be substantially radially symmetrical about a central vertical axis y (see FIG. 6A). FIG. 1A illustrates a profile of each segment 142, 144, 146, and the detachment feature 150 is illustrated as a flat key that can be used with a mechanical implant delivery system (not illustrated).

The tubular braid 110 can be formed into the predetermined shape by first inverting the braid outwardly to separate the inner segment 146 from the middle segment 144 with an inversion 124, then the middle segment 144 can be shaped over a form to produce the substantially "S" shaped profile illustrated, and finally, the braid 110 can be inverted outwardly again to separate the middle segment 144 from the outer segment 142 with another inversion 122. If necessary, the braid can be trimmed at the open end 114. The open end 114 can be positioned to encircle the middle segment 144. The open end 114 can positioned within the middle third section of the braid's height as illustrated.

It can be advantageous to minimize a neck opening 126 defined by the lower extension of the "S" shape of the middle segment 144 to maximize occlusion of an aneurysm neck when the implant 100 is implanted. The middle segment 144 can have one or more bends 132, 134. The bends 132, 134 can be positioned facilitate the movement of the braid 110 into the second implanted shape illustrated in FIG. 1C and the bends 132, 134 can be positioned to stabilize the braid 110 in the first and/or second implanted shape.

The tubular braid 110 can include memory shape material that can be heat set to a predetermined shape, can be deformed for delivery through a catheter, and can self-expand to an implanted shape that is based on the predetermined shape and confined by the anatomy of the aneurysm in which it is implanted.

As illustrated in FIG. 1B, when in the first implanted shape, the braid 110 can have an outer layer 142a contacting the aneurysm's wall 14a, a sack 144a nested within the outer layer 142a, a proximal inversion 122a positioned at the aneurysm's neck 16a, and a distal inversion 124a positioned near a distal portion 15a of the aneurysm wall 14a. In the first implanted shape, the detachment feature 150 and pinched end 112 of the braid 110 can be suspended within the sack 144a.

As illustrated in FIGS. 1A and 1B, the tubular braid 110 in the first implanted shape can be radially compressed and vertically extended compared to the predetermined shape. The outer layer 142a in the first implanted shape can correspond to the outer layer 142 in the predetermined shape, the proximal inversion 122a in the first implanted shape can correspond to the inversion 122 adjacent to the outer layer 142 in the predetermined shape, the sack 144a in the first implanted shape can correspond to the middle segment 144 in the predetermined shape, the distal inversion 124a in the first implanted shape can correspond to the inversion 124 adjacent to the inner segment 146 in the predetermined shape, and an inner braid segment 146a suspending the detachment feature 150 in the first implanted shape can correspond to the inner segment 146 in the predetermined shape. In the first implanted shape, the sack 144a can have a neck opening 126a corresponding to the neck opening 126 in the predetermined shape.

As illustrated in FIG. 1C, when in the second implanted shape, the braid 110 can have an outer layer 142b contacting the aneurysm's wall 14b, a proximal inversion 122b positioned at the aneurysm's neck 16b, a middle layer 144b extending within the outer layer 142b and pressing against the outer layer 142b, a distal inversion 124b positioned near the open end 114 of the braid 110, and an inner layer 146b extending within the middle layer 144b and pressing against the middle layer 144b. In the second implanted shape, the detachment feature 150 and pinched end 112 of the braid 110 can be positioned at the aneurysm neck 16b, near the proximal inversion 122b.

As illustrated in FIGS. 1A and 1C, the tubular braid 110 in the second implanted shape can be radially compressed compared to the predetermined shape, and the middle segment 144 of the predetermined shape can be folded so that the height of the tubular braid 110 is compressed in the second implanted shape compared to the predetermined shape.

Alternatively, when implanted in the second implanted shape in aneurysms having a diameter that is significantly smaller than the aneurysm's height, the second implanted shape can be radially compressed compared to the predetermined shape and the height of the braid in the second implanted shape can be greater than the height of the braid in the predetermined shape.

The outer layer 142b in the second implanted shape can correspond to the outer layer 142 in the predetermined shape, the proximal inversion 122b in the second implanted shape can correspond to the inversion 122 adjacent to the outer layer 142 in the predetermined shape, the middle layer 144b and inner layer 146b in the second implanted shape can correspond to the middle segment 144 in the predetermined shape, the distal inversion 124b in the second implanted shape can correspond to a bend 134 in the middle segment 144 in the predetermined shape, and a portion of the braid 110 near the detachment feature 150 forming the inner layer 146b in the second implanted shape can correspond to the inner segment 146 in the predetermined shape.

Figures 2C, 2D, 2E:
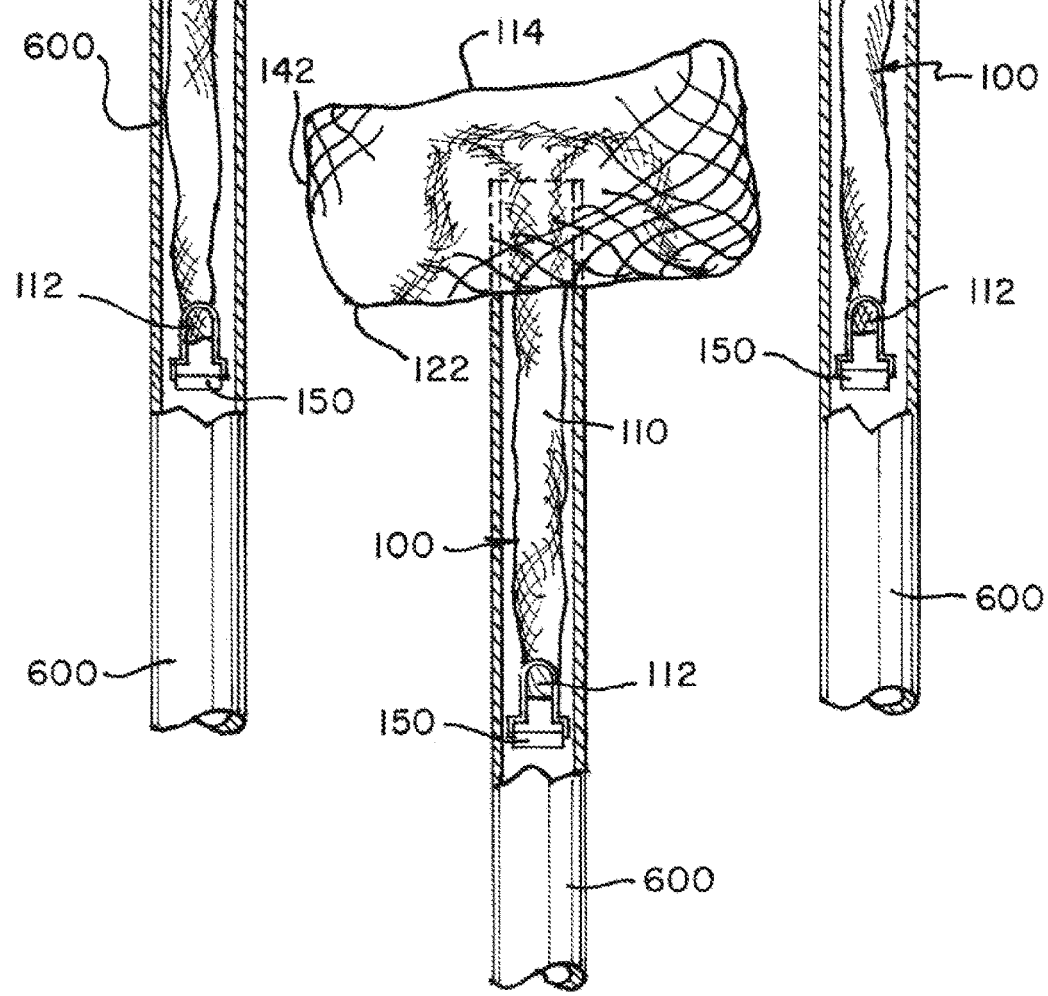

FIGS. 2A through 2H are illustrations of an example implant 100 having a braid 110 expanding to a predetermined shape as the braid 110 exits a microcatheter 600. The implant 100 has a predetermined shape similar to as illustrated in FIG. 1A. As illustrated in FIG. 2A, the braid 110 can be shaped to a delivery shape that is extended to a single layer of tubular braid having a compressed circumference/diameter sized to be delivered through the microcatheter 600 and a length L. The illustrated implant 100 has a length L of between about 22 mm and about 25 mm. As will be appreciated and understood by a person of ordinary skill in the art, the length L of a specific braid 110 can be tailored based on the size and shape of the aneurysm being treated.

During delivery through the microcatheter 600, the detachment feature 150 can be attached to a delivery system at a proximal end of the implant 100, the pinched end 112 can be positioned near the proximal end of the implant 100, and the open end 114 can define the distal end of the implant 100. Collapsing the braid 110 to a single layer tube can result in a braid 110 that has a sufficiently small diameter and a sufficiently short length L to mitigate effects of friction force on the braid 110 when it is delivered through the microcatheter, allowing the braid 110 to be delivered unsheathed in some applications.

As illustrated in FIG. 2B, the open end 114 can be positioned to exit the microcatheter 600 before any other portion of the braid 110 exits the microcatheter. The open end 114 can expand as it exits the microcatheter 600. If the open end 114 is unconstrained by an aneurysm as illustrated, the open end can expand to its circumference in the predetermined shape.

As illustrated in FIG. 2C, the distal portion of the braid 110 can continue to expand radially as it exits the microcatheter 600.

As illustrated in FIG. 2D, the braid 110 can form the inversion 122 defining the outer segment 142 as the braid 110 is further pushed out of the microcatheter 600.

Figure 2F:
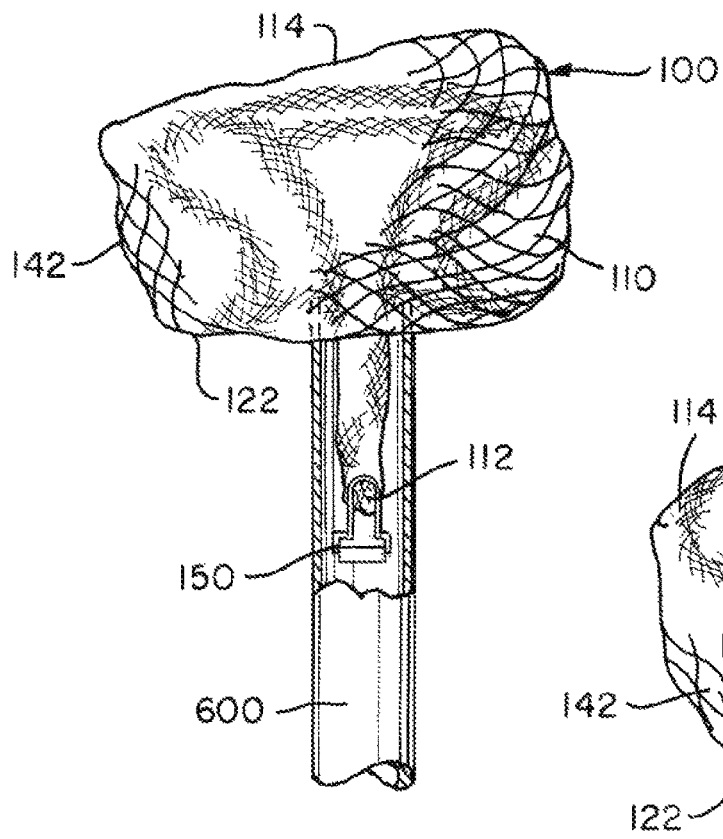
Figure 2G:
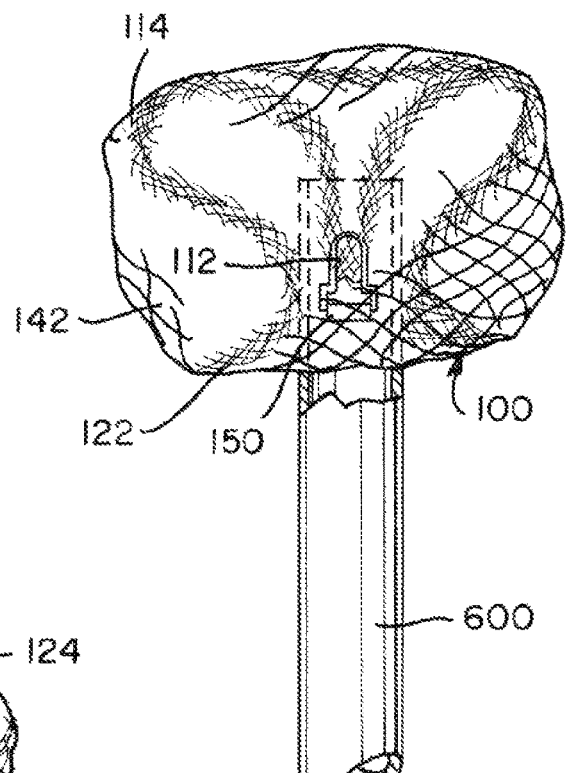

As illustrated in FIGS. 2E through 2G, the "S" shape of the middle segment 144 can begin to form as the braid 110 is further pushed from the microcatheter 600.

Figure 2H:
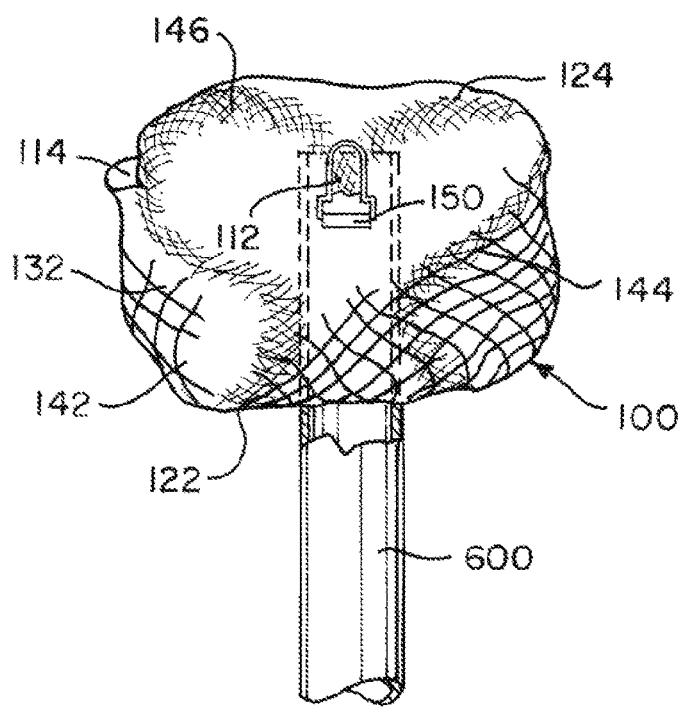

As illustrated in FIG. 2H, when all, or nearly all of the braid 110 exits the microcatheter 600, the braid 110, not confined by an aneurysm, can expand to a predetermined shape similar to the shape illustrated in FIG. 1A. In the predetermined shape, the braid 110 of the illustrated implant has a diameter between about 6 mm and about 6.5 mm and a height between about 5 mm and about 5.5 mm.

The ratio of the outermost diameter of the braid 110 in the predetermined shape illustrated in FIG. 2H to the length of the braid 110 in the delivery shape illustrated in FIG. 2A is between about 0.3 and about 0.24.

FIGS. 3A through 3H are illustrations of the implant 100 illustrated in FIGS. 2A through 2H expanding within an aneurysm 10 in two different implanted shapes. The aneurysm 10 has a height of about 6 mm, a diameter of about 6 mm, and a neck diameter of about 4 mm. Comparing the dimensions of the aneurysm 10 to the braid 110 in the predetermined shape illustrated in FIG. 2H, the braid 110 has a slightly larger diameter and a slightly smaller height, and the interior of the aneurysm 10 is substantially spherical while the outer dimensions of the braid 110 are more cylindrical (see FIGS. 6A and 6B for measurement orientation). When the braid 110 of the implant 100 is confined by the aneurysm 10, the braid 110 is therefore be radially constrained.

As illustrated in FIG. 3A, the implant 100 can be delivered to the aneurysm 10 through the microcatheter 600, as described in relation to FIG. 2A. The open end 114 of the tubular braid 110 can expand within the aneurysm 10 as it exits the microcatheter 600. The illustrated aneurysm 10 is positioned at a bifurcation including a stem blood vessel 20 and two branch vessels 22a, 22b, and the microcatheter 600 is illustrated being delivered through the stem blood vessel 20. It is contemplated that the implant could be delivered to an aneurysm on a sidewall of a blood vessel through a curved microcatheter, and such a procedure is intended to be embraced by the scope of the present disclosure.

As illustrated in FIG. 3B, as the braid 110 is further pushed distally from the microcatheter 600, the braid 110 can expand to appose the aneurysm wall 14 and conform to the aneurysm neck 16. The aneurysm 10 being treated can have a diameter that is less than the outer diameter of the tubular braid 110 in the predetermined shape so that the braid 110 tends to expand outwardly, providing a force against the aneurysm wall 14, and sealing around the perimeter of the aneurysm neck 16. The implant 100 can be particularly suitable for treating a wide neck aneurysm such as commonly occur at bifurcations because the radial force provided by the braid 110 against the aneurysm wall 14 and perimeter of the neck 16 can be sufficient to both anchor the implant 100 in a wide neck aneurysm and seal the neck 16 of the aneurysm 10.

Figure 3C:
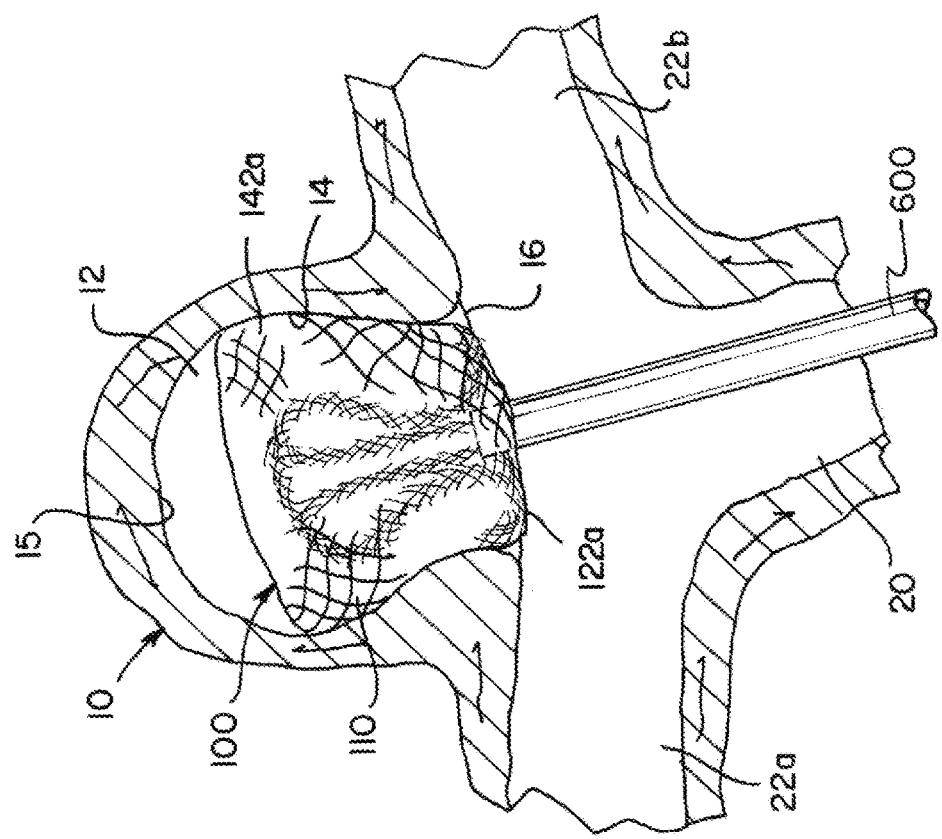

As illustrated in FIG. 3C, as the braid 110 is further pushed distally from the microcatheter 600, the proximal inversion 122a can be formed.

Figure 3D:
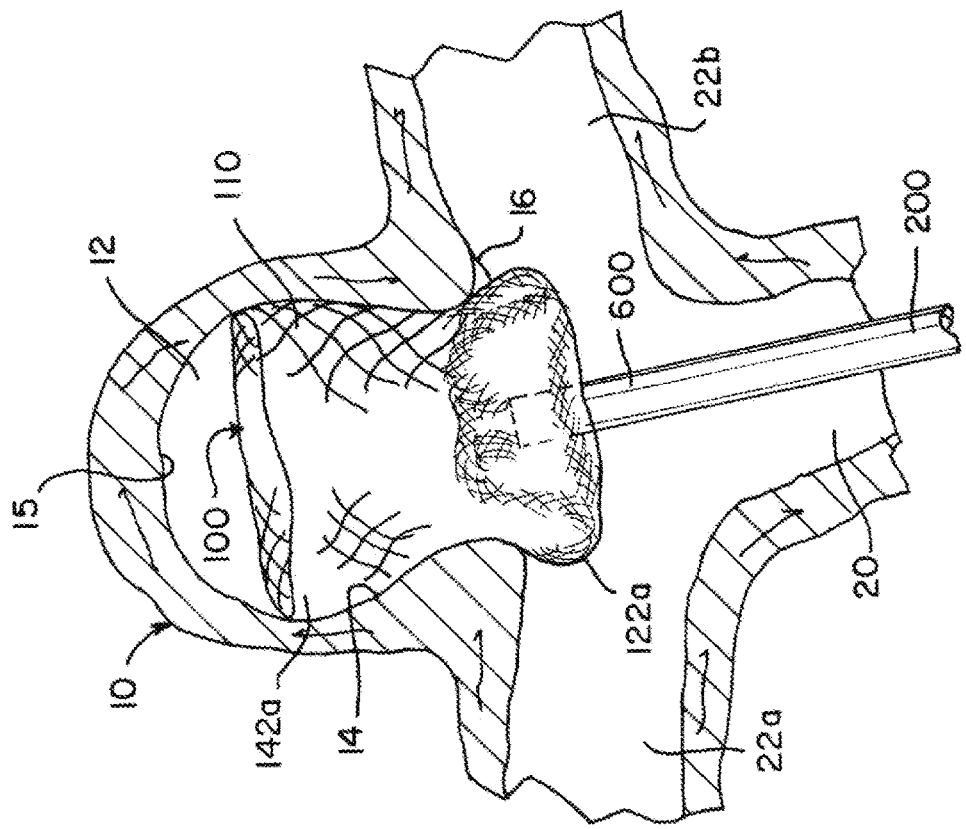

As illustrated in FIG. 3D, the microcatheter 600 can be manipulated to place the proximal inversion 122a at the aneurysm neck 16. The proximal inversion 122a can be placed on a proximal side of a plane defining a boundary 18 (See FIG. 6B) between the aneurysm 10 and the branch vessels 22a, 22b. In some applications it can be advantageous to place the proximal inversion 122a far enough in the proximal direction from the plane 18 so that the outer layer 142a of the braid 110 seals around the outer perimeter of the aneurysm neck 16, but not so far proximally that the implant 100 becomes an obstruction to the blood vessels 22a, 22b, 20.

As illustrated in FIG. 3E, the braid 110 can expand within the aneurysm sac 12 and extend to appose an inner surface of the outer layer 142a of the braid 110. The apposition to the outer layer 142a can provide additional force to anchor the outer layer 142a to the aneurysm wall 14.

As illustrated in FIG. 3F, the aneurysm 10 has a height that can accommodate the tubular braid 110 in the first implanted shape similar to that illustrated in FIG. 1B. Because the braid 110 is radially constrained and has a more cylindrical shape compared to the substantially spherical shape of the aneurysm, the braid 110 can extend beyond the height of the predetermined shape to accommodate aneurysms taller than the predetermined shape. In the illustration, the tubular braid 110 of the implant 100 in the predetermined shape has a height between about 0.5 mm and 1 mm less than the height of the aneurysm, or in other words, the implant has extended between about 10% and about 20% in height in the first implanted shape compared to the predetermined shape.

The braid can be pulled proximally as illustrated in FIG. 3G to form a second implanted shape as illustrated in FIG. 3H that is similar to the second implanted shape illustrated in FIG. 1C, but different in that the aneurysm 10b illustrated in FIG. 1C is smaller (proportionally compared to the braid 110) than the mock aneurysm 10 illustrated in FIG. 3H. Before the implant 100 is released from the delivery system, the implant 100 can be partially or fully retracted into the microcatheter 600 and repositioned in either of the first implanted shape or the second implanted shape. Additionally, or alternatively, the microcatheter 600 can be moved distally to move the braid 110 from the second implanted shape illustrated in FIG. 3H to the first implanted shape illustrated in FIG. 3F. In some applications, while positioning the implant 100, a physician can choose whether the first implanted shape or the second implanted shape is more suitable for the anatomy of the aneurysm and treatment site. For treatments involving aneurysms and implants shaped similar to the aneurysm 10 and implant 100 illustrated in FIGS. 3A through 3H, it can be more advantageous to shape the braid 110 in the first implanted shape as illustrated in FIG. 3F (rather than the second implanted shape illustrated in FIG. 3G) because the first implanted shape in this example implementation provides a larger surface area of the braid 110 in contact with the aneurysm wall 14.

FIGS. 4A and 4B are illustrations of the braid 110 of the example implant illustrated in FIGS. 2A through 2H and 3A through 3H showing the tubular braid 110 expanded within tubes to determine a range of aneurysm diameters and aneurysm heights that an implant 100 having the dimensions of the example implant 100 would be suitable for treating. FIG. 4A illustrates the braid 110 in a tube having a 5 mm diameter. The braid 110 is in the first implanted shape and has a height of about 8 mm. The braid 110 is therefore radially constrained from its predetermined shape by between about 1 mm and 1.5 mm in diameter, or between about 17% and 23%, and expanded vertically in height by between about 2.5 mm and 3 mm, or between about 45% and 60%.

FIG. 4B illustrates the braid 110 in a tube having a 4 mm diameter. The braid 110 is in the second implanted shape and has a height of about 6 mm. The braid is therefore radially constrained from its predetermined shape by between about 2 mm and 2.5 mm in diameter, or between about 33% and 38%, and expanded vertically between about 0.5 mm and 1 mm, or between about 10% and 20%.

Implants having a predetermined shape and dimensions as illustrated and described in relation to FIG. 2H can therefore be suitable for treating aneurysms having a diameter between and including about 4 mm and about 5 mm and a height between and including about 6 mm and about 8 mm. As illustrated in FIG. 3F, the implant can also be suitable for treating an aneurysm having a diameter of 6 mm and a height of 6 mm. As will be appreciated and understood by a person of ordinary skill in the art, the dimensions of the tubular braid in the predetermined shape can be tailored to treat aneurysms within a range of sizes not specifically outlined herein according to the principles described herein. It is contemplated that a collection of implants so shaped can be made available to physicians, and a physician can choose a suitable implant from the collection based on aneurysm height, diameter, neck diameter, and/or other anatomical features.

A collection of implants, each having a uniquely shaped tubular braid can be created to provide a catalogue of implants for treating aneurysms ranging in diameter and height. The catalogue can include implants suitable for treating aneurysms ranging from 3 mm to 15 mm in diameter and ranging from 3 mm to 15 mm in height, or in another example, ranging from 3 to 11 mm in diameter and 3 to 7 mm in height. As will be appreciated and understood by a person of ordinary skill in the art, some aneurysm dimensions are extremely rare, and the catalog need not include implants for treating aneurysms having a large height:diameter ratio or a large diameter:height ratio.

Each implant in the collection can be suitable for treating aneurysms with a sub range of diameters and a sub-range of heights. An example catalogue can include a listing of implants for treating aneurysms of one or more of, but not limited to, the following size sub ranges (diameter range in mm, height range in mm): (3-5, 3-5), (6-8, 4-5), and (9-11, 5-7).

In some examples, each size sub range can be treated by a single implant having a tubular braid uniquely sized and shaped to be suitable for treating aneurysms within that sub range. In some examples, the sub ranges in the catalogue can be represented by implants each having a tubular braid with a delivery length (length when the braid is collapsed for delivery through a microcatheter) that is about 10 mm, about 40 mm, and/or including a length in between.

As will be appreciated and understood by a person of ordinary skill in the art, aneurysm height and diameter are measured with some margin of error. To that end, the size sub range included in the catalogue for a given implant can represent a portion of aneurysm sizes that can be treated with the implant and the implant can treat aneurysms outside of the listed sub range. For instance, an implant listed for treating aneurysms having heights between height a and height b and diameter range between diameter x and diameter y can be suitable for treating aneurysms slightly taller than the maximum listed height b if the diameter of the aneurysm is near the lower limit of the range (about diameter x), the implant can be suitable for treating diameters slightly larger than diameter y if the height of the aneurysm is near the lower limit of the height range (about height a).

Figure 5A:
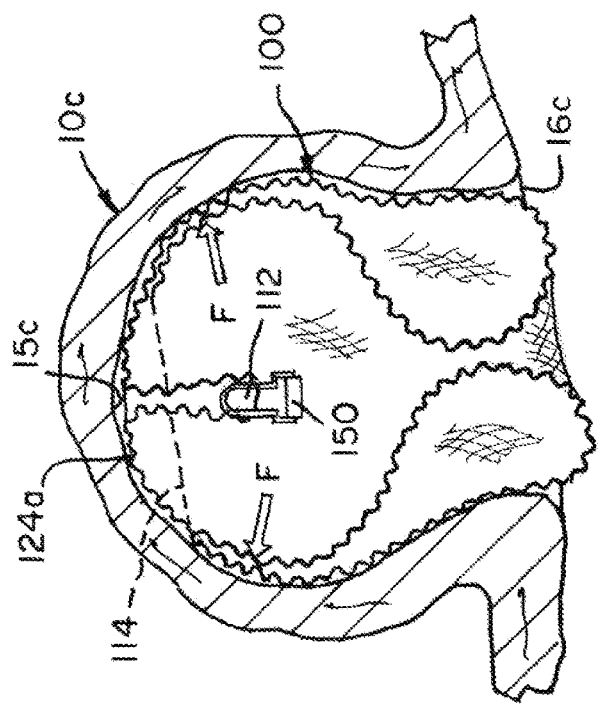
FIGS. 5A through 5D are illustrations of the example implant as illustrated in FIGS. 1A through 1C implanted in either the first implanted shape or the second implanted shape in aneurysms ranging in size according to aspects of the present invention.
Figure 5B:
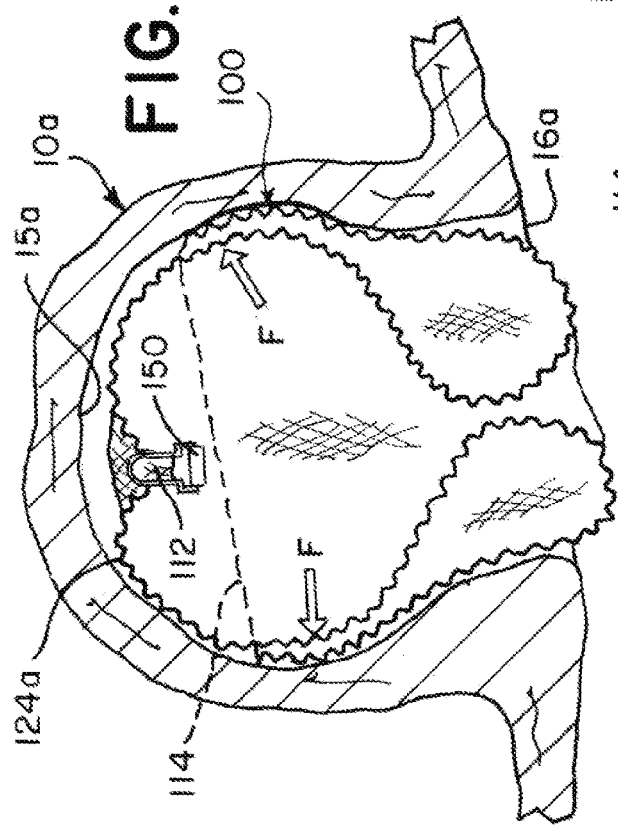
Figure 5C:
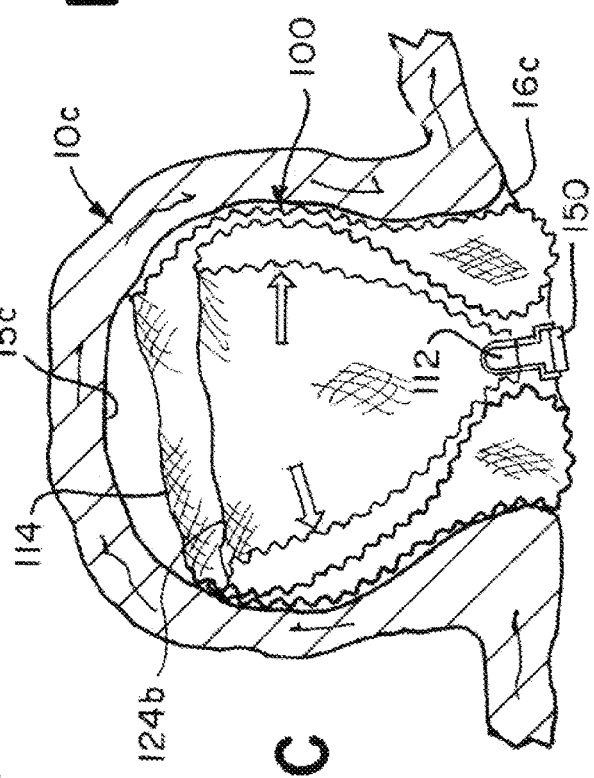
Figure 5D:
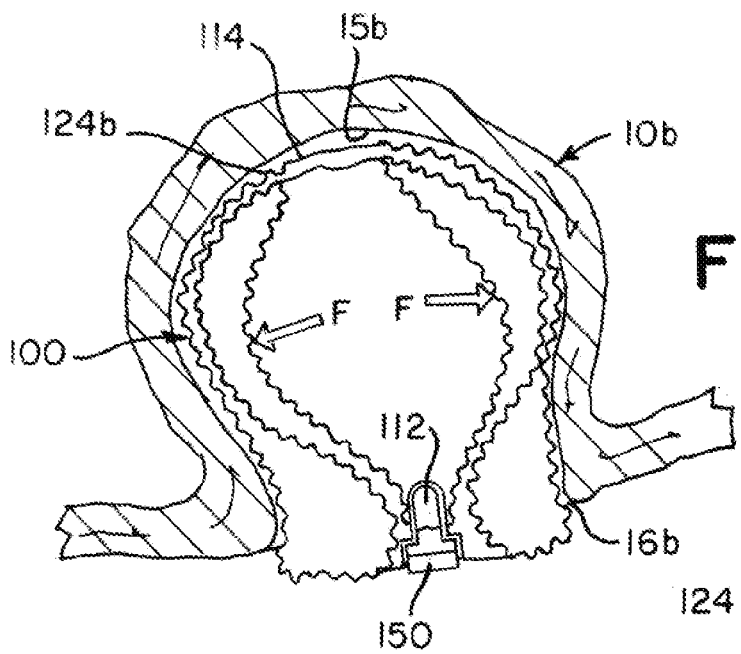

FIGS. 5A through 5D are illustrations of the example implant 100 as illustrated in FIGS. 1A through 1C implanted in either the first implanted shape or the second implanted shape in aneurysms ranging in size. FIG. 5A illustrates a large aneurysm 10a, FIGS. 5B and 5C illustrate a medium aneurysm 10c, and FIG. 5D illustrates a small aneurysm 10b. The implant 100 is advantageously implanted in an aneurysm 10a, 10b, 10c having a diameter about equal to or smaller than the diameter of the braid 110 in the predetermined shape so that the braid 110 provides an outward force F against the aneurysm wall 14 when implanted. The braid 110 can have inner layers that press against one or more outer layers, contributing to the force F.

As illustrated in FIG. 5A, the maximum size of an aneurysm 10a that the implant 100 can be suitable for treating can be determined by the dimensions that the braid 110 can take in the first implanted shape. The pinched end 112 and detachment feature 150 can be positioned near a distal portion 15a of the aneurysm wall 14a as similarly illustrated in FIG. 1B.

As illustrated in FIG. 5B, the implant 100 can also be suitable for treating a medium sized aneurysm 10c that is smaller than the aneurysm 10a illustrated in FIG. 5A in the first implanted shape. To fit within the medium aneurysm 10c in the first implanted shape, the pinched end 112 and detachment feature 150 can be positioned away from the distal portion 15c of the aneurysm wall compared to the position of the pinched end 112 and detachment feature 150 in the large aneurysm 10a. In the predetermined shape (see FIG. 1A), the middle segment 144 can include a bend 134 to stabilize the tubular braid 110 in the first implanted shape in the medium aneurysm 10c as illustrated in FIG. 5B.

As illustrated in FIG. 5C, the implant 100 can also be suitable for treating the medium sized aneurysm 10c in the second implanted shape. The middle segment 144 of the braid in the predetermined shape (see FIG. 1A) can be folded to form a middle layer 144b and an inner layer 146b similar to as described in relation to FIG. 1C. In some applications, either implanted shape could be effective for treating the aneurysm 10c, and a physician can select a preferred shape during treatment. For instance, a physician can decide to use the first implanted shape (FIG. 5B) to elongate the implant so that the proximal fold 122a can be placed proximally outside of the aneurysm neck, or the physician can decide to use the second implanted shape (FIG. 5C) to provide more layers of braid at the aneurysm neck to occlude the neck opening 16c.

As illustrated in FIG. 5D, the minimum size of aneurysm 10b that the implant 100 can be suitable for treating can be determined by the dimensions that the braid 110 can take in the second implanted shape. The open end 114 and/or the distal fold 124b can be collapsed near a distal portion 15b of the aneurysm wall in the second implanted shape.

Figure 6A:
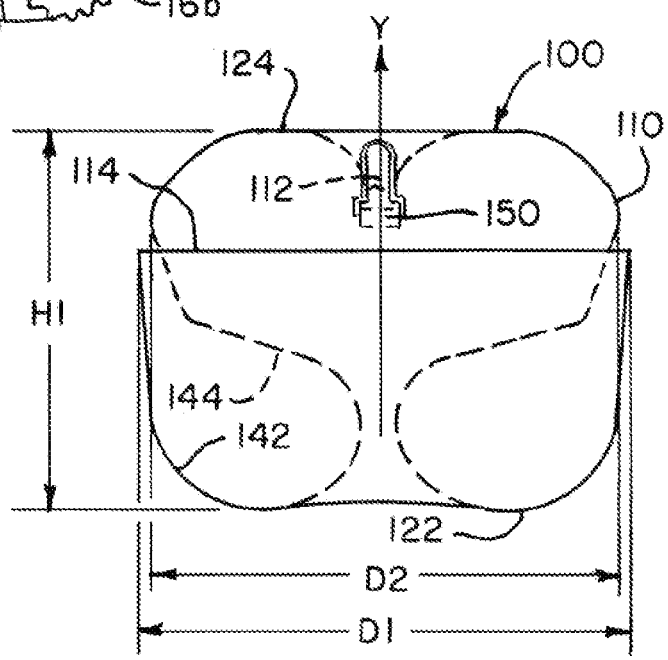
FIGS. 6A and 6B are illustrations of measurements of an example implant and an aneurysm according to aspects of the present invention.

FIG. 6A is an illustration of height HI and diameter D1, D2 measurements of an example implant 100 in a predetermined shape. In the predetermined shape, the braid 110 of the example implant 100 can be substantially radially symmetrical about vertical axis y, and therefore can have substantially circular concentric cross-sections each describable by its diameter. FIG. 6A highlights the height HI of the implant 100 in a predetermined shape measured between the inversions 122, 124, the outer diameter D1 of the outer segment 142, which corresponds to the diameter of the open end 114, and the outer diameter D2 of the middle segment D2. Although FIG. 6A illustrates only one example predetermined shape, it should be understood that the height and diameter of example implants described herein 100, 200, 300, 400 and portions thereof can be measured similarly to as illustrated in FIG. 6A.

Figure 6B:
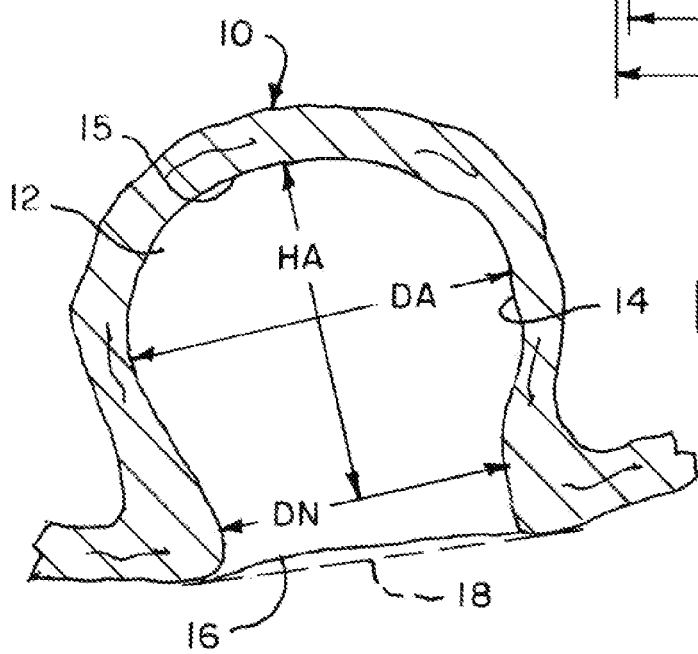

FIG. 6B is an illustration of height HA, sac diameter DA, and neck diameter DN measurements of an aneurysm 10. The location of the plane 18 defining a boundary between the aneurysm 10 and blood vessels is also illustrated.

Figure 7A:
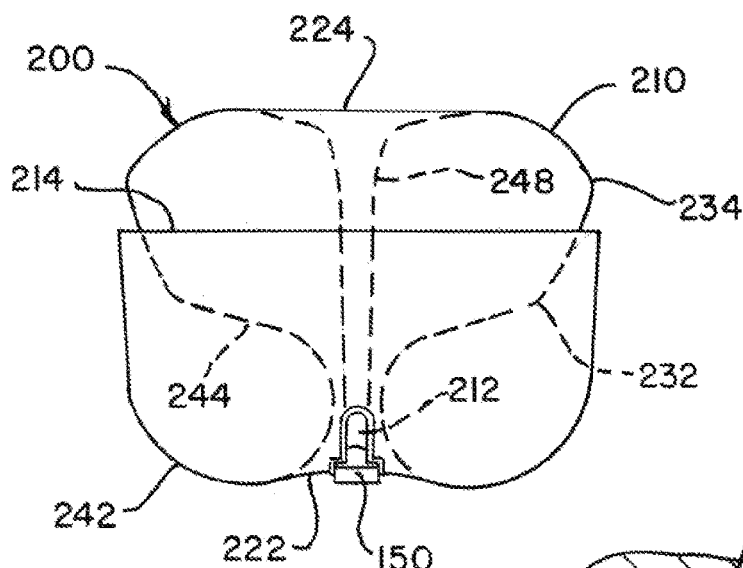
FIG. 7A is an illustration of an example implant having a tubular braid in an alternative predetermined shape according to aspects of the present invention.
Figure 7B:
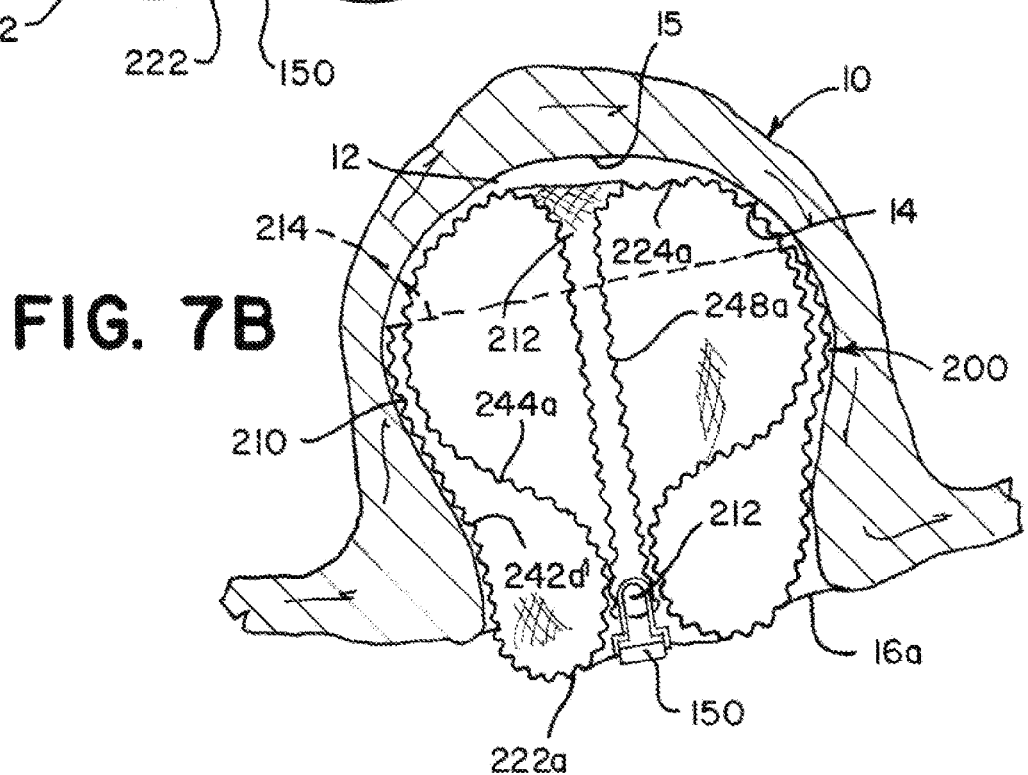
FIG. 7B is an illustration of the example implant illustrated in FIG. 7A with the tubular braid in an implanted shape according to aspects of the present invention.

FIG. 7A is an illustration of an example implant 200 having a tubular braid 210 in an alternative predetermined shape. FIG. 7B is an illustration of the example implant 200 in an aneurysm 10 with the tubular braid 210 in an implanted shape. The tubular braid 210 can have an open end 214 and a pinched end 212. The implant 200 can include a detachment feature 150 attached to the braid 210 at the pinched end 212. The braid 210 can be formed in the predetermined shape, collapsed for delivery through a microcatheter, attached to a delivery system at the detachment feature 150, and implanted in the implanted shape.

As illustrated in FIG. 7A, when in the predetermined shape, the tubular braid 210 can include two inversions 222, 224, dividing the braid 210 into three segments 242, 244, 248. In the predetermined shape, the braid 210 can have an outer segment 242 extending from the open end 214 of the braid 210 to one of the inversions 222, an inner segment 248 extending from the pinched end 212 of the braid 210 to the other of the inversions 224, and a middle segment 244 extending between the two inversions 222, 224. When in the predetermined shape, the tubular braid 210 can be substantially radially symmetrical about a central vertical axis y (see FIG. 6A). FIG. 7A illustrates a profile of each segment 242, 244, 248.

Comparing the predetermined shape of the braid 210 illustrated in FIG. 7A to that of the braid 110 illustrated in FIG. 1A, the outer segments 142, 242 and middle segments 144, 244 are respectively similar to each other, and the inner segment 248 of the braid 210 illustrated in FIG. 7A is longer than the inner segment 146 of the braid 110 illustrated in FIG. 1A. The pinched end 212 of the braid 210 in FIG. 7A is positioned near the inversion 222 adjacent the outer segment 242 rather than near the inversion 124 near the inner segment 146 as illustrated in FIG. 1A. The elongated inner segment 248 illustrated in FIG. 7A can be positioned to help the implant 200 resist compaction when implanted as illustrated in FIG. 7B.

The tubular braid 210 illustrated in FIG. 7A can be formed into the predetermined shape similar to as described in relation to FIG. 1A with some differences. The middle segment 244 need not have bends 132, 134 positioned facilitate the movement of the braid 210 into a second implanted shape. The inner segment 248 as illustrated in FIG. 7A can be made longer than that illustrated in FIG. 1A. The inner segment 248 can be shaped to have a length that is optimized to reduce the likelihood that the implant 200 can become compacted when implanted.

An implant 200 having a braid 210 having a predetermined shape as illustrated in FIG. 7A can have outer dimensions in the predetermined shape including an outer diameter and height similar to as illustrated and described in relation to FIG. 2H. The inner segment 248 of the braid 210 illustrated in FIG. 7A can have a height that is approximately equal to the height of the braid 210 in the predetermined shape.

The braid 210 can be elongated to a single layer tubular braid in a delivery shape that is sized to traverse a microcatheter. The length of the braid 210 in the delivery shape can be measured from the open end 214 to the pinched end 212. A braid 210 having a predetermined shape as illustrated in FIG. 7A and outer dimensions as illustrated and described in relation to FIG. 2H can have a length in the delivery shape that is longer compared to the length of the braid 110 illustrated in FIG. 2A. The length of the braid 210 illustrated in FIG. 7A when in the delivery shape can be longer than a braid 110 having a predetermined shape as illustrated in FIG. 1A by about the height of the braid 110, 210 in the predetermined shape. In other words, an implant 200 having a braid 210 with a predetermined shape as illustrated in FIG. 7A can have an outer diameter between about 6 mm and about 6.5 mm and a height between about 5 mm and 5.5 mm when in the predetermined shape and can be elongated to a single layer tube having a circumference collapsed to fit within a microcatheter and a length measuring between about 27 mm and 30 mm. The ratio of outermost diameter in the predetermined shape to length in the delivery shape can be between about 0.24 and about 0.2.

As illustrated in FIG. 7B, when in the implanted shape, the braid 210 can have an outer layer 242a contacting the aneurysm's wall 14, a sack 244a nested within the outer layer 242a, a proximal inversion 222a positioned at the aneurysm's neck 16, and a distal inversion 224a positioned near a distal portion 15 of the aneurysm wall 14. The detachment feature 150 and pinched end 212 of the braid 210 can be positioned near the aneurysm neck 16, near the proximal inversion 222a. The detachment feature 150 and pinched end 212 can be positioned to reduce the likelihood that the implant 200 becomes impacted.

Figure 8A:
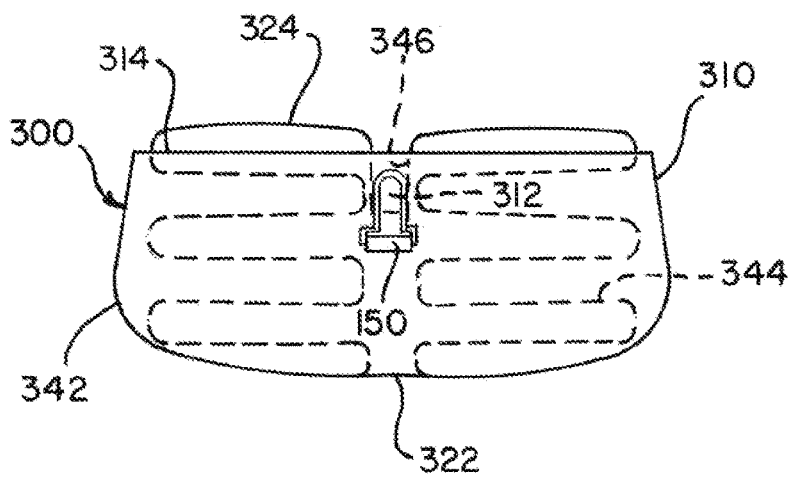
FIG. 8A is an illustration of an example implant having a tubular braid in another alternative predetermined shape according to aspects of the present invention.
Figure 8B:
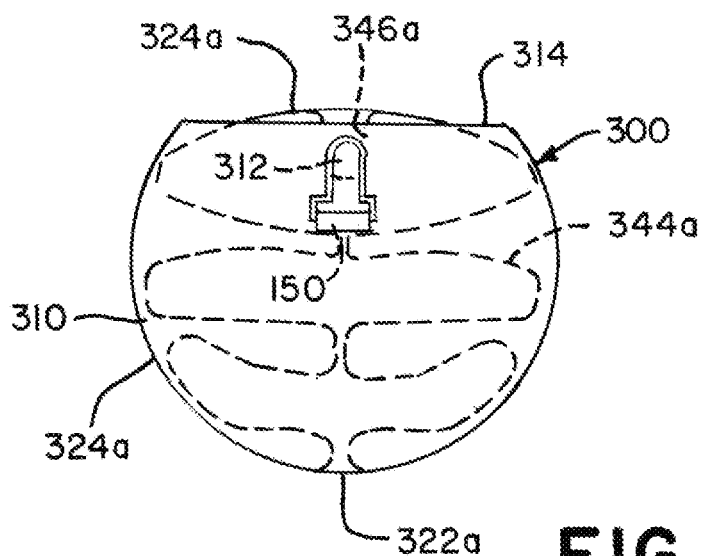
FIG. 8B is an illustration of the example implant illustrated in FIG. 8A with the tubular braid in an implanted shape according to aspects of the present invention.

FIG. 8A is an illustration of an example implant 300 having a tubular braid 310 in another alternative predetermined shape. FIG. 8B is an illustration of the example implant 300 when the tubular braid 310 in an implanted shape. The tubular braid 310 can have an open end 314 and a pinched end 312, and a detachment feature 150 can be attached to the braid 310 at the pinched end 312. The braid 310 can be formed in the predetermined shape, collapsed for delivery through a microcatheter, attached to a delivery system at the detachment feature 150, and implanted in the implanted shape.

As illustrated in FIG. 8A, when in the predetermined shape, the tubular braid 310 can include two inversions 322, 324, dividing the braid 310 into three segments 342, 344, 346. In the predetermined shape, the braid 310 can have an outer segment 342 extending from the open end 314 of the braid 310 to one of the inversions 322, an inner segment 346 extending from the pinched end 312 of the braid 310 to the other of the inversions 324, and a middle segment 344 extending between the two inversions 322, 324. When in the predetermined shape, the tubular braid 310 can be substantially radially symmetrical about a central vertical axis. FIG. 8A illustrates a profile of each segment 342, 344, 346.

Comparing the predetermined shape of the braid 310 illustrated in FIG. 8A to that of the braid 110 illustrated in FIG. 1A, the outer segments 142, 342 and inner segments 146, 346 are respectively similar to each other, and the middle segment 344 of the braid 310 illustrated in FIG. 8A has an undulating pattern rather than the "S" shape of the middle segment 144 of the braid 110 illustrated in FIG. 1A. The undulating middle segment 344 can be radially symmetrical to form a honeycomb shape. When implanted, the middle segment 344 in the undulating pattern can provide a force pattern pressing outwardly to anchor the implant 300 within an aneurysm that is different from a force pattern that could be provided by the middle segment 144 having the "S" shape illustrated in FIG. 1A. The pinched end 312 of the braid 310 in FIG. 8A can be positioned near the inversion 324 adjacent the inner segment 346 as illustrated. Alternatively, the inner segment 346 can be shaped to extend to the inversion 322 adjacent the outer segment 342 to provide a compaction resistant column.

The tubular braid 310 illustrated in FIG. 8A can be formed into the predetermined shape similar to as described in relation to FIG. 1A with some differences. The middle segment 344 can be formed to have an undulating pattern rather than an "S" shaped pattern. The middle segment 344 need not have bends positioned facilitate the movement of the braid 310 into a second implanted shape.

As illustrated in FIG. 8B, when in the implanted shape, the braid 310 can have an outer layer 342a shaped to contact an aneurysm wall, compressed extensions of an undulating middle layer 344a nested within the outer layer 342a, a proximal inversion 322a positioned to be placed an aneurysm neck, and a distal inversion 324a positioned to be placed near a distal portion of the aneurysm wall. The detachment feature 150 and pinched end 312 of the braid 310 can be positioned within the aneurysm sac, either near the distal inversion 324a as illustrated, near the proximal inversion 322a, or at a position in between. The detachment feature 150 and pinched end 312 can be positioned to reduce the likelihood that the implant 300 becomes impacted.

Figure 9A:
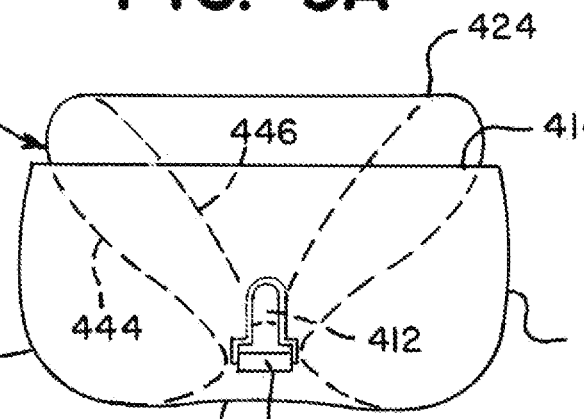
FIG. 9A is an illustration of an example implant having a tubular braid in another alternative predetermined shape according to aspects of the present invention.
Figure 9B:
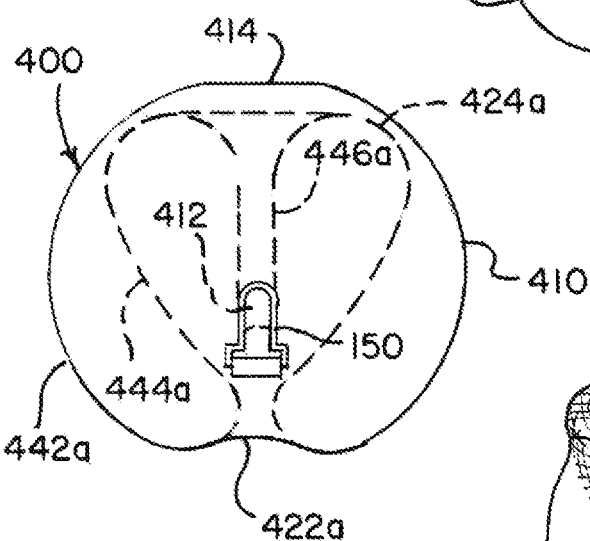
FIG. 9B is an illustration of the example implant illustrated in FIG. 9A with the tubular braid in an implanted shape according to aspects of the present invention.

FIG. 9A is an illustration of an example implant 400 having a tubular braid 410 in another alternative predetermined shape. FIG. 9B is an illustration of the example implant 400 illustrating the tubular braid 410 in an implanted shape. The tubular braid 410 can have an open end 414 and a pinched end 412. A detachment feature 150 can be attached to the braid 410 at the pinched end 412. The implant 400 can be formed in the predetermined shape, collapsed for delivery through a microcatheter, attached to a delivery system at the detachment feature 150, and implanted in the implanted shape.

As illustrated in FIG. 9A, when in the predetermined shape, the tubular braid 410 can include two inversions 422, 424, dividing the braid 410 into three segments 442, 444, 446. In the predetermined shape, the braid 410 can have an outer segment 442 extending from the open end 414 of the braid 410 to one of the inversions 422, an inner segment 446 extending from the pinched end 412 of the braid 410 to the other of the inversions 424, and a middle segment 444 extending between the two inversions 422, 424. When in the predetermined shape, the tubular braid 410 can be substantially radially symmetrical about a central vertical axis y (see FIG. 6A). FIG. 9A illustrates a profile of each segment 442, 444, 446.

Comparing the predetermined shape of the braid 410 illustrated in FIG. 9A to that of the braid 110 illustrated in FIG. 1A, the outer segments 142, 442 can be similar to each other, the middle segment 444 of the braid 410 illustrated in FIG. 9A can have a less pronounced "S" shape compared to the "S" shaped middle segment 144 illustrated in FIG. 1A, and the inner segment 446 can be conical or "V" shaped in profile with the pinch end 412 positioned near the inversion 422 adjacent the outer layer 442 rather than near the inversion 424 adjacent the inner layer 146 as illustrated in FIG. 1A. When implanted, the inner segment 446 can reshape to form a compaction resistant column.

The tubular braid 410 illustrated in FIG. 9A can be formed into the predetermined shape similar to as described in relation to FIG. 1A with some differences. The middle segment 444 illustrated in FIG. 9A can be formed to have a less pronounced "S" shape pattern compared to the "S" shaped pattern 144 illustrated in FIG. 1A. The middle segment 444 need not have bends positioned facilitate the movement of the braid 410 into a second implanted shape. The inner segment 446 can have a longer length as illustrated in FIG. 9A compared to the inner segment 146 illustrated in FIG. 1A. The inversion 424 adjacent the inner segment 446 can have a more acute curvature as illustrated in FIG. 9A compared to the corresponding inversion 124 illustrated in FIG. 1A.

As illustrated in FIG. 9B, when in the implanted shape, the braid 410 can have an outer layer 442a shaped to contact an aneurysm wall, a tulip or heart shaped sack 444a nested within the outer layer 442a, a proximal inversion 422a positioned to be placed at an aneurysm neck, a distal inversion 424a positioned to be placed near a distal portion of the aneurysm wall, and a compaction resistant column 446a extending within the sack 444a. The detachment feature 150 and pinched end 412 of the braid 410 can be positioned within the sack 444a near the proximal inversion 422a. The detachment feature 150 and pinched end 412 can be positioned to reduce the likelihood that the implant 400 becomes impacted.

Figure 10:
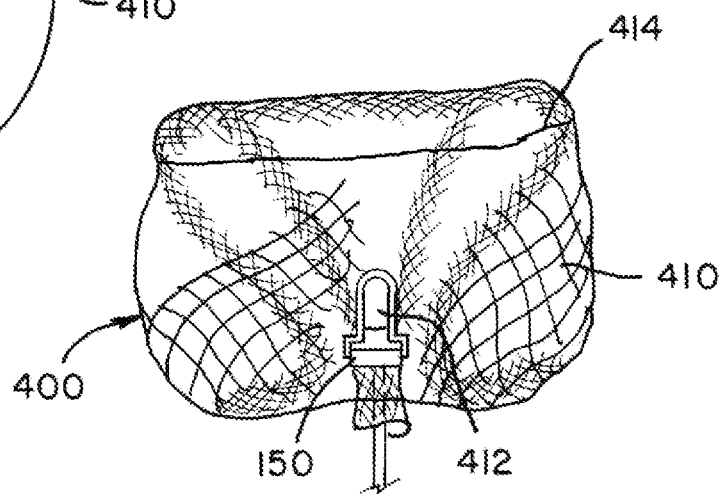
FIG. 10 is an illustration of an implant having a tubular braid in a predetermined shape similar to as illustrated in FIG. 9A according to aspects of the present invention.

FIG. 10 is an illustration of an example implant 400 having a tubular braid 410 in a predetermined shape similar to as illustrated in FIG. 9A.

Figure 11A:
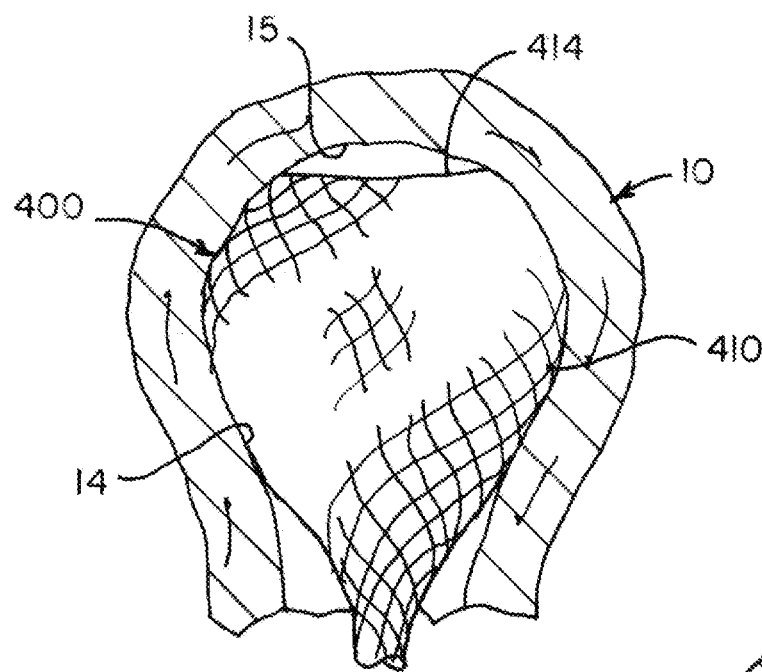
FIGS. 11A through 11E are illustrations of the implant illustrated in FIG. 10 showing the tubular braid expanding to the implanted shape similar to as illustrated in FIG. 9B according to aspects of the present invention.
Figure 11B:
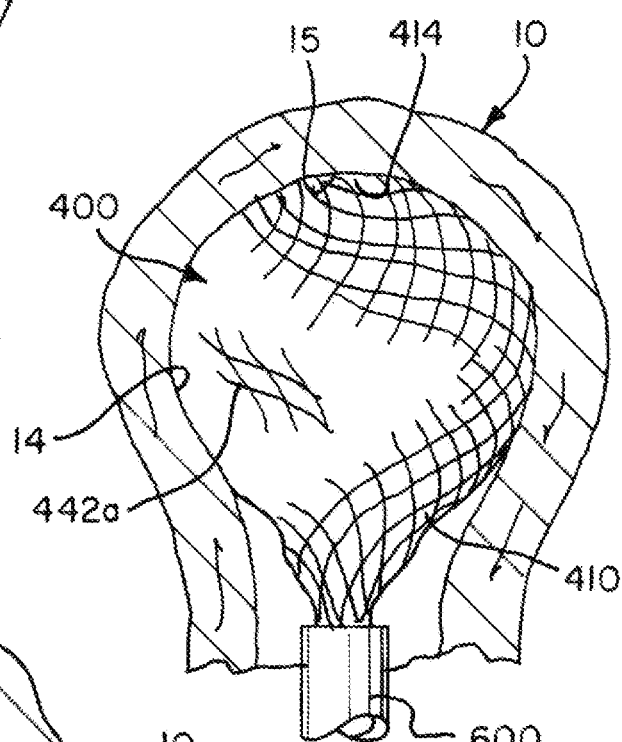
Figure 11C:
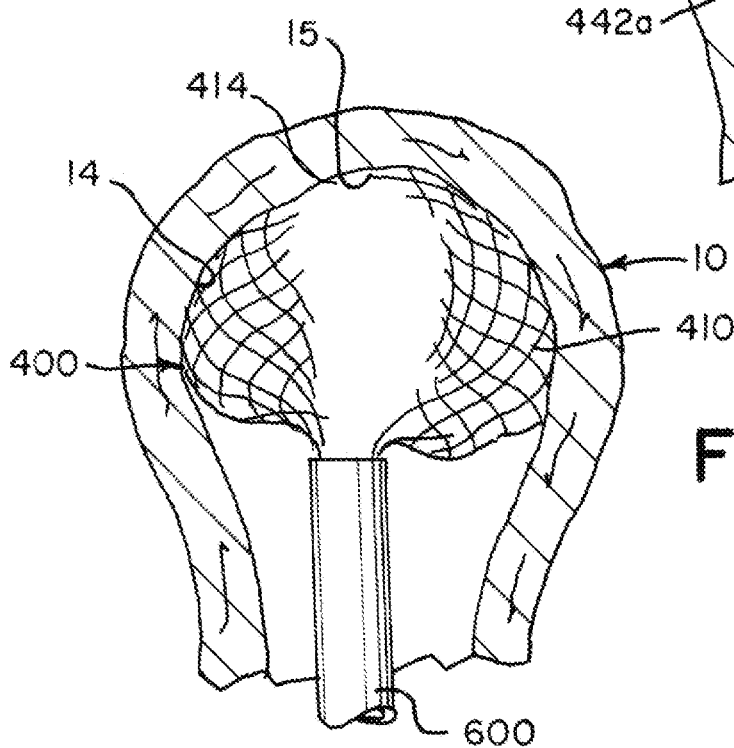
Figure 11D:
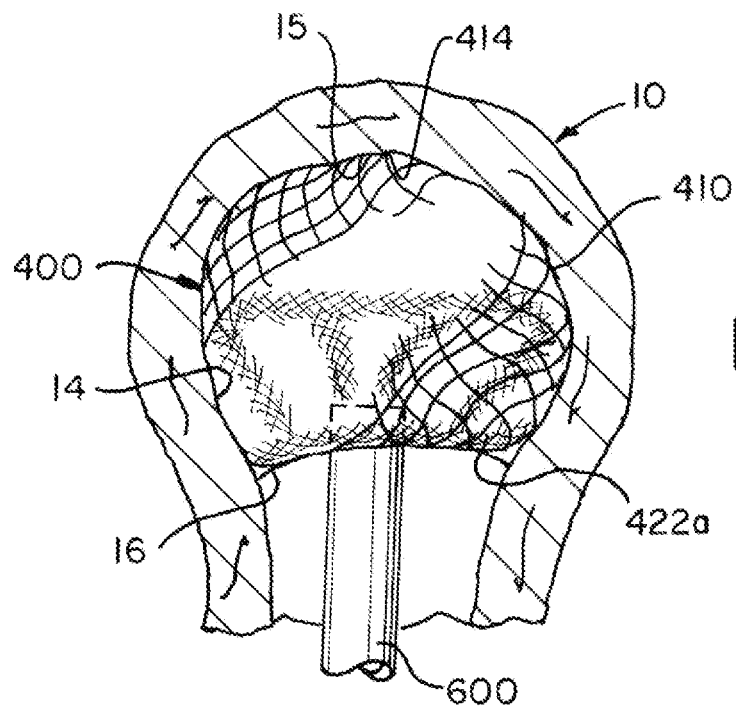
Figure 11E:
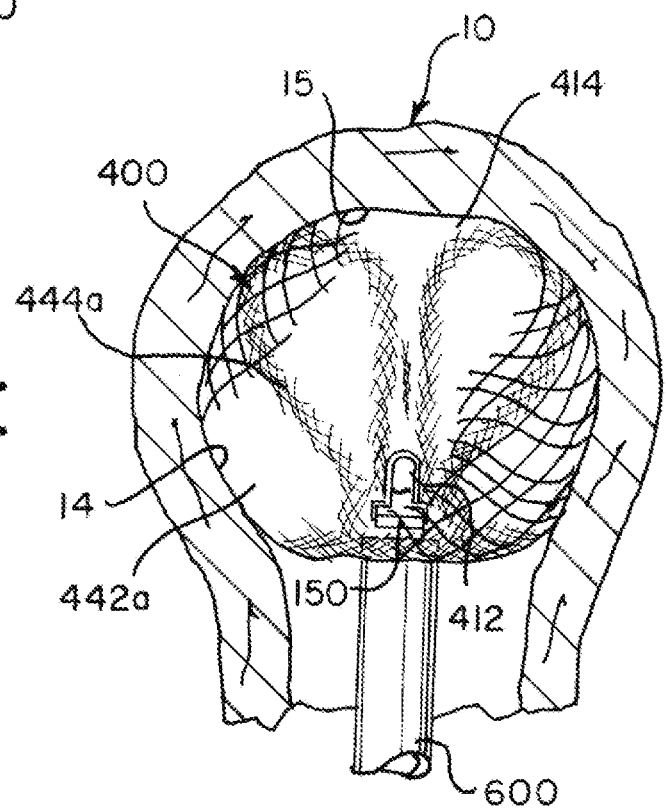

FIGS. 11A through 11E are illustrations of the example implant 400 illustrated in FIG. 10 showing the tubular braid 410 expanding to the implanted shape within a mock aneurysm 10 similar to as illustrated in FIG. 9B. As illustrated in FIG. 11A, the open end 414 can exit the microcatheter first and expand within the aneurysm 10. As illustrated in FIG. 11B, a distal portion of the braid 410 corresponding to the outer layer 442 in the predetermined shape can expand to appose the aneurysm wall 14 forming the outer layer 442a in the implanted shape. As illustrated in FIG. 11C, the braid 410 can begin to invert as the braid 410 is further pushed distally from the microcatheter 600. As illustrated in FIG. 11D, the proximal inversion 422a can be placed at the aneurysm neck 16 as the tulip shaped sack 444a expands within the outer layer 442a. As illustrated in FIG. 11E, the braid 410 can be shaped in the implanted shape within the aneurysm 10 similar to as illustrated in FIG. 9B.

Any of the implants 100, 200, 300, 400 illustrated and described herein can include one or more additional braid layers that move substantially parallel to the tubular braid 110, 210, 310, 410. The multiple layers can be stacked coaxially with each other and heat treated as a single unit into a predetermined shape. In some applications, multiple layers may be able to provide additional coverage at the aneurysm neck and additional support and conformability within the aneurysm. Each one layer of the braid can be selected with different properties with different wire counts and thickness, braid angle and diameter and wire material to potentially increase metal coverage, reduce profile (microcatheter size), facilitate deployment and reduce neck inlet channel size while providing visibility under angiogram.

Figure 12A:
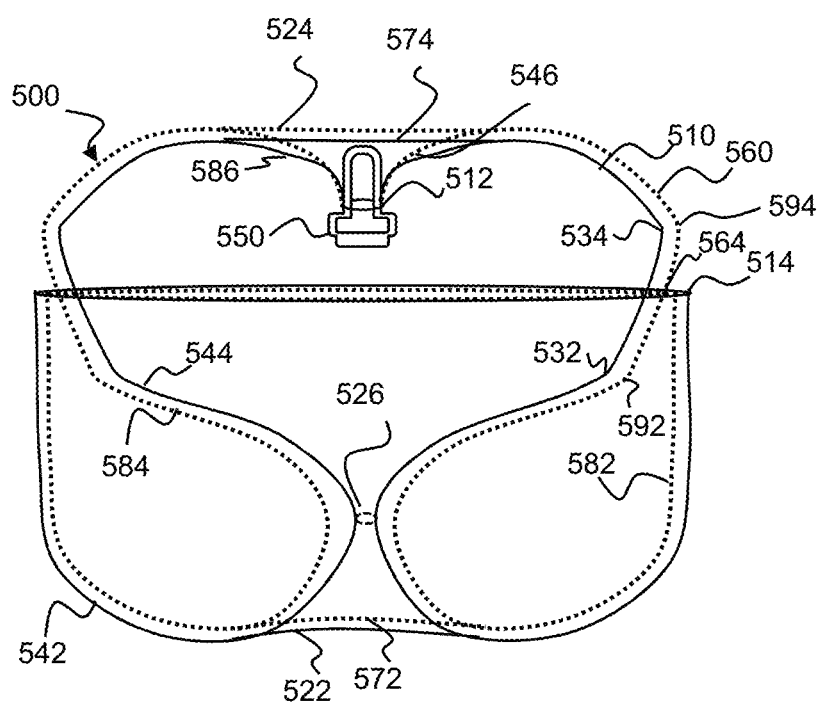
FIG. 12A is an illustration of an example implant having two layers of tubular braid in a predetermined shape according to aspects of the present invention.

FIG. 12A is a cross sectional illustration of an implant 500 including two braid layers 510, 560 in a predetermined shape similar to that illustrated in FIG. 1A. The braid layers 510, 560 are constricted at a pinched end 512 at which a detachment feature 550 can be affixed to the braid layers 510, 560. As illustrated, in the predetermined shape, each of the braid layers 510, 560 can have a respective open end 514, 564, first segment 542, 582, first inversion 522, 572, second segment 544, 584, first bend 532, 592, second bend 534, 594, second inversion 524, 574, and third segment 546, 586 similar to as described in relation to the implant 100 illustrated in FIG. 1A. For each of the two braid layers 510, 560, the third segment extends from the pinched end 512 to the second inversion 524, 574, the second segment 544, 584, extends from the second inversion 524, 574 to the first inversion and at least partially surrounds the third segment 546, 586, and the first segment extends 542, 582 from the first inversion 522, 572 and at least partially surrounds the second segment 544, 584. As illustrated, for each of the two layers, the first segment only partially surrounds the second segment. About the first inversion of each of the two layers, layer B (560) is nested within layer A (510). About the second inversion of each of the two layers, layer A is nested within layer B.

Figure 12B:
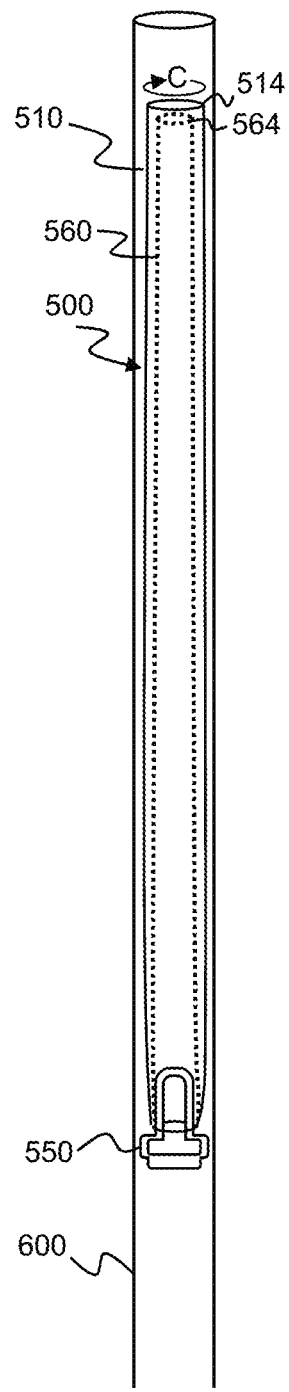
FIG. 12B is an illustration of the example implant of FIG. 12A in a catheter for delivery according to aspects of the present invention.

FIG. 12B illustrates the braid layers 510, 560 positioned within a microcatheter 600. The braid layers 510, 560 can be positioned as coaxial tubes, as illustrated, with an inner layer 560 (layer B) and outer layer 510 (layer A). Benchtop testing has demonstrated that two layers of braid can come down to a smaller braid outer circumference (C) compared to a single layer braid with the same total wire count. Implants 100, 200, 300, 400 including a single layer tubular braid 110, 210, 310, 410 preferably have a wire count of 72 wires or 96 wires. With the same total wire count, an implant 500 having two layers 510, 560 can reduce the braid profile size when collapsing into the delivery system. It can reduce the track force and also the microcatheter size, which can facilitate navigability to more challenging and distal vasculature. With the same delivery tube size, the two layers 510, 560 of braid can increase the total wire count that can fit in that size. The added wire count can decrease the porosity at the neck of the aneurysm to promote flow diversion and thrombosis at the neck to promote healing and treat ruptured aneurysms more quickly. The added wires can also facilitate the deployment of an implant in larger aneurysms in different anatomic locations.

Figure 12C:
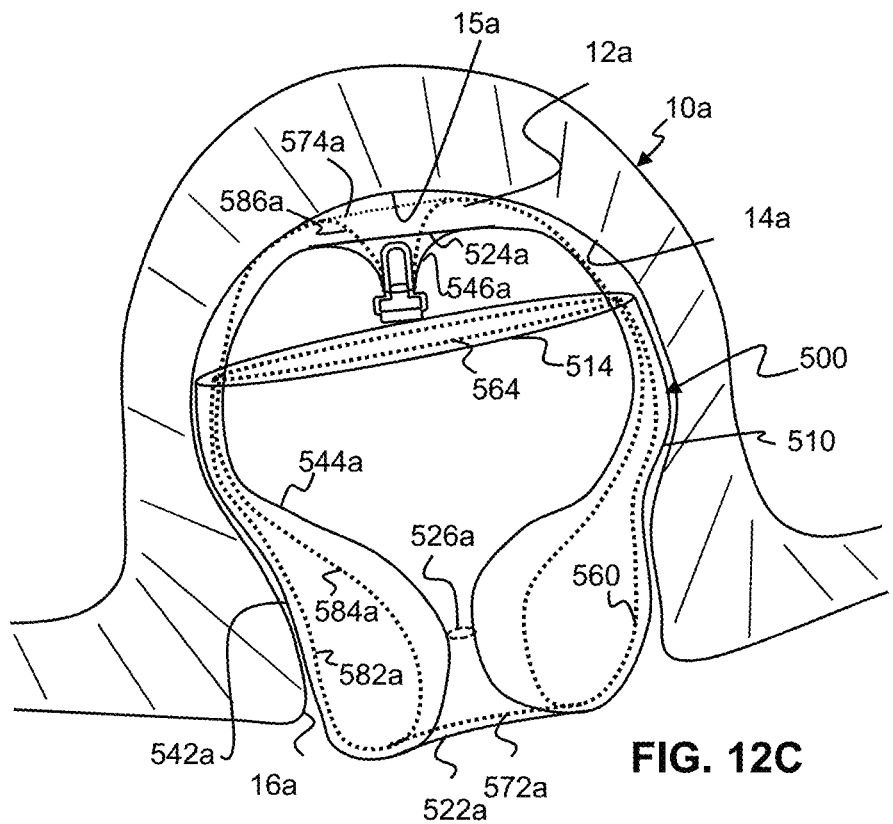
FIG. 12C is an illustration of the example implant of FIGS. 12A and 12B with the two layers of tubular braid in a first implanted shape according to aspects of the present invention.

FIG. 12C illustrates the implant 500 implanted in a larger aneurysm 10a in a first implanted shape similar to the implanted shape illustrated in FIG. 1B. The larger aneurysm 10a defines a first substantially spherical cavity having an entrance that is the neck opening 16a. As illustrated, in the first implanted shape, each of the two layers have an outer layer corresponding to the first segment of the predetermined shape and a proximal inversion corresponding to the first inversion of the predetermined shape. As illustrated, the outer layer 542a of layer A 510 is positioned to contact a cavity wall 14a of the larger aneurysm 10, the outer layer 582a of layer B 560 apposes the outer layer 542a of layer A 510, and the proximal inversion 522a, 572a of each of the two layers 510, 560 is positioned approximate the entrance 16a to the larger aneurysm 10a. As illustrated, each of the two layers 510, 560 of tubular braid comprises a sack 544a, 584a corresponding to the second segment 544, 584 of the predetermined shape. The sack 584a of layer B 560 is positioned to appose a portion of the cavity wall of the larger aneurysm 10a. The sack 544a of layer A 510 is contained within the sack 584a of layer B 560.

The two layers 510, 560 can press together to potentially perform like a stronger single layer braid which, in some applications can facilitate implant deployment in an angled aneurysm. When deployed in aneurysm, the outer segments of each of the two layers expand outwardly against the aneurysm wall to stabilize the braid against the aneurysm wall. Comparing an implant having a singular braid layer to an implant having two or more braid layers, the two implants having a similarly sized and shaped predetermined shape, the singular braid layer may require repositioning of the distal end of the catheter to facilitate inversion near the aneurysm neck while the implant having two or more braid layers may be inverted near the aneurysm neck by distal movement of the pinched end without requiring repositioning of the distal end of the catheter. The added wire counts can also increase the conformability and support at the aneurysm dome.

The two layers can also potentially increase chronic outward force to support the inner braid against the outer braid and resist compaction. As illustrated in FIG. 5A, a single layer braid 110 can provide a radial force F against the aneurysm wall 14a. Similarly, two layers 510, 560 of braid as illustrated in FIG. 12C can provide a radial force F against the aneurysm wall 14a that is greater than the single layer braid 110, all else being equal. In other words, given an implant 100 having a single layer braid 110 formed in a predetermined shape, having a total wire count, each wire having a wire circumference, and used to treat an aneurysm 10a and also given an implant 500 having two layers 510, 560 of braid, a total wire count equal to that of the single layer braid 110, an average wire circumference about equal to the wires of the single layer braid 110, and used to treat the same aneurysm or aneurysm of substantially identical size 10a, the two layers 510, 560 can provide a greater radial force F against the aneurysm wall 14a compared to the single layer 110.

Figure 12D:
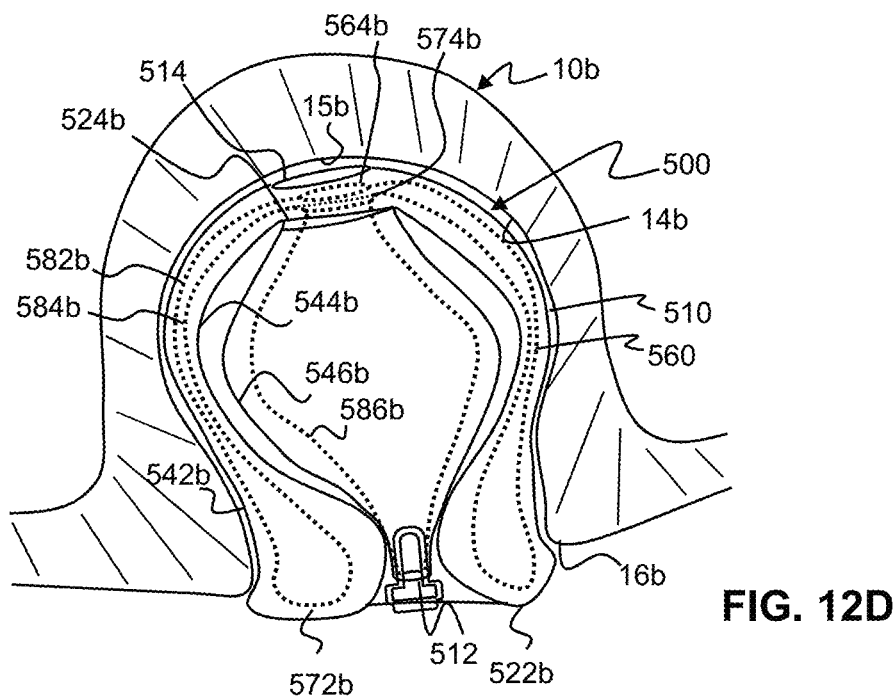
FIG. 12D is an illustration of the example implant of FIGS. 12A through 12C with the two layers of tubular braid in a second implanted shape according to aspects of the present invention.

FIG. 12D illustrates the implant 500 implanted in a smaller aneurysm 10b in a second implanted shape similar to the implanted shape illustrated in FIG. 1C. The smaller aneurysm 10b defines a second substantially spherical cavity having an entrance that is the neck opening 16b. As illustrated, in the second implanted shape, each of the two layers 510, 560 has an outer layer 542b, 582b corresponding to the first segment 542, 582 of the predetermined shape and a proximal inversion 522b, 572b corresponding to the first inversion 522, 572 of the predetermined shape. The outer layer 542b of layer A 510 contacts the cavity wall 14b of the smaller aneurysm 10b. The outer layer 582b of layer B 560 apposes the outer layer 542b of layer A 510. The proximal inversion 522b, 572b of each of the two layers is placed approximate the entrance 16b to the second substantially spherical cavity 10b. Each of the two layers of tubular braid have a middle layer 544b, 584b and inner layer 546b, 586b corresponding to the second segment 544, 584 of the predetermined shape and a fold 524b, 564b separating the middle and inner layer. The inner layer 586b of layer B 560 apposes the inner layer 546b of layer A 510 which apposes the middle layer 544b of layer A 510 which apposes the middle layer 584b of layer B 560 which apposes the outer layer 582b of layer B 560.

In the predetermined shape illustrated in FIG. 12A, each of the two layers 510, 560 of tubular braid comprises one or more bends 532, 534, 592, 594 positioned in the respective second segment 544, 584. In the second implanted shape illustrated in FIG. 12D, for each of the two layers 510, 560, the fold 524b, 574b separating the middle layer 544b, 584b and the inner layer 546b, 586b corresponds to one of the bends in the second segment of the predetermined shape.

In the first implanted shape illustrated in FIG. 12C, the pinched end 512 is suspended within the sacks 544a, 584a of layer A 510 and layer B 560. In the second implanted shape illustrated in FIG. 12D, the pinched end 512 is encircled by the proximal inversions 522a, 572a of layer A 510 and layer B 560.

In the first implanted shape illustrated in FIG. 12C, the two layers 510, 560 form an open end 514, 564 that encircles the sack 544a, 584a. In the second implanted shape illustrated in FIG. 12D, the open end 514, 564 encircles the fold 524b, 574b for each of the two layers 510, 560.

The implant 500 can be delivered and implanted following steps similar to those illustrated in FIGS. 3A through 3G. The implant 500 can be positioned within an aneurysm/spherical cavity solely via manipulation of the pinched end and positioning of the distal end of the catheter. A distal end of a catheter can be positioned near an aneurysm neck/cavity entrance. The pinched end 512 of the implant 500 can be pushed distally to push the implant 500 through at least a portion of the catheter 600. The outer layer 542a, 542b of layer A 510 can be apposed to the aneurysm wall 14. The outer layer 582a, 582b of layer B 560 can be apposed to the outer layer 542a, 542b of layer A 510. For at least the first implanted shape, a sack 584a can be formed from layer B 560 that is at least partially surrounded by the outer layers 542a, 582a of layer A and layer B and a sack 544a can be formed from layer A 510 that is at least partially surrounded by the outer layers of layer A and layer B and contained within the sack of layer B. The pinched end can be disengaged while two layers 510, 560 each retain their respective sacks 544a, 584a to leave the implant 500 implanted in the first implanted shape. For at least the second implanted shape, the second segment 544, 584 of each of the two layers 510, 560 in the second implanted shape can be folded to form the inner layer 546b, 586b and middle layer 544b, 584b separated by the fold 524b, 574b such that that the inner layer 586b of layer B 560 apposes the inner layer 546b of layer A 510 which apposes the middle layer 544b of layer A 510 which apposes the middle 584b layer of layer B 560 which apposes the outer layer 582b of layer B 560.

By virtue of having two implanted shapes, similar to the implant 100 illustrated in FIGS. 1A through 1C, the implant 500 illustrated in FIGS. 12A through 12D can be suitable (via appropriate jurisdictional requirements for medical devices) for treating a first aneurysm having a first diameter measuring about 4 mm and a first height measuring about 6 mm, a second aneurysm comprising a second diameter measuring about 5 mm and a second height measuring about 8 mm, and a third aneurysm comprising a third diameter measuring about 6 mm and a third height measuring about 6 mm. Also, by virtue of having two implanted shapes, similar to the implant 100 illustrated in FIGS. 1A through 1C, the implant 500 illustrated in FIGS. 12A through 12D can be suitable for treating aneurysms within a continuum of aneurysm sizes, the continuum bounded by and including diameters between about 4 mm and about 5 mm and heights between about 6 mm and about 8 mm.

Figure 13:
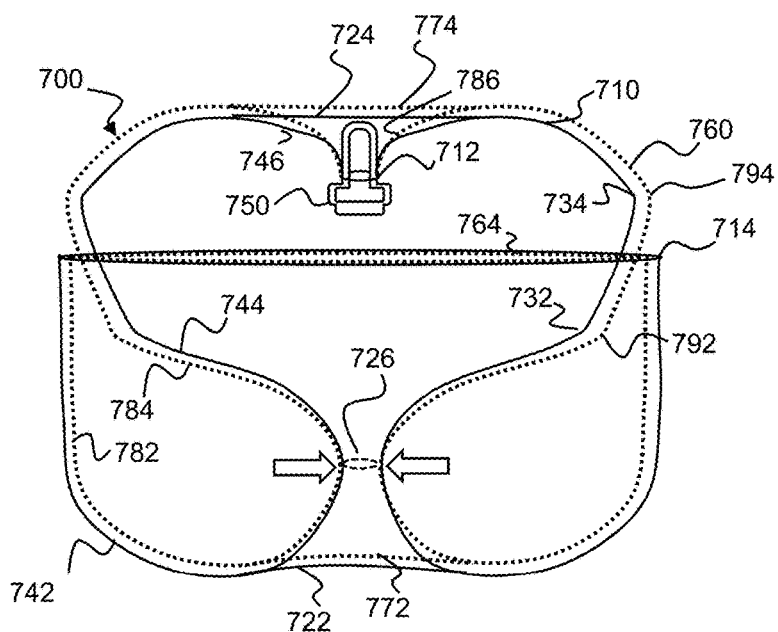
FIG. 13 is an illustration of an example implant having two layers of tubular braid in a predetermined shape similar to that of FIG. 12A and having an alternative braid configuration according to aspects of the present invention.

FIG. 13 illustrates a cross section of another implant 700 having two braid layers 710, 760 in a predetermined shape. The implant 700 is formed to the predetermined shape similar to the implants 100, 500 illustrated in FIGS. 1A and 12A. The implant 700 illustrated in FIG. 13 differs primarily from the implant 500 illustrated in FIG. 12A in the area of the neck channel 526, 716.

Including two or more braid layers can potentially decrease the inner neck channel size for devices made of Nitinol-platinum wire woven braid. In other words, for a substantially identical process of achieving a predetermined shape, the neck channel opening 526, 726 of an implant 500, 700 having two layers 510, 710, 560, 760 can be smaller than the neck channel opening 126 of an implant 100 having a single braid layer 110. Similarly, when implanted, the neck channel opening 526a illustrated in FIG. 12C can be smaller than the neck channel opening 126a illustrated in FIG. 1B and further smaller for neck channel 726 in FIG. 13. A neck channel having a large opening can allow constant blood flow to reach the aneurysm neck and slow down healing. Platinum wires added to a braid generally make the braided portion of the respective implant visible under angiogram. However, because the platinum wire does not retain its shape as well as the nitinol wire after heat treatment, when deployed, a nitinol-platinum braid device is expected to have a bigger neck channel opening compared to an all nitinol braid (where the nitinol-platinum braid and the all nitinol braid have substantially identical predetermined shapes).

Depending on the specific needs and braid properties, in an implant including two or more braid layers, an all nitinol braid can be used in combination with a nitinol-platinum braid such that the nitinol-platinum braid facilitates visualization of the braided portion of the braid and the all nitinol braid facilitates movement of the braid layers to the predetermined shape. The all nitinol braid can either be used as the inside or outside braid to reduce the inner channel size when fabricated with nitinol-platinum braid. FIG. 12A illustrates an implant 500 having an all nitinol braid is positioned outside during delivery, layer A 510, and a nitinol-platinum braid positioned on the inside during delivery, layer B 560. When deployed, the nitinol braid 510 can create a small neck inner channel 526a and can cover a larger channel of a nitinol-platinum braid 560. FIG. 13 illustrates an implant 700 having an all nitinol braid positioned as layer B 760 and a nitinol-platinum braid positioned as layer A 710. When deployed, the nitinol braid 760 can cinch down on the nitinol-platinum braid 710 and create a double layered neck channel 726 that is smaller than the opening of the neck channel 126 with a nitinol-platinum braid alone 110 as illustrated in FIG. 1A.

Referring to FIG. 13, the braid layers 710, 760 are constricted at a pinched end 712 at which a detachment feature 750 can be affixed to the braid layers 710, 760. As illustrated, in the predetermined shape, each of the braid layers 710, 760 can have a respective open end 714, 764, first segment 742, 782, first inversion 722, 772, second segment 744, 784, first bend 732, 792, second bend 734, 794, second inversion 724, 774, and third segment 746, 786 similar to as described in relation to the implant 100 illustrated in FIGS. 1A and 1n relation to the implant 500 illustrated in FIG. 12A. For each of the two braid layers 710, 760, the third segment 746, 786 extends from the pinched end 712 to the second inversion 724, 774, the second segment 744, 784, extends from the second inversion 724, 774 to the first inversion and at least partially surrounds the third segment 746, 786, and the first segment 742, 782 extends from the first inversion 722, 772 and at least partially surrounds the second segment 744, 784. As illustrated, for each of the two layers 710, 760, the first segment 742, 782 only partially surrounds the respective second segment 744, 784. About the first inversion 722, 772 of each of the two layers, layer B 760 is nested within layer A 710. About the second inversion 724, 774 of each of the two layers, layer A 710 is nested within layer B 760.

The implant 700 can be delivered through a catheter 600 similar to as illustrated in FIG. 12B. The implant can be positioned through steps similar to as illustrated in FIGS. 3A through 3G and described in relation to FIGS. 12A through 12D. The implant 700 can be implanted in two distinct implanted shapes similar to as illustrated in FIGS. 12C and 12D.

Figure 14:
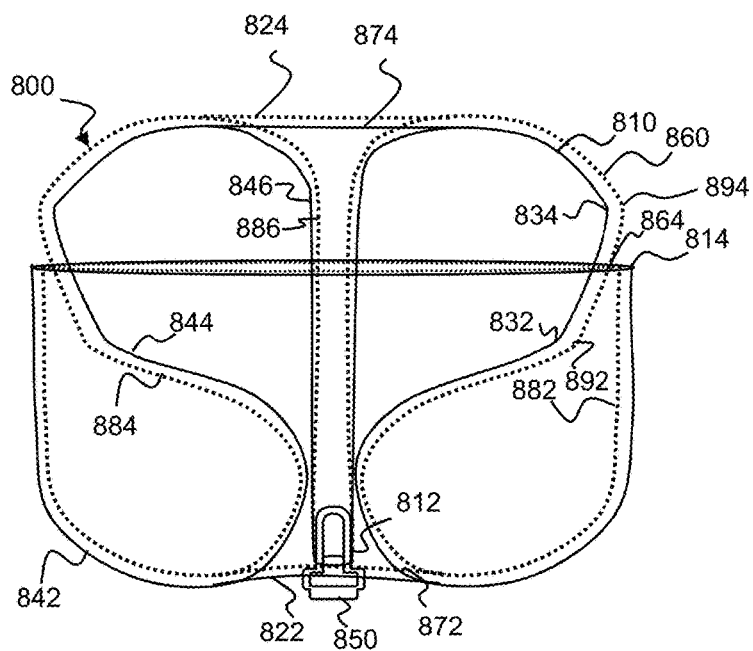
FIG. 14 is an illustration of an example implant having two layers of tubular braid in an alternative predetermined shape according to aspects of the present invention.

FIG. 14 illustrates a cross section of another implant 800 having two braid layers 810, 860 in a predetermined shape. The implant 800 has a predetermined shape similar to that illustrated in FIG. 7A, a difference being the implant 800 illustrated in FIG. 14 has two tubular braid layers while the implant illustrated in FIG. 7A has one tubular braid. The implant 800 illustrated in FIG. 14 also has a predetermined shape similar to that illustrated in FIG. 12A, a difference being the implant 800 illustrated in FIG. 14 includes a dual layer compaction resistant post formed from inner segments 846, 886 of the braid 810.

The braid layers 810, 860 are constricted at a pinched end 812 at which a detachment feature 850 can be affixed to the braid layers 810, 860. As illustrated, in the predetermined shape, each of the braid layers 810, 860 can have a respective open end 814, 864, first segment 842, 882, first inversion 822, 872, second segment 844, 884, first bend 832, 892, second bend 834, 894, second inversion 824, 874, and third segment 846, 886 similar to as described in relation to the implant 100 illustrated in FIGS. 1A and 1n relation to the implant 500 illustrated in FIG. 12A. For each of the two braid layers 810, 860, the third segment 846, 886 extends from the pinched end 812 to the second inversion 824, 874, the second segment 844, 884, extends from the second inversion 824, 874 to the first inversion and at least partially surrounds the third segment 846, 886, and the first segment 842, 882 extends from the first inversion 822, 872 and at least partially surrounds the second segment 844, 884. As illustrated, for each of the two layers 810, 860, the first segment 842, 882 only partially surrounds the respective second segment 844, 884. About the first inversion 822, 872 of each of the two layers, layer B 860 is nested within layer A 810. About the second inversion 824, 874 of each of the two layers, layer A 810 is nested within layer B 860.

The two layers 810, 860 of tubular braid can be stabilized in an implanted shape based on the predetermined shape illustrated in FIG. 14 when the braid layers 810, 860 are constrained by a substantially spherical cavity such as the interior of an aneurysm. In the implanted shape, layer A 810 has an outer layer corresponding to the first segment 842 that apposes the cavity wall of the substantially spherical cavity/aneurysm, layer B 760 has and outer layer corresponding to the first segment 882 that apposes to the outer layer of layer A 810, layer B 860 has an inner sack corresponding to the middle segment 884 that apposes to the outer layer of layer B 810, layer A 810 has an inner sack corresponding to the middle segment 844 positioned within the inner sack of layer B 860, for each of the two layers 810, 860, a proximal inversion corresponding to the first inversion 822, 872 is positioned approximate an entrance to the substantially spherical cavity/aneurysm neck, for each of the two layers 810, 860, a distal inversion corresponding to the second inversion 824, 874 is positioned approximate a distal portion of the cavity wall, and each of the two layers 810, 860 has a post corresponding to the third segment 846, 886, the post extending centrally within the inner sack and along a majority of a length between the distal inversion and the proximal inversion such that the post of layer B is positioned within the post of layer A.

The implant 800 can be delivered and implanted similar to as described in relation to the first implanted shape of the implant 500 illustrated in FIGS. 12A through 12C with a difference being that the pinched end 812 of the implant 800 illustrated in FIG. 15 can be positioned near the aneurysm neck, a tubular segment of layer A corresponding to the third segment 846 can be extended within the sack of layer A 810 and the sack of layer B 860 to terminate at the pinched end 812, and a tubular segment of layer B 860 corresponding to the third segment 886 can be extended within the tubular segment of layer A 810 to terminate at the pinched end 812.

Although not illustrated, the implants 300, 400 illustrated in FIGS. 8A-B, 9A-B, 10, and 11A-E can alternatively include two or more braid layers according to the principles illustrated and described in relation to FIGS. 12A-D, 13, and 14. Further, each implant 100, 200, 300, 400, 500, 700, 800 can include a total of two, three, four, or five braid layers.

Figure 15A:
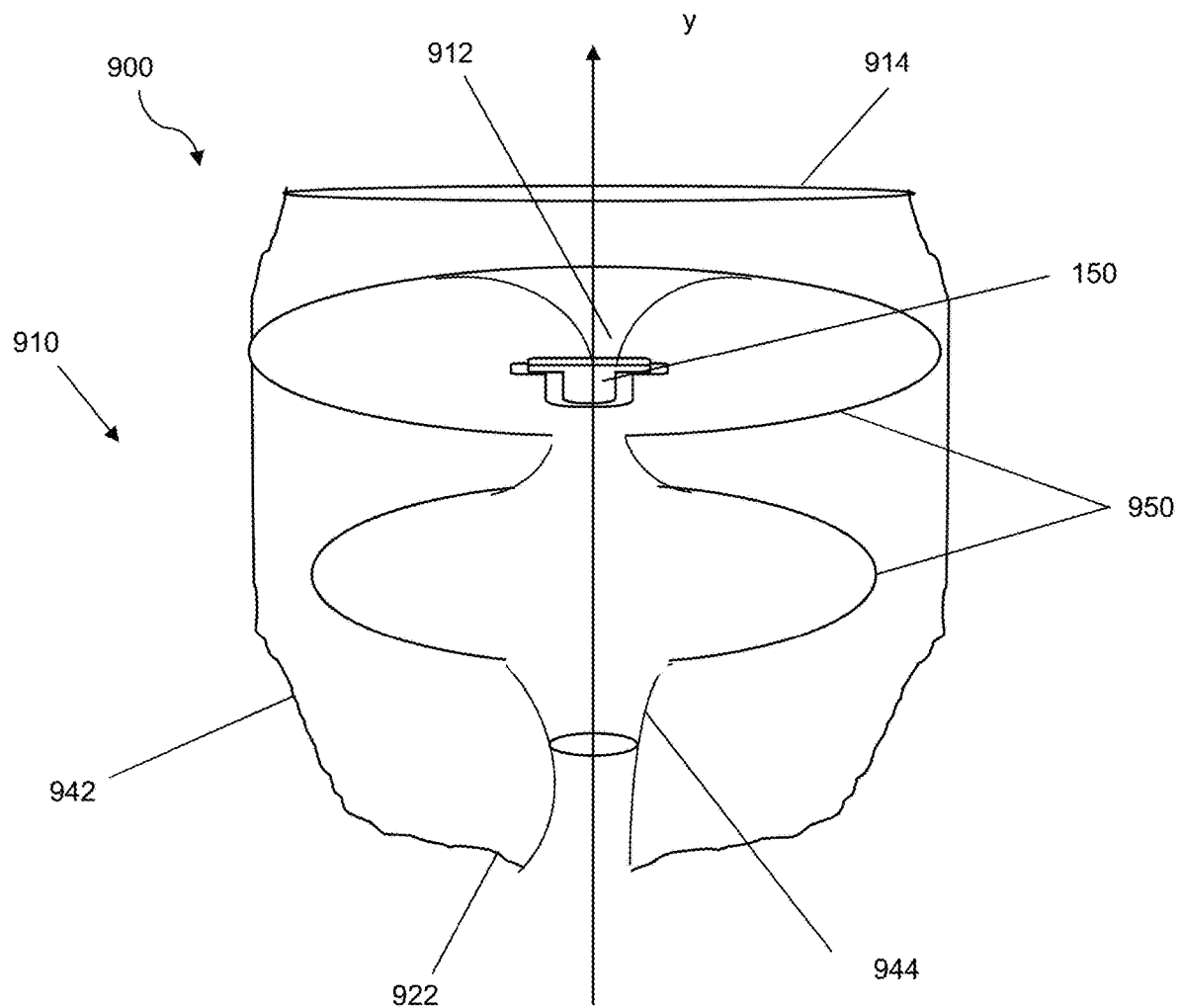
Figure 15C:
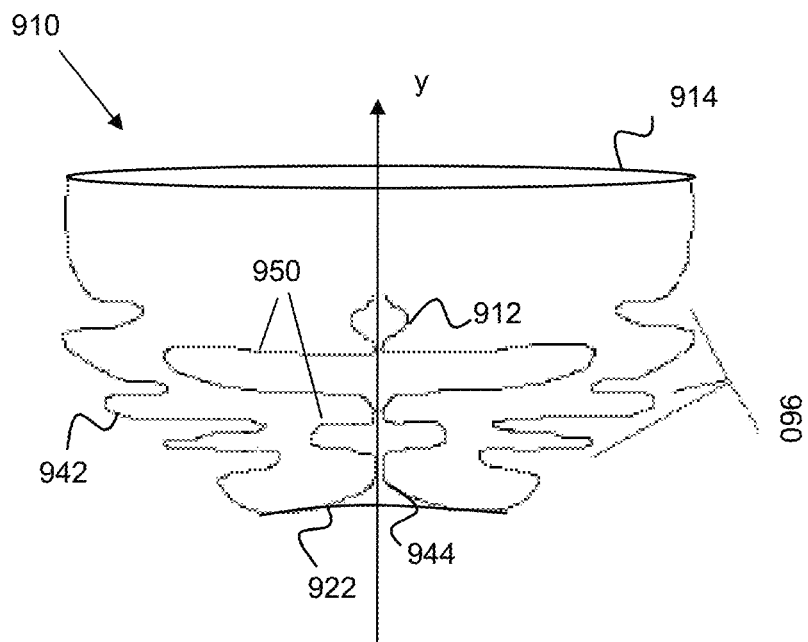

FIGS. 15A to 15C are illustrations of an example tubular implant 900 that can have a predetermined shape. The implant 900 can treat a range of aneurysm sizes. The implant 900 can include a tubular braid 910 having an open end 914 and a pinched end 912. The predetermined shape is the expanded shape of the tubular braid 910 when the braid 910 is not confined by a delivery catheter. When implanted, the braid 910 is in an implanted shape, which is based at least in part on the predetermined shape and the anatomy of the aneurysm 10. The tubular braid 910 can be composed of one or more wires.

The implant 900 can include a connection and detachment feature 150 attached to the braid 910 at the pinched end 912. The pinched end 912 can include a marker band and/or soldered point with visibility, and/or the connection feature 150 can include radiopaque material. The tubular braid 910 can be formed in a predetermined shape (FIGS. 15A to 15C), collapsed for delivery through a microcatheter, attached to a delivery system at the connection feature 150, and implanted in an implanted shape such as the ones shown in FIGS. 16A and 16B.

Referring to FIGS. 15A through 15C, when in a predetermined shape, the tubular braid 910 can include an inversion 922, a pinched end 912, and an open end 914. The tubular braid can include two segments, 942 and 944. The first segment 942 can extend from the open end 914 of the tubular braid 910 to a proximal inversion 922. The second segment 944 can be at least partially surrounded by the open end 914 and can extend from the proximal inversion 922 to the pinched end 912. The second segment, as shown in FIGS. 15A to 15C, can also include at least one corrugated fold 950. The first segment, as shown in FIGS. 15B and 15C, can also include at least one corrugated fold 960. The corrugated folds 950, 960 can be configured to assist in anchoring the device when in an implanted shape (e.g. FIGS. 16A and 16B) within an aneurysm 10. The corrugated folds can act in a similar manner to stent struts to help the tubular braid 910 hold its predetermined or implanted shape.

When in a predetermined shape, the tubular braid 910 can be substantially radially symmetrical about a central vertical axis. The tubular braid can be formed into a predetermined shape by inverting the braid inwardly to separate the second segment 944 from the first segment 942. The tubular braid 910 can include memory shape material that can be heat set to the predetermined shape. This heat-set material can be utilized to form one or more corrugations 950, 960 in the first and/or second segments 942, 944.

Figure 16A:
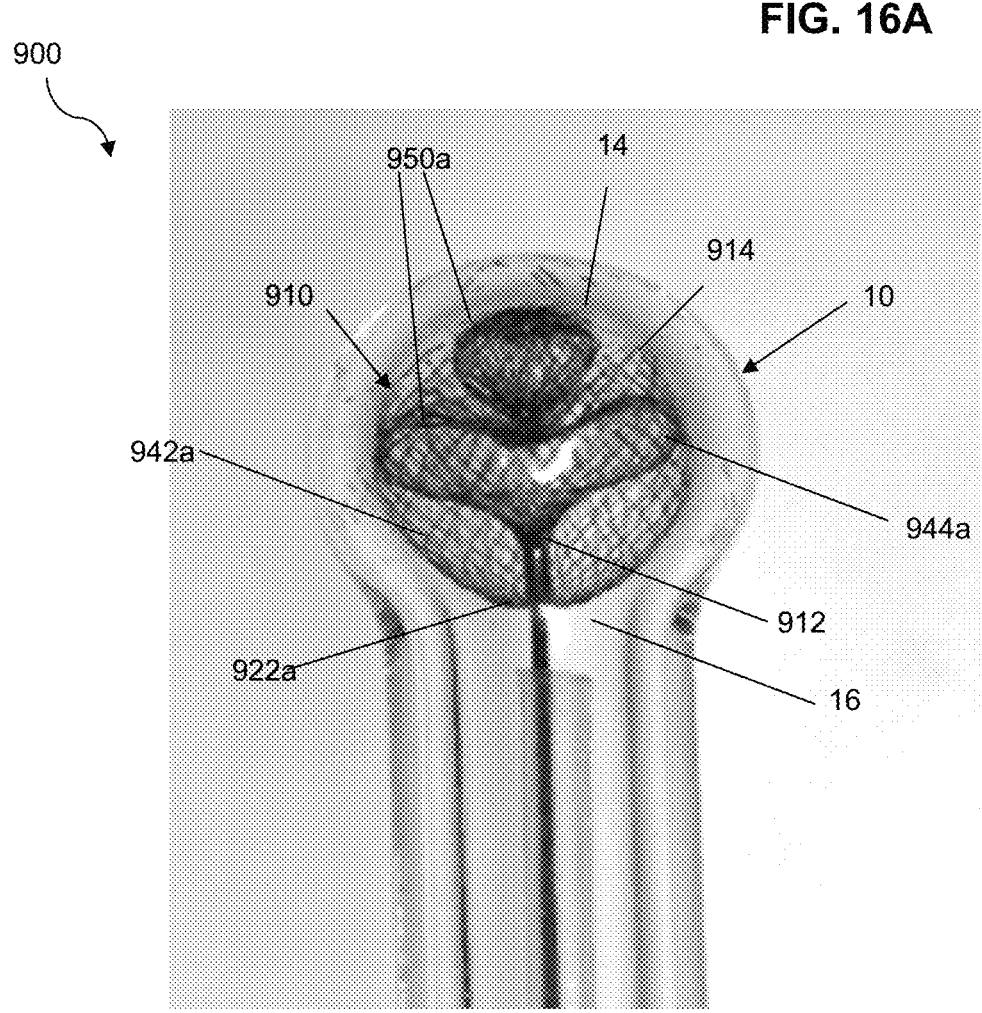
FIGS. 16A and 16B illustrate example implants with one or more corrugated folds in an implanted shape according to aspects of the present invention.
Figure 16B:
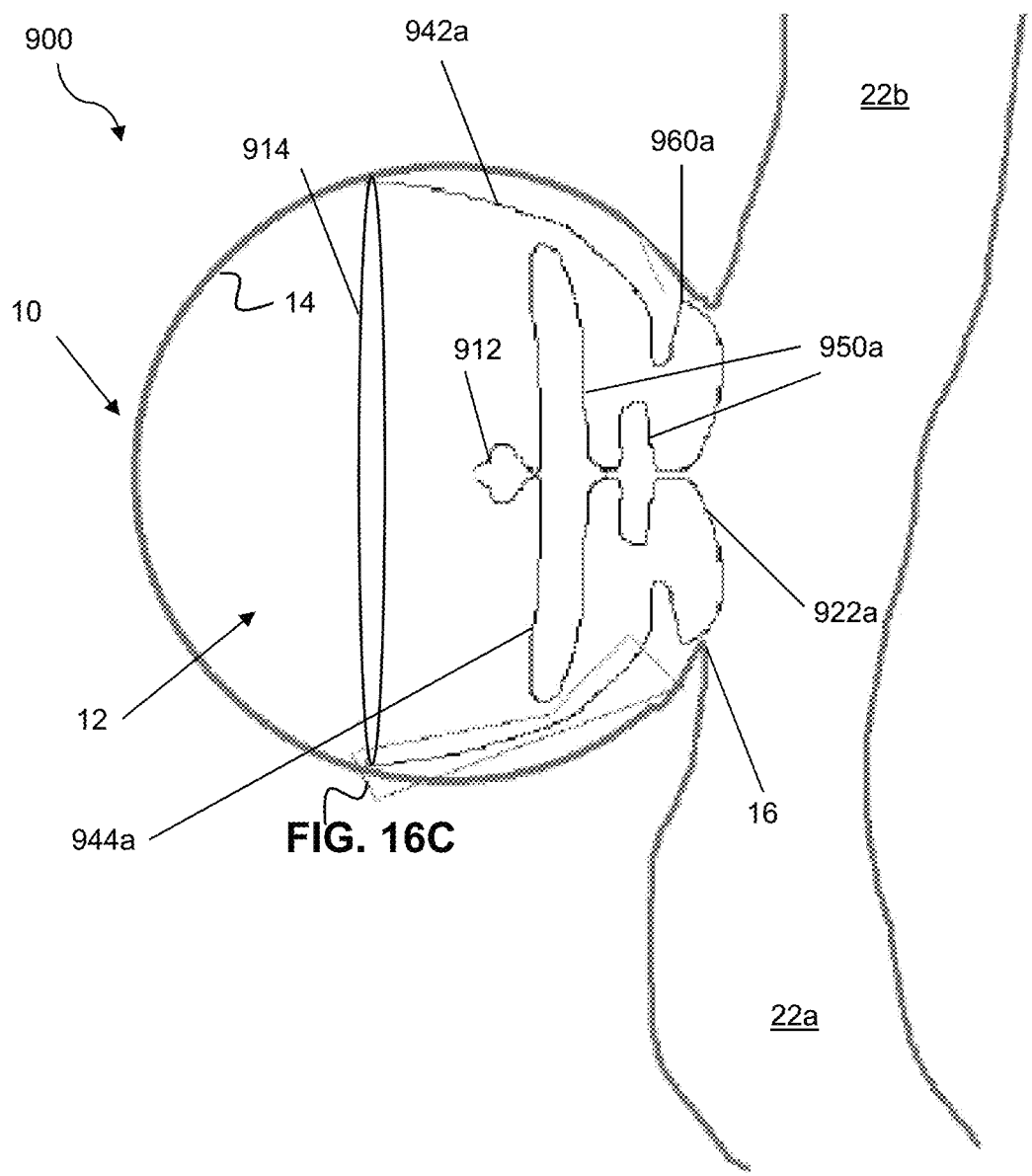
Figure 16C:
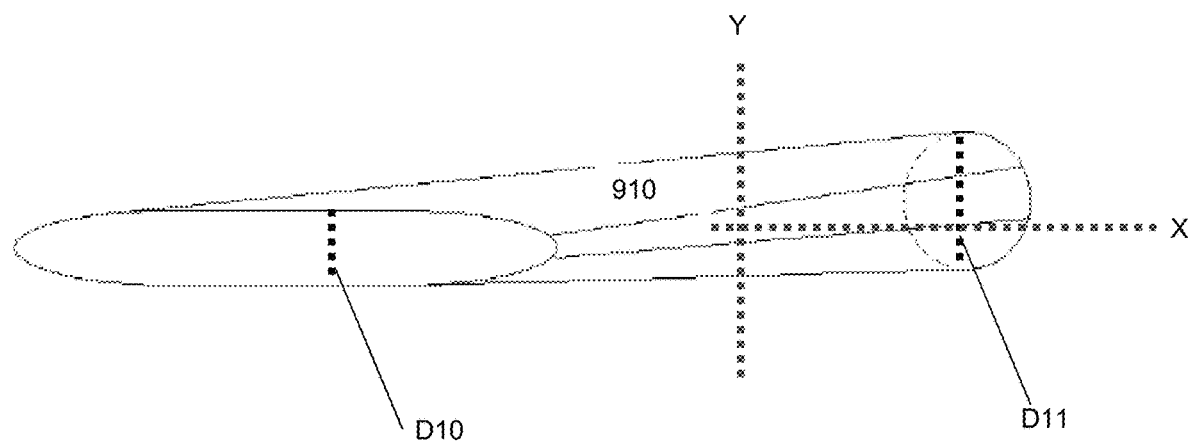
FIG. 16C illustrates a cross sectional view of a compressed corrugated fold according to aspects of the present invention.

As illustrated in FIG. 16C, the one or more wires of the tubular braid 910 making up the corrugated folds 950, 960 can be compressed or flattened along a vertical axis, resulting in a smaller wire diameter along the vertical axis of the corrugated fold 950, 960 relative to the non-compressed portions of the tubular braid 910. The compressed portions of the wires making up the corrugated folds 950, 960 can also have a different cross-sectional shape relative to non-compressed portions of wire in the tubular braid 910. For instance, the non-compressed portions of wire can be circular, while the compressed portions can be ellipsoid in shape. Flattening the one or more wires making up the corrugated folds 950, 960 can make these portions of the tubular braid 910 more rigid, thereby assisting in maintaining the shape of the tubular braid 910 and anchoring it within an aneurysm. By compressing the wires, the wires are no longer able to bend or flex equally in all directions. Preferably, flattening the one or more wires making up the corrugated folds 950, 960 can make the wires bendable in two opposite directions. Therefore, portions of the braid 910 constructed with flattened wires, such as corrugated folds 950, 960 can be more resistant to bending relative to non-flattened wires in the remainder of the braid.

The tubular braid 910 can be deformed for delivery through a catheter and can self-expand to an implanted shape (e.g., FIGS. 16A and 16B) that is based on a predetermined shape and confined by the anatomy of the aneurysm in which it is implanted. When the tubular braid 910 is in the predetermined shape, at least one corrugated fold 950 in the second segment 944 can appose the first segment 942 or a corrugated fold 960 in the first segment 942, thereby exerting an outwardly radial force on the first segment 942.

The tubular braid 910 in the implanted shape can be radially or vertically compressed or extended compared to the predetermined shape. Compressing the tubular braid 910 can cause the folds in the inner layer 950a to provide a force against the first segment 942a and/or a corrugated fold in the first segment 960a. This compression can also cause the corrugated folds 960a in the first segment 942a to apply a radial force against the aneurysm wall 14.

FIG. 16A illustrates the predetermined shape in FIG. 15A as implanted into an aneurysm. In the implanted shape in FIG. 16A, the braid 910 can have an outer layer 942a corresponding to the first segment 942 of the predetermined shape and positioned to contact an aneurysm wall 14 of the aneurysm 10. A proximal inversion 922a can correspond to the proximal inversion 922 of the predetermined shape and positioned to be placed approximate a neck 16 of an aneurysm 10. An inner layer 944a can correspond to the second segment 944 of the predetermined shape. The tubular braid 910 can have at least one corrugated fold 950a in the inner layer corresponding to the at least one corrugated fold in the second segment of the predetermined shape.

When the tubular braid 910 is in the implanted shape within an aneurysm 10, at least one corrugated fold in the inner layer 950a can appose at least a portion of the outer layer 942a, thereby exerting an outwardly radial force on the outer layer 942a to anchor the implant 900 within the aneurysm 10. The wire of the tubular braid 910 comprising the corrugated folds 950a in the inner layer 946a can be flattened as described in FIGS. 15A to 15C and shown in FIG. 16C to increase the rigidly of the corrugations and assist with anchoring the tubular braid 910 within the aneurysm 10.

In FIG. 16B, the predetermined shape of FIG. 15B is in the implanted shape. In this implanted shape, the tubular braid 910 can also have at least one corrugated fold in the outer layer 960a corresponding to the at least one corrugated fold in the first segment of the predetermined shape. The corrugated folds of the inner layer 950a can be formed in a position such that they appose corrugated folds in the outer layer 960a when in the implanted shape. The corrugated folds of the outer layer 960a provide an outwardly radial force in a plane defining a boundary between the aneurysm 10 and a blood vessel 22a, 22b, the force sufficient to appose the outer layer 942a to walls 14 of the aneurysm 10 and anchor the implant 900 within the aneurysm. Further, as illustrated in FIG. 16B, the wire of the tubular braid 910 comprising the corrugated folds 960a in the outer layer 942a can also be flattened as shown in FIG. 16C to increase the rigidly of the corrugations and assist with anchoring the tubular braid 910 within the aneurysm 10.

A method for forming an implant 900 to treat an aneurysm can include positioning a distal end of a catheter approximate a neck 16 of an aneurysm 10, pushing a pinched end 912 of a tubular braid 910 having one or more wires and an open end 914 distally through at least a portion of the catheter, positioning the open end 914 within a sac 12 of the aneurysm 10; and deploying the tubular braid 910 to an implanted shape within the aneurysm based upon a predetermined shape. The implant 900 can be deployed to an implanted shape within the aneurysm based upon a predetermined shape by inverting the tubular braid 910 to form a proximal inversion 922a by moving the open end 914 over at least a portion of the braid 910, shaping an outer layer 942a of the tubular braid 910 extending between the open end 914 and the proximal inversion 922a, and shaping an inner layer of the tubular braid 944a extending between the proximal inversion 922a and the pinched end 912, wherein at least one corrugated fold 950a is located within the inner layer 944a.

The method can further include positioning the implant within the aneurysm sac solely via manipulation of the pinched end and via positioning of the distal end of the catheter. The outer layer can also include at least one corrugated fold 960a within the outer layer 942a. When implanted, at least one corrugated fold 950a within the inner layer 944a can provide an outwardly radial force against the outer layer 942a, against a corrugated fold in the outer layer 960a in a plane defining a boundary between the aneurysm 10 and a blood vessel 22, or both. The force can be sufficient to appose the outer layer 942a to walls 14 of the aneurysm 10. In a similar manner, the corrugated folds 960a of the outer layer 942a can provide an outwardly radial force in a plane defining a boundary between the aneurysm 10 and a blood vessel 22, the force sufficient to appose the outer layer 942a to walls 14 of the aneurysm 10.

The wire of the tubular braid 910 comprising the at least one corrugated folds can be compressed along a vertical axis such that the diameter of the corrugated fold along the axis is lesser than the diameter of the uncompressed portions of the tubular braid 910. This compression can increase the rigidity of the at least one corrugated fold relative to the rest of the braid.

Some examples presented herein generally include a braided implant that can secure within an aneurysm sac and occlude a majority of the aneurysm's neck. The implant can include a tubular braid that can be set into a predetermined shape, compressed for delivery through a microcatheter, and implanted in at least one implanted position that is based on the predetermined shape and the geometry of the aneurysm in which the braid is implanted. The implant can include a single layer of braid (e.g. a braid that can be extended to form a single layer tube) heat treated into multiple layers with retractable dual layer at the proximal end of the tubular braid. When compressed, the implant can be sufficiently short to mitigate friction forces produced when the implant is delivered unsheathed through the microcatheter.

A first portion of the tubular braid can be positioned in an aneurysm, after which the retractable dual layer can be deployed from the microcatheter and pushed onto the first portion of the tubular braid. This configuration provides three layers of braid at the neck of the aneurysm. The dual layer can potentially cover any gap between the first portion of implanted tubular braid and the aneurysm neck, and can potentially increase metal coverage, decrease porosity of the implant, and increase stasis and blood flow diversion at the neck of the aneurysm to promote the sealing and healing of the aneurysm compared a similarly shaped braided implant lacking the dual layer. The entire implant can be retractable until a desired position is achieved.

Figure 17A:
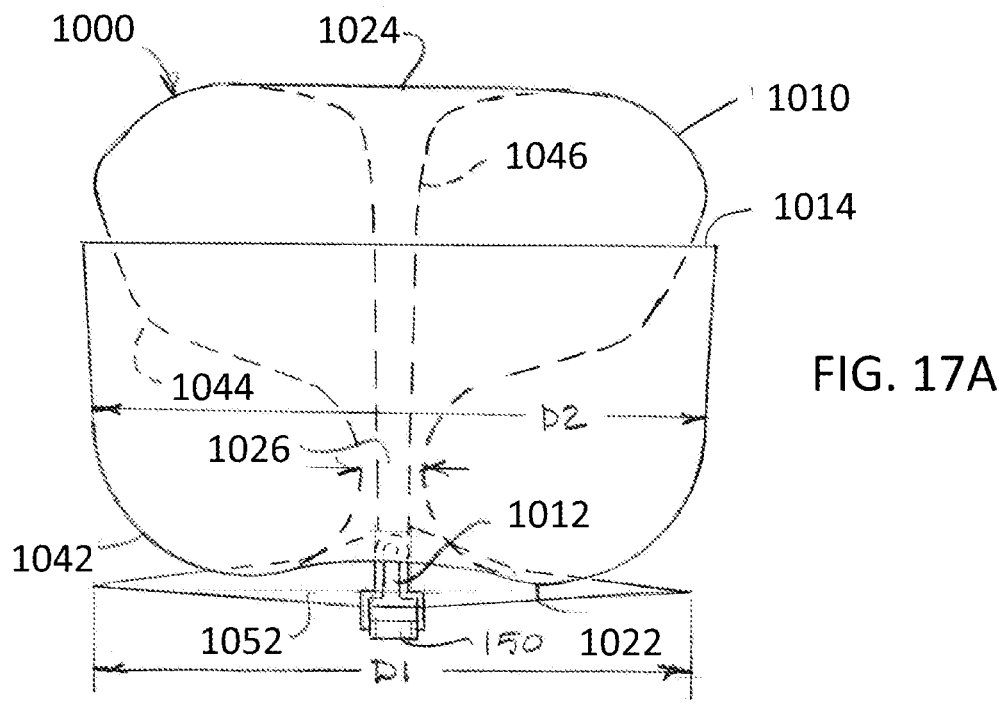
FIG. 17A is an illustration of an example implant having a tubular braid in a predetermined shape according to aspects of the present invention.
Figure 17B:
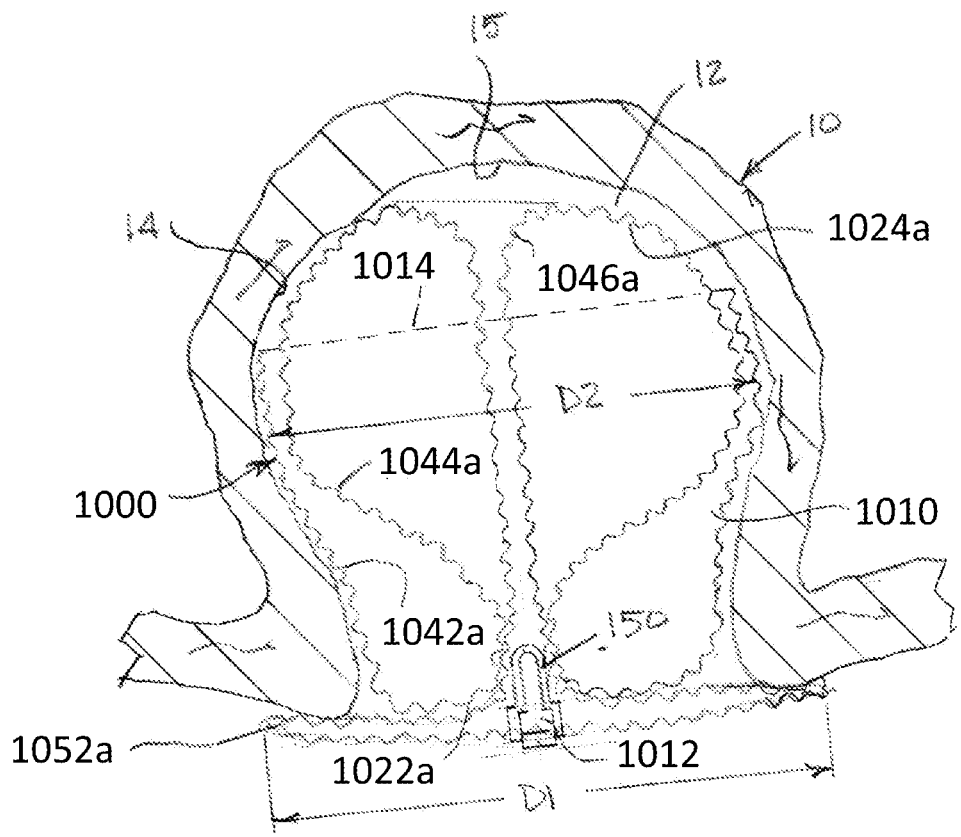
FIG. 17B is an illustration of the example implant with the tubular braid in a first implanted shape according to aspects of the present invention.

FIGS. 17A and 17B are illustrations of an example braided implant 100 that can have a predetermined shape as shown in FIG. 17A and a distinct implanted shape as illustrated in FIG. 17B. The implant 1000 can treat a range of aneurysm sizes. The implant 1000 can include a tubular braid 1010 having an open end 1014 and a pinched end 1012. The implant 1000 can include a connection and detachment feature 150 (referred to equivalently as "connection feature" and "detachment feature" herein) attached to the braid 1010 at the pinched end 1012. The pinched end 1012 can include a marker band and/or soldered point with visibility, and/or the connection feature 150 can include radiopaque material. The tubular braid 1010 can be formed in the predetermined shape (FIG. 17A), collapsed for delivery through a microcatheter, attached to a delivery system at connection feature 150, and implanted in an implanted shape such as the one shown in FIG. 17B.

Referring to FIG. 17A, when in the predetermined shape, the tubular braid 1010 can include two inversions 1022, 1024, a pinched end 1012, and an open end 1014. The tubular braid 1010 can include four segments, 1042, 1044, 1046, and 1052. The first segment 1042 can extend from the open end 1014 of the tubular braid 1010 to a proximal inversion 1022. The second segment 1044 can be encircled by the open end 1014 and extend from the proximal inversion 1022 to a distal inversion 1024. The third segment 1046 can be surrounded by the second segment 1044 and extend from the distal inversion 1024 to the proximal inversion 1022. The first segment 1042, second segment 1044, and third segment 1046 can form the first portion of the tubular braid 1010. The fourth segment 1052 can extend from the third segment 1046 radially outward from a central axis to cross the proximal inversion 1022, fold, and converge at the pinched end 1012. The fourth segment 1052 can be partially encircled by the proximal inversion 1022.

When in the predetermined shape, the tubular braid 1010 can be substantially radially symmetrical about a central vertical axis. The detachment feature 150 is illustrated in FIG. 17A as a flat key that can be used with a mechanical delivery implant system (not pictured). The tubular braid 1010 can be formed into the predetermined shape by first inverting the braid outwardly to separate the third segment 1046 from the second segment 1044 with a distal inversion 1024. Then, the second segment 1044 can be shaped over a form to produce the substantially "S" shaped profile illustrated in FIG. 17A. Next, the braid 1010 can be inverted outwardly again to separate the second segment 1044 from the first segment 1042 with a proximal inversion 1022. Finally, the fourth segment 1052 can be shaped by expanding the fourth segment 1052 radially. The fourth segment 1052 can be pressed distally into the first portion of the tubular braid 1010. It can also be advantageous to minimize a neck opening 1026 defined by the lower extension of the "S" shape of second segment 1044 to maximize occlusion of an aneurysm neck when the implant 1000 is implanted.

The tubular braid 1010 can include memory shape material that can be heat set to a predetermined shape, can be deformed for delivery through a catheter, and can self-expand to an implanted shape that is based on the predetermined shape and confined by the anatomy of the aneurysm in which it is implanted. When the tubular braid 1010 is in the predetermined shape as depicted in FIG. 17A, the fourth segment 1052 can comprise a diameter D1 greater than or approximately equal to a maximum diameter D2 of the first segment 1042. Alternatively, when the tubular braid 1010 is in the predetermined shape as depicted in FIG. 17A, the fourth segment 1052 can comprise a diameter D1 lesser than a maximum diameter D2 of the first segment 1042. When the tubular braid 1010 is in the predetermined shape (FIG. 17A), the second segment 1044 can form a sack, and at least a portion of the third segment 1046 can positioned within the sack and at least a portion of the fourth segment 1052 can be positioned external to the sack. As illustrated (FIG. 17B), when implanted, the fourth segment 1052 can be positioned external to the aneurysm sac, extending across the aneurysm neck 16. Preferably, the fourth segment 1052 can appose vasculature walls surrounding the aneurysm neck 16 when implanted. Alternatively, the shaped fourth segment 1052 can also be placed within the aneurysm sac. The detachment feature 150 can be implanted centrally in the aneurysm neck 16. The detachment feature 150 can be positioned external to the sac 12.

The tubular braid 1010 in the implanted shape (FIG. 17B) can be radially or vertically compressed or extended compared to the predetermined shape. As illustrated in FIG. 17B, when in the implanted shape, the braid 1010 can have an outer layer 1042a corresponding to the first segment 1042 of the predetermined shape and positioned to contact an aneurysm wall 14 of the aneurysm 10, a proximal inversion 1022a corresponding to the proximal inversion 1022 of the predetermined shape and positioned to be placed approximate a neck 16 of the aneurysm 10, and a sack 1044a corresponding to the second segment 1044 of the predetermined shape and positioned to appose a portion of the aneurysm wall 14 of the aneurysm 10 and apposing the outer layer 1042a. A distal inversion 1024a can correspond to the distal inversion 1024 of the predetermined shape, a third segment 1046a can correspond to the third segment 1046 in the predetermined shape. The braid 1010 can also have a fourth segment 1052a corresponding to the fourth segment 1052 of the predetermined shape and extending from the third segment 1046a radially outward from a central axis to cross the proximal inversion 1022a, fold, and converge at the pinched end 1012. As described in FIG. 17A, the fourth segment 1052a can be pressed distally into the first portion of the tubular braid 1010.

By pressing the fourth segment 1052a distally into the first portion of the tubular braid 1010, the first portion 1042a, of the tubular braid 1010 can be moved towards the distal portion of an aneurysm wall 15 to occlude a portion of the neck 16 of the aneurysm 10. Pushing the fourth segment 1052a into the first portion of the braid 1010 can help conform the implant 1000 to the shape of the aneurysm 10 and resist compaction. The fourth segment 1052a when expanded radially and pressed into the first portion of the braid 1010 also can provide additional coverage at the neck 16 of the aneurysm 10 to increase thrombosis and seal the aneurysm 10. When the fourth segment 1052a is pressed into the first portion of the braid 1010, three layers of braid are present at the neck of the aneurysm. The fourth segment 1052a can cover spatial gaps between the first portion of implanted tubular braid 1010 and the aneurysm neck 16, and can potentially increase metal coverage, decrease porosity of the implant 1000, and increase stasis and blood flow diversion at the neck 16 of the aneurysm 10 to promote the sealing and thrombosis of the aneurysm 10. The fourth segment 1052a can be shaped to occlude the majority of an aneurysm neck 16 when the device 1000 is implanted. The fourth segment 1052a can be shaped to completely occlude an aneurysm neck 16 when the device 1000 is implanted.

When the tubular braid 1010 is in the implanted shape (FIG. 17B), the fourth segment 1052a can comprise a diameter D1 greater than or approximately equal to a maximum diameter D2 of the first segment 1042a. Alternatively, when the tubular braid 1010 is in the implanted shape (FIG. 17B), the fourth segment 1052a can comprise a diameter D1 lesser than a maximum diameter D2 of the first segment 1042a. When the tubular braid 1010 is in the implanted shape (FIG. 17B), the second segment 1044a can form a sack, and at least a portion of the third segment 1046a can be positioned within the sack and at least a portion of the fourth segment 1052a can be positioned external to the sack. The shaped fourth segment 1052a can also be placed within the aneurysm sac 12 with only the detachment point 150 external to the sac 12.

Figure 18D:
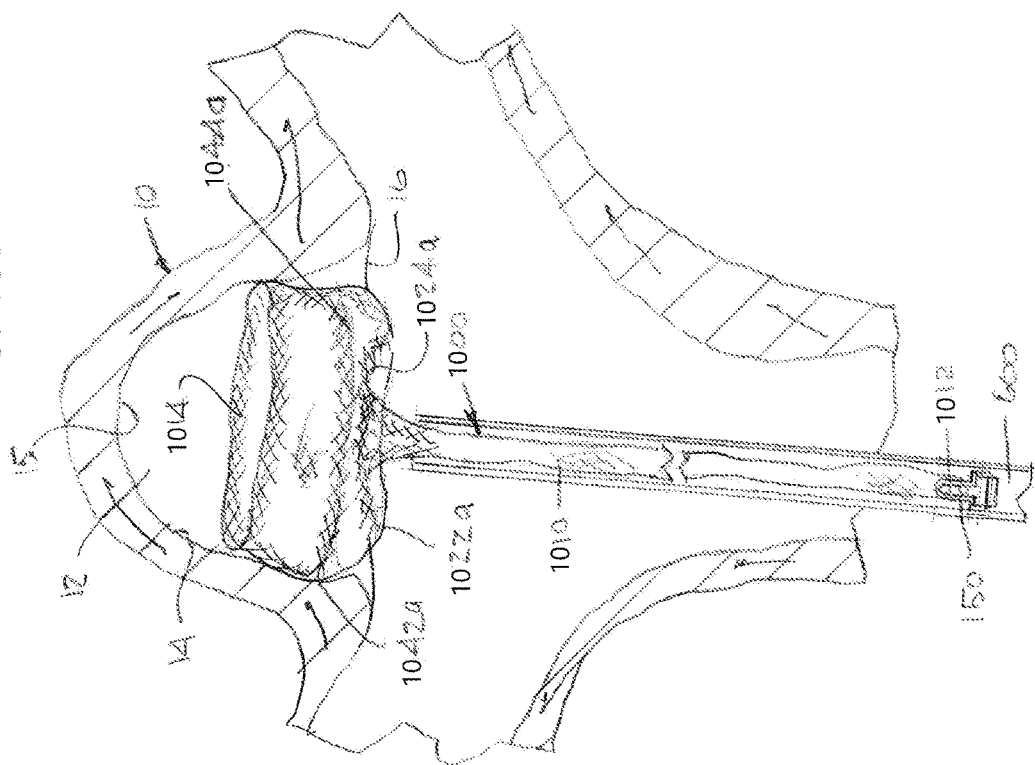

FIGS. 18A through 18I are illustrations of an example implant 1000 having a braid 1010 expanding to an implanted shape that is based on a predetermined shape and the anatomy of the aneurysm and nearby blood vessel as the braid 1010 exits a microcatheter 600. The implant 1000 has a predetermined shape similar to the shape illustrated in FIG. 17A. As illustrated in FIG. 18A, the braid 1010 can be shaped to a delivery shape that is extended to a single layer of tubular braid having a compressed circumference/diameter sized to be delivered through the microcatheter 600 and a length L. As will be appreciated and understood by a person of ordinary skill in the art, the length L of a specific braid 1010 can be tailored based on the size and shape of the aneurysm being treated. The length L can be approximately 1 inch in length.

Figure 18C:
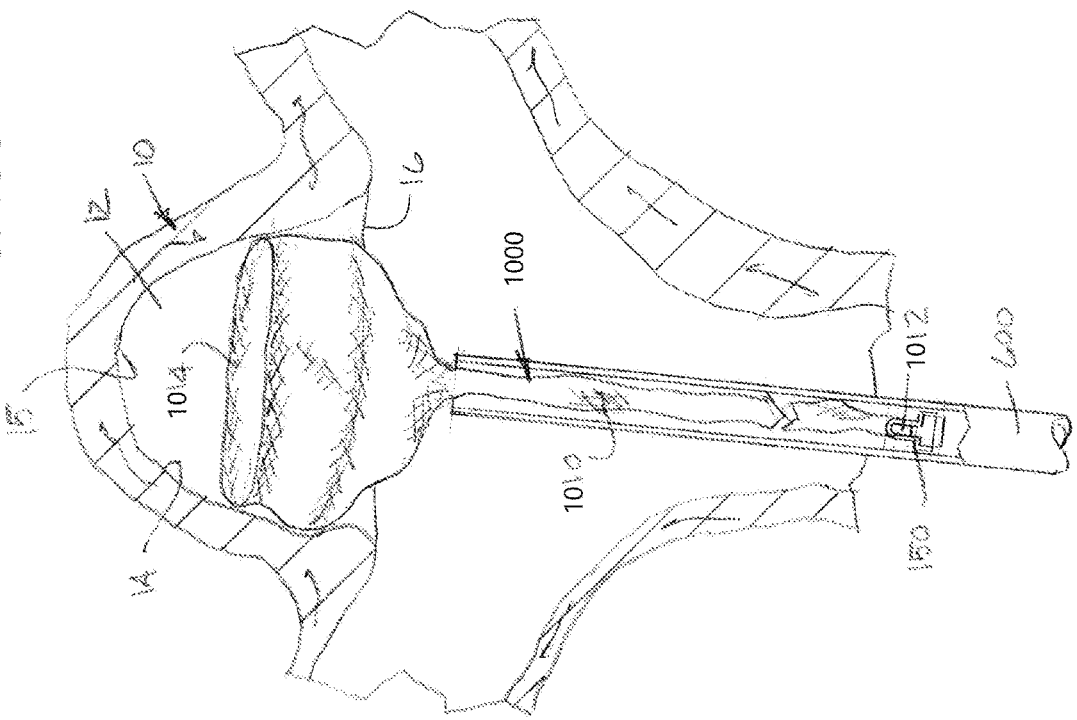

During delivery through the microcatheter 600, the detachment feature 150 can be attached to a delivery system at a proximal end of the implant 1000, the pinched end 1012 can be positioned near the proximal end of the implant 1000, and the open end 1014 can define the distal end of the implant 1000. Collapsing the braid 1010 to a single layer tube can result in a braid 1010 that has a sufficiently small diameter and a sufficiently short length L to mitigate effects of friction force on the braid 1010 when it is delivered through the microcatheter, allowing the braid 1010 to be delivered unsheathed in some applications As illustrated in FIG. 18B, the implant 1000 can be delivered to an aneurysm 10 through the microcatheter 600. The open end 1014 can be positioned to exit the microcatheter 600 before any other portion of the braid 1010 exits the microcatheter. The open end 1014 can expand within the aneurysm sac 12 as it exits the microcatheter 600. The illustrated aneurysm 10 is positioned at a bifurcation including a stem blood vessel 20 and two branch vessels 22a, 22b and the microcatheter 600 is illustrated being delivered through the stem blood vessel 20. It is contemplated that the implant could be delivered to an aneurysm on a sidewall of a blood vessel through a curved microcatheter, and such a procedure is intended to be embraced by the scope of the present disclosure. As illustrated in FIG. 18C, the distal portion of the braid 1010 can continue to expand radially within the aneurysm sac 12 as it exits the microcatheter 600. As the braid 1010 is further pushed distally from the microcatheter 600, the braid 1010 can appose the aneurysm wall 14 and conform approximate the aneurysm neck 16. The aneurysm 10 being treated can have a diameter that is less than the outer diameter of the tubular braid 1010 in the predetermined shape so that the braid 1010 tends to expand outwardly, providing a force against the aneurysm wall 14 and sealing approximate the perimeter of the aneurysm neck 16.

Figure 18F:
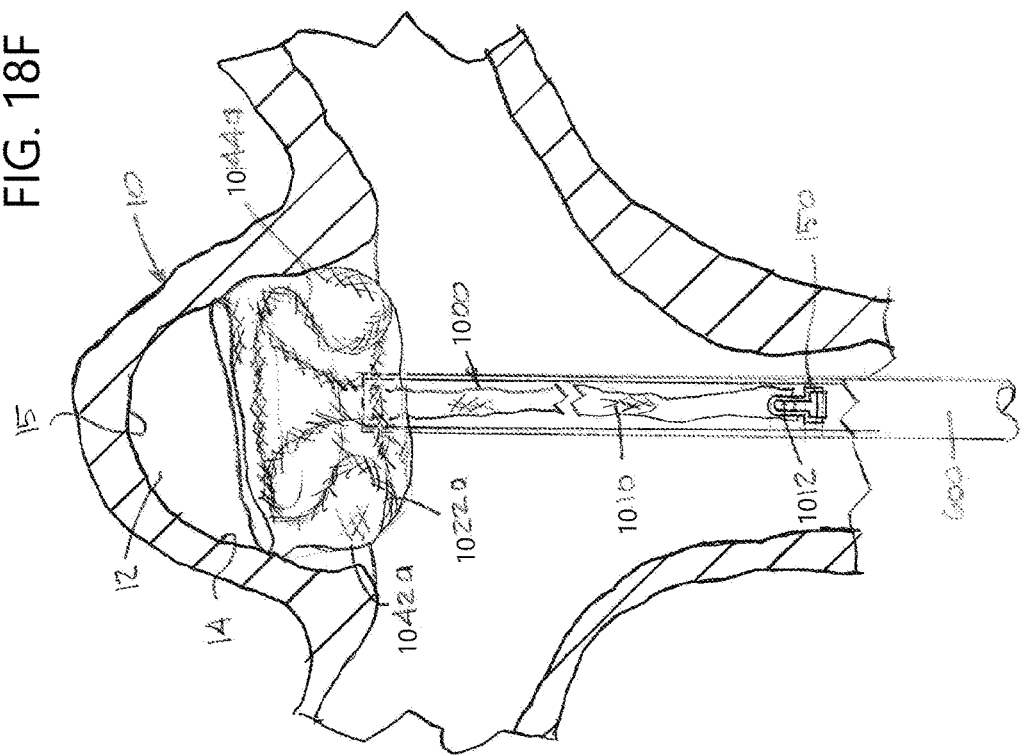
Figure 18E:
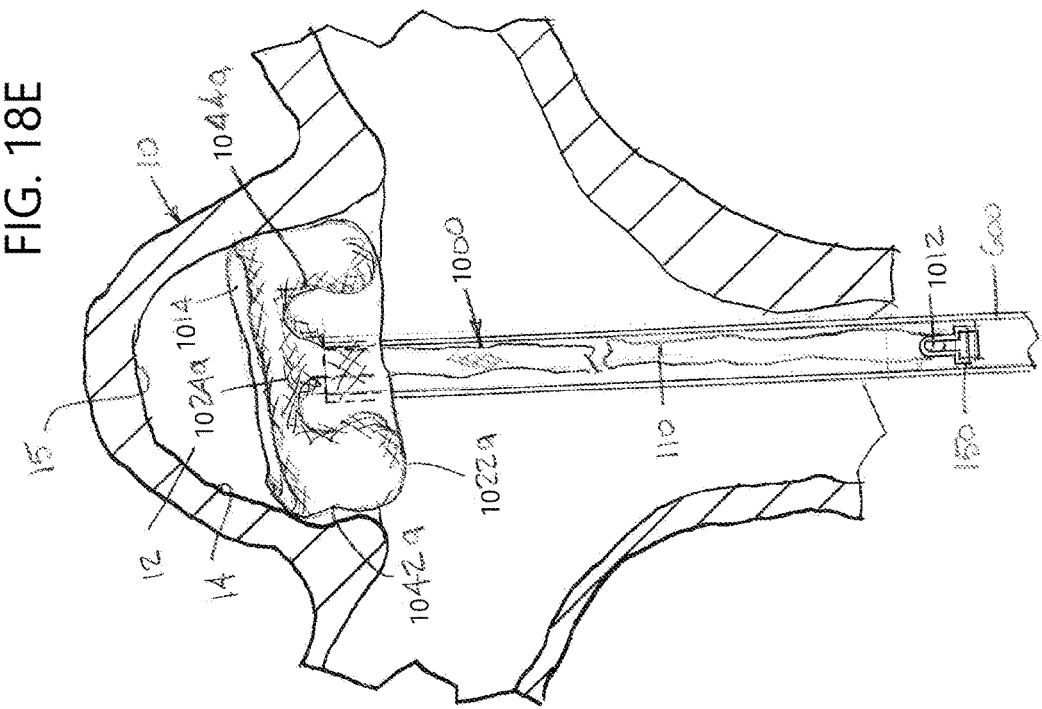

As illustrated in FIG. 18D, the braid 1010 can form the proximal inversion 1022a defining the first segment 1042a as the braid 1010 is further pushed out of the microcatheter 600. The proximal inversion 1022a can be positioned approximate the aneurysm neck 16. The distal inversion 1024a defining the second segment 1044a can also begin to form as the braid 1010 is pushed out of the microcatheter 600. As illustrated in FIGS. 18E through 18F, the "S" shape of the second segment 1044a can begin to form as the braid 1010 is further pushed from the microcatheter 600.

Figure 18G:
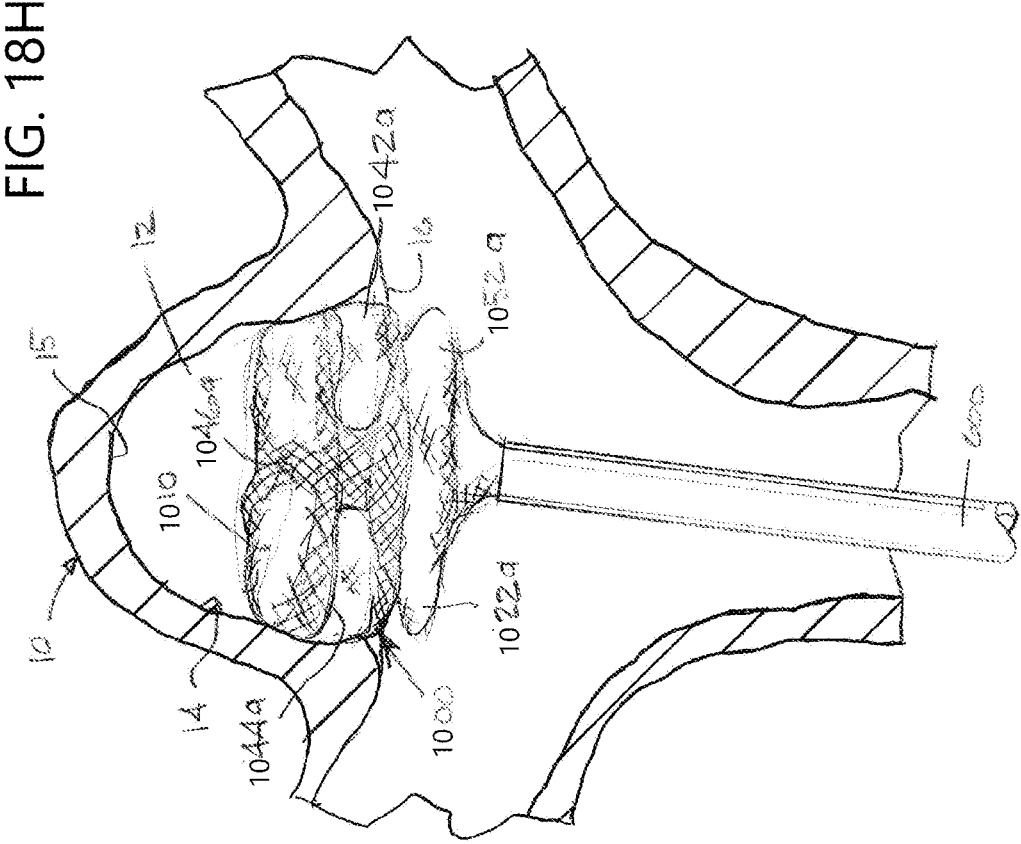

As illustrated in FIG. 18G, once the first portion of the braid 1010, which can comprise the first segment 1042a, second segment 1044a, and third segment 1046a, is in place within the aneurysm sac 12, the fourth segment 1052a can radially expand outside the aneurysm 10 as the distal portion of the braid 1010 continues to exit the microcatheter 600.

Figure 18H:
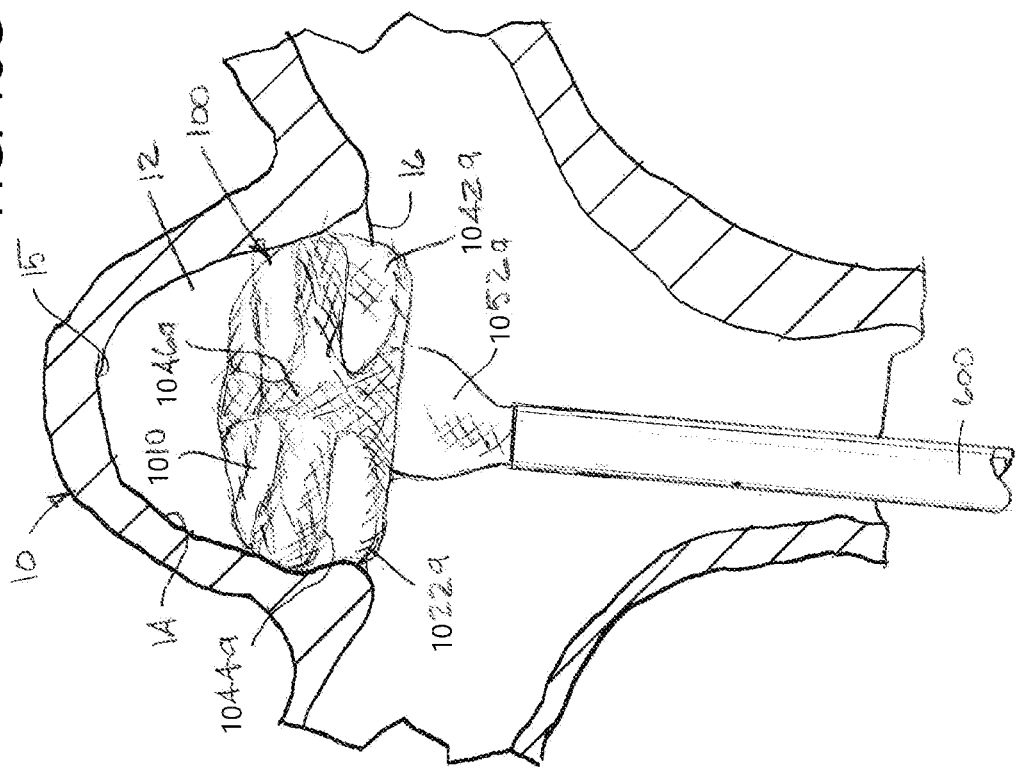

As illustrated in FIG. 18H, the fourth segment 1052a can then be compressed distally as it continues to radially expand, compressing the fourth segment 1052a up into the first portion of the braid 1010.

Figure 18I:
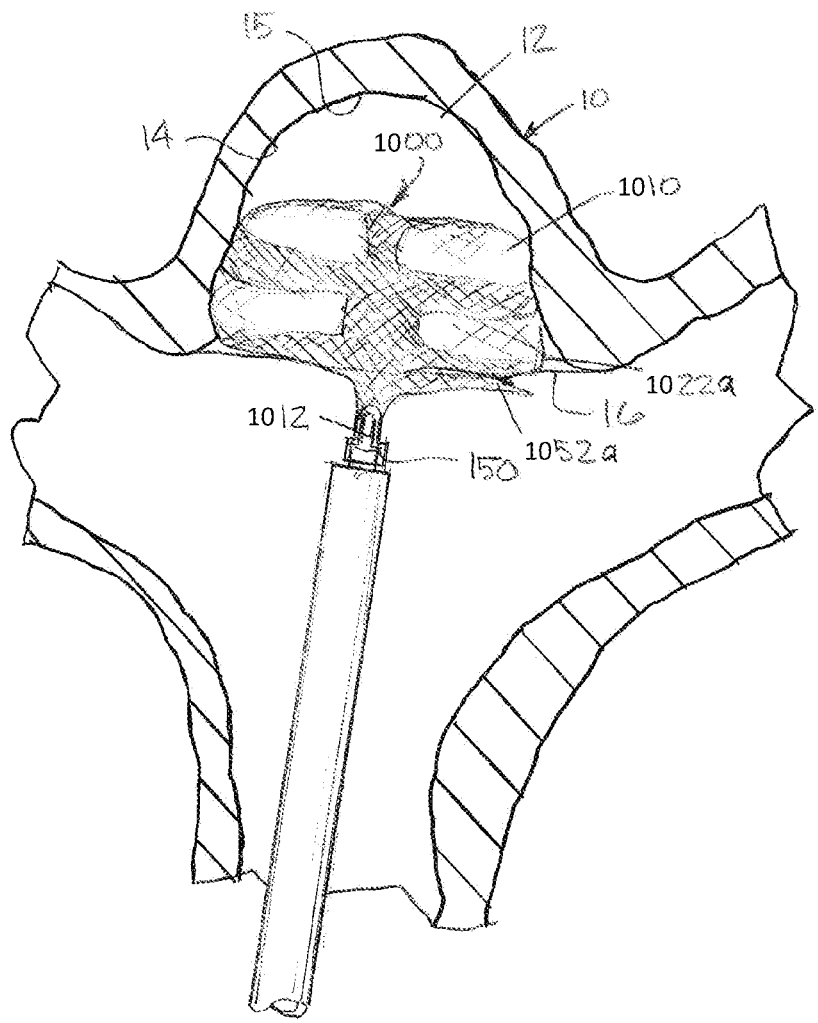

Finally, as illustrated in FIG. 18I, the fourth segment 1052a can be compressed distally into the first portion of the braid 1010, at least partially occluding the neck 16 of the aneurysm 10 and the neck opening 1026. The pinched end 1012 and/or the detachment point 150 can remain external to the aneurysm sac once the fourth segment 1052a has reached its final expanded and compressed state. The fourth segment 1052a when compressed can be compressed to a minimal thickness as to not become an obstruction to the surrounding blood vessels.

Before the implant 1000 is released from the delivery system, the implant 1000 can be partially or fully retracted into the microcatheter 600 and repositioned.

Figure 19A:
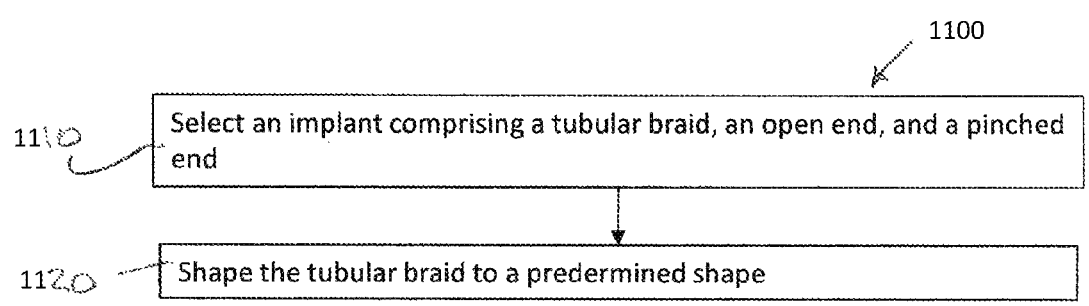
FIGS. 19A through 19B are flow diagrams for a method of forming an occlusive device to treat an aneurysm.
Figure 19B:
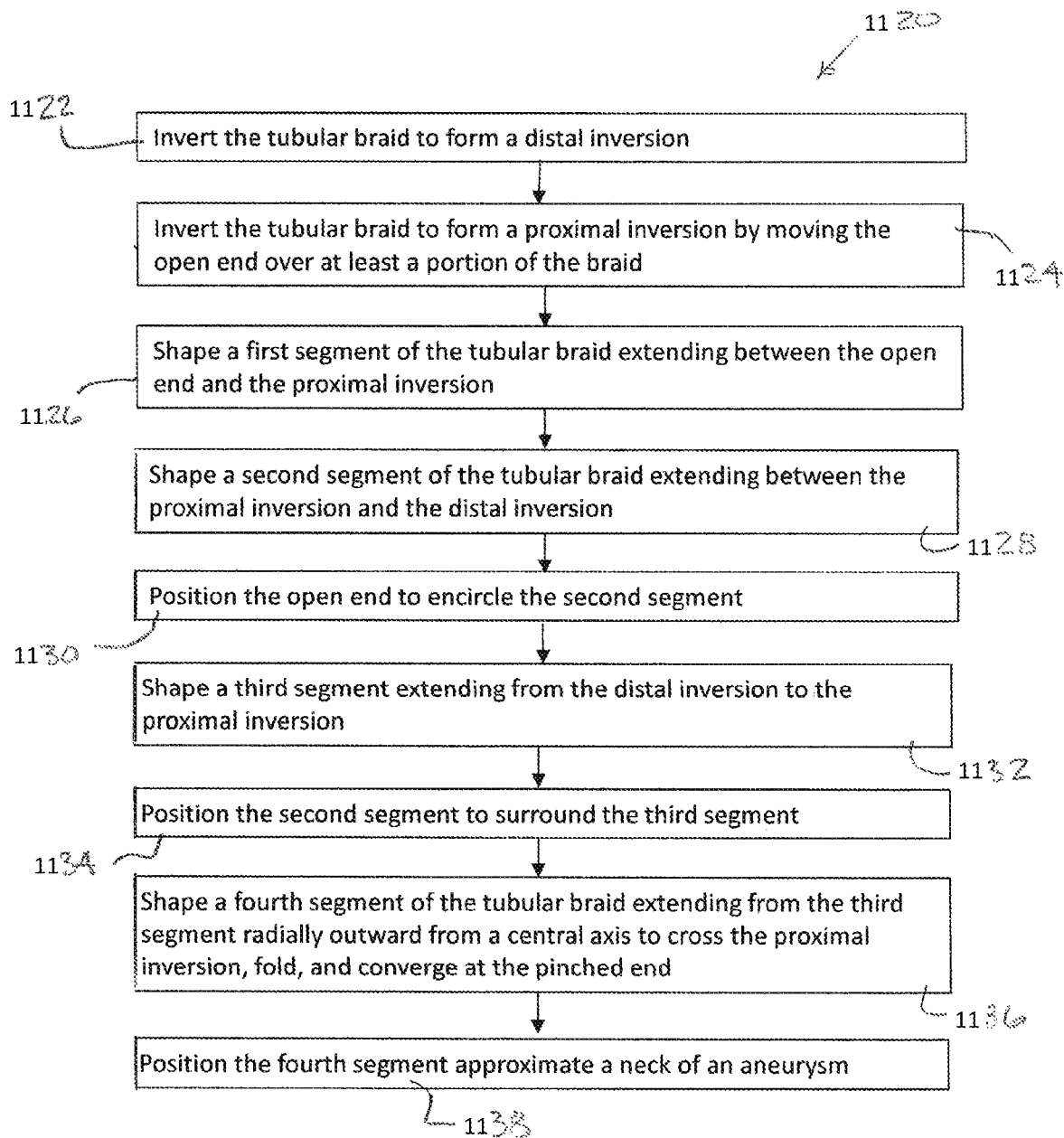

FIG. 19A is a flow diagram for a method 1100 for forming an occlusive device to treat an aneurysm 10. Step 1110 includes selecting an implant comprising a tubular braid, an open end, and a pinched end. Step 1120 includes shaping the tubular braid to a predetermined shape, such as the one illustrated in FIG. 17A. As illustrated in FIG. 19B, step 1120 can further comprise additional steps. Step 1122 includes inverting the tubular braid to form a distal inversion. Step 1124 inverts the tubular braid to form a proximal inversion by moving the open end over at least a portion of the braid. Step 1126 includes shaping a first segment of the tubular braid extending between the open end and the proximal inversion. Step 1128 shapes a second segment of the tubular braid extending between the proximal inversion and the distal inversion. Step 1130 includes positioning the open end to encircle the second segment. Step 1132 shapes a third segment extending from the distal inversion to the proximal inversion. Step 1134 includes positioning the second segment to surround the third segment. Step 1136 shapes a fourth segment of the tubular braid extending from the third segment radially outward from a central axis to cross the proximal inversion, fold inwardly toward the central axis, and converge at the pinched end. Step 1138 includes positioning the fourth segment approximate a neck of an aneurysm.

In method 1100, step 1120 of shaping the tubular braid to the predetermined shape can further include shaping the fourth segment to comprise a diameter greater than or approximately equal to a maximum diameter of the first segment. In method 1100, the step 1120 of shaping the tubular braid to the predetermined shape can further include shaping the fourth segment to a diameter lesser than a maximum diameter of the first segment. The method 1100 can further include shaping the tubular braided implant to a delivery shape sized to traverse a lumen of a microcatheter.

Figure 20A:
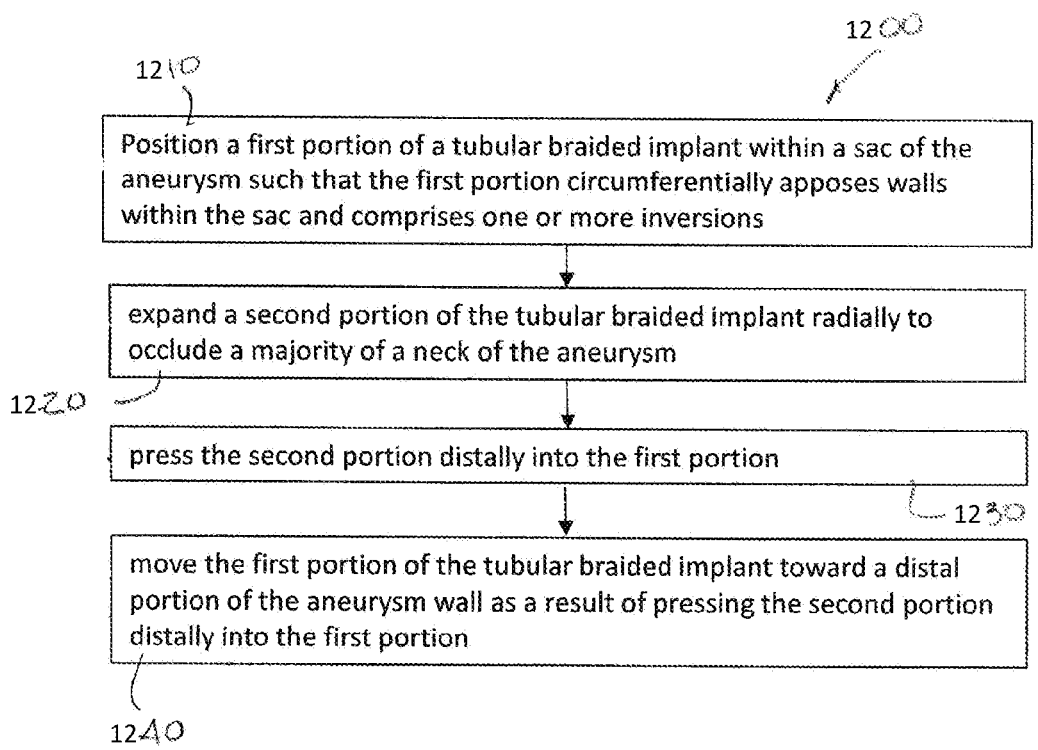
FIGS. 20A through 20B are flow diagrams for a method for treating an aneurysm.

FIG. 20A is a flow diagram for a method 1200 for a method for treating an aneurysm 10. Step 1210 positions a first portion of a tubular braided implant, the tubular braided implant comprising a tubular braid, an open end, and a pinched end, within a sac of the aneurysm such that the first portion circumferentially apposes walls within the sac. The first portion can include one or more inversions. Step 1220 includes expanding a second portion of the tubular braided implant radially to occlude a majority of a neck of the aneurysm. Step 1230 presses the second portion distally into the first portion. Pressing the second portion distally into the first portion can create three layers of braid at the neck of the aneurysm. The second portion can cover any spatial gaps between the first portion and the aneurysm neck, and can potentially increase metal coverage, decrease porosity of the implant, and increase stasis and blood flow diversion at the neck of the aneurysm to promote the sealing and healing of the aneurysm. Step 1240 includes moving the first portion of the tubular braided implant toward a distal portion of the aneurysm wall as a result of pressing the second portion distally into the first portion.

Figure 20B:
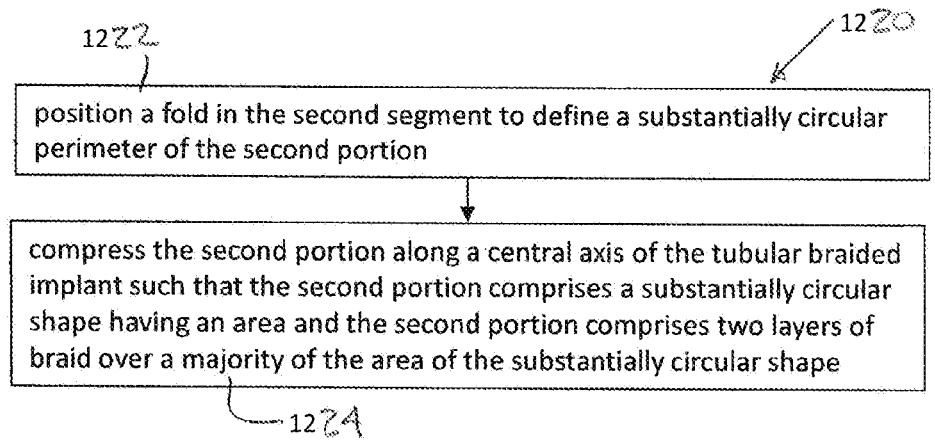

As illustrated in FIG. 20B, step 1220 can further include step 1222, which includes positioning a fold in the second segment to define a substantially circular perimeter of the second portion. Step 1220 can additionally, or alternatively include step 1224, which includes compressing the second portion along a central axis of the tubular braided implant such that the second portion comprises a substantially circular shape having an area and the second portion comprises two layers of braid over a majority of the area of the substantially circular shape.

Step 1210 can further include shaping the tubular braided implant to form a columnar post encircling a central axis of the tubular braided implant and extending a majority of a height of the first portion. Step 1210 can further include positioning a proximal inversion in the first portion of the tubular braided implant approximate the neck of an aneurysm and positioning a distal inversion in the first portion of the tubular braided implant approximate the distal portion of the aneurysm wall. Step 1210 can further include positioning the open end of the tubular braided implant to circumferentially appose the aneurysm wall, shaping a first segment of the tubular braid extending between the open end and the proximal inversion to appose an at least a portion of a wall of the aneurysm within the aneurysm's sac, and shaping a second segment of the tubular braid such that the first segment provides an outwardly radial force in a plane defining a boundary between the aneurysm and blood vessel branches, the force sufficient to appose the first segment to walls of the aneurysm.

Step 1230 can further include pressing the second portion of the tubular braided implant against the proximal inversion in the first portion of the tubular braided implant. Step 1240 can further include moving the distal inversion in the first portion of the tubular braided implant toward the distal portion of the aneurysm wall.

The method 1200 can further include shaping the tubular braided implant to form a columnar post encircling a central axis of the tubular braided implant and extending a majority of a height of the first portion. The method 1200 can further include retracting the tubular braid until a desired position is achieved relative to the aneurysm. The method 1200 can further comprise shaping the tubular braided implant to a delivery shape sized to traverse a lumen of a microcatheter.

Figure 21A:
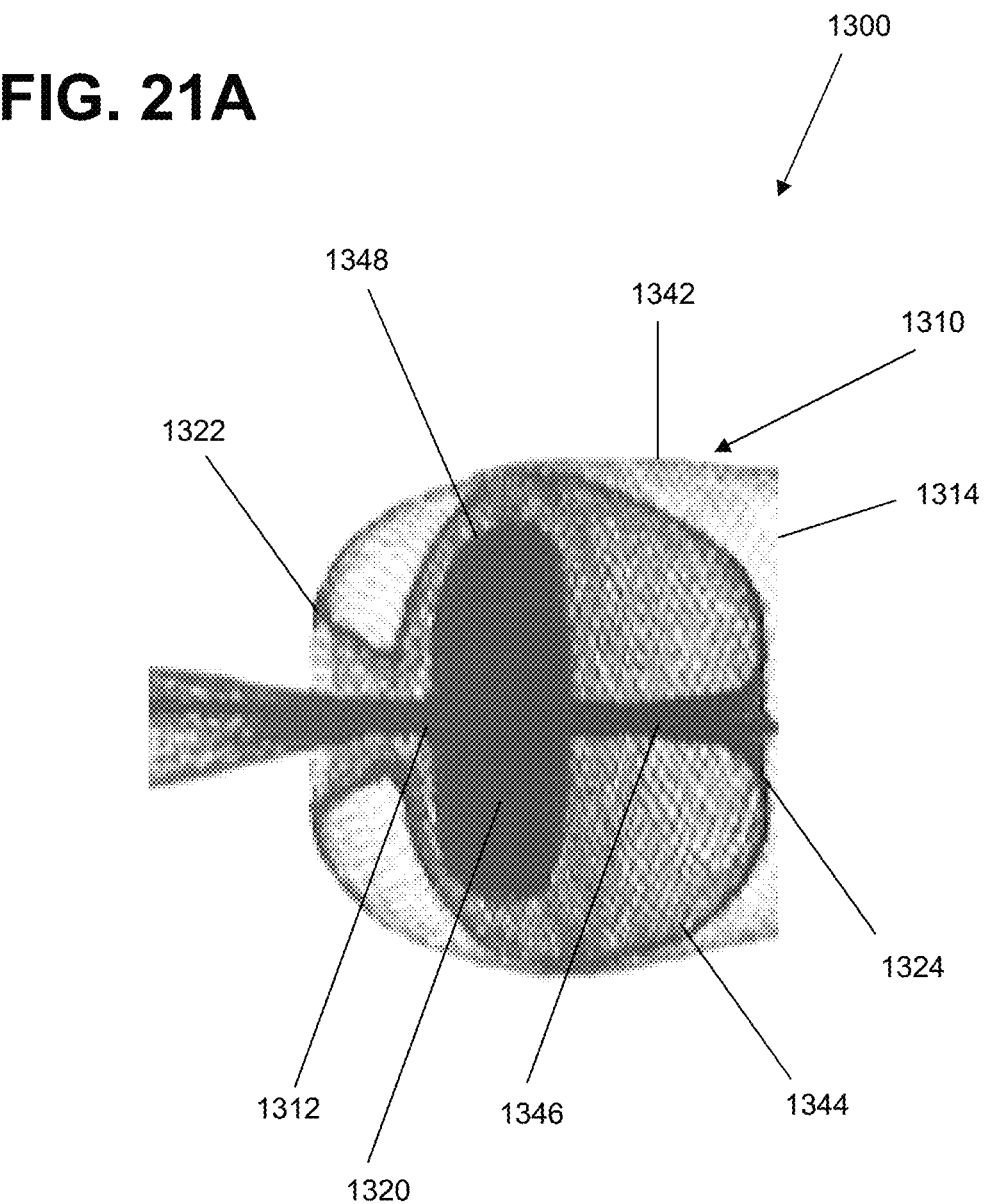
FIGS. 21A through 21B are illustrations of an example implant being formed into a predetermined shape according to aspects of the present invention.
Figure 21B:
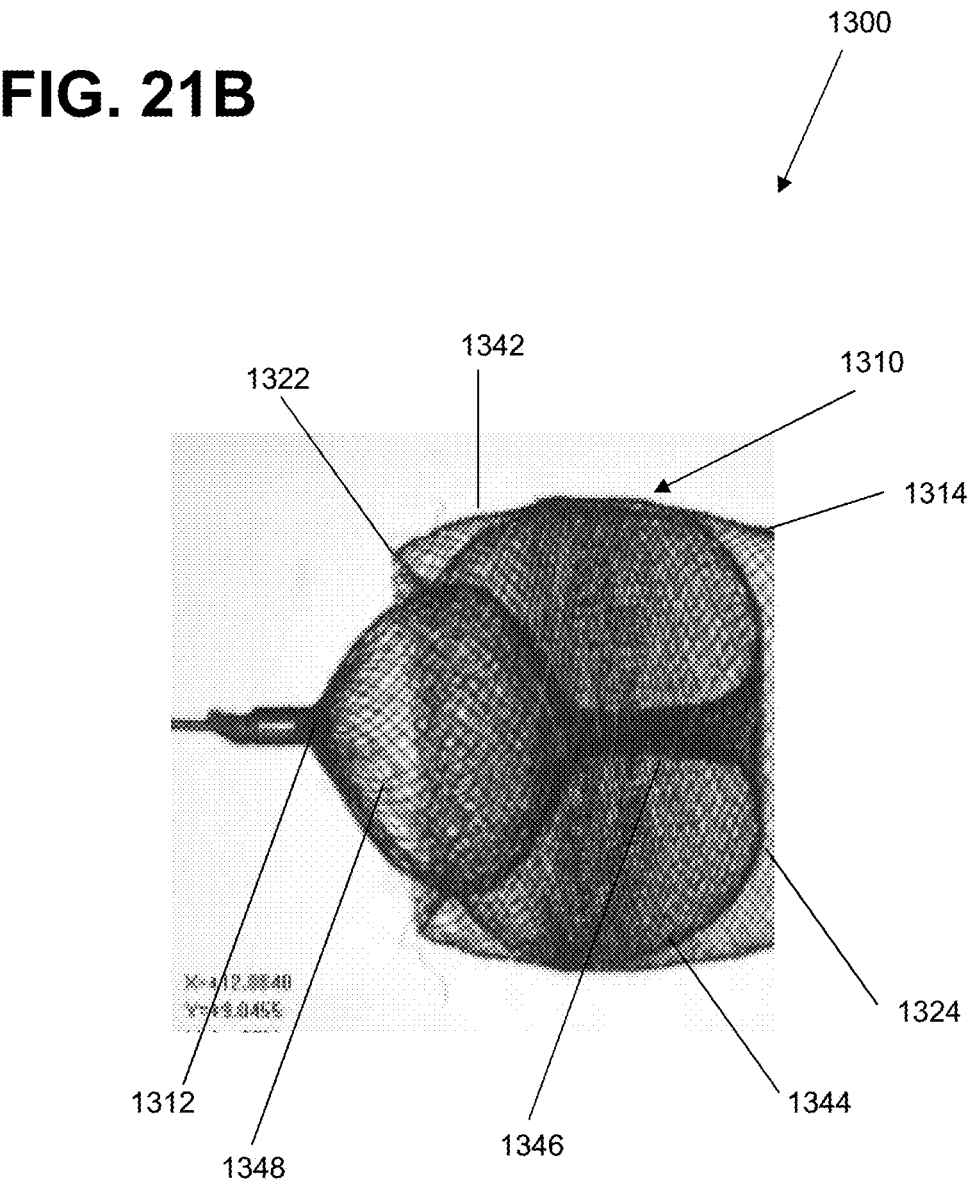

FIGS. 21A through 21B are illustrations of an example braided implant 1300 as it is formed into a predetermined shape (FIG. 21B). The implant 1300 can treat a range of aneurysm sizes. The implant 1300 can include a tubular braid 1310 having an open end 1314 and a pinched end 1312, similar to FIGS. 17A and 17B. The tubular braid 1310 can include memory shape material that can be heat set to a predetermined shape, can be deformed for delivery through a catheter, and can self-expand to an implanted shape that is based on the predetermined shape and confined by the anatomy of the aneurysm in which it is implanted.

When in the predetermined shape, the tubular braid 1310 can be substantially radially symmetrical about a central vertical axis. The implant 1300 can include a connection and detachment feature 150 as illustrated in prior figures. The pinched end 1312 can include a marker band and/or soldered point with visibility, and/or the connection feature 150 can include radiopaque material. The tubular braid 1310 can be formed in the predetermined shape (FIG. 21B), collapsed to a delivery shape with a single layer of braid 1310 for delivery through a microcatheter similar to FIG. 18A, attached to a delivery system at connection feature 150, and implanted in an implanted shape such as the ones shown in FIGS. 22A-6C in a manner similar to the delivery described in FIGS. 18A through 18F.

Referring to FIG. 21A, the tubular braid 1310 can include two inversions, 1322, 1324, a pinched end, 1312, and an open end 1314. The tubular braid 1310 as depicted in FIG. 21A can include four segments, 1342, 1344, 1346, and 1348. The first segment 1342 can extend from the open end 1314 of the tubular braid 1310 to a proximal inversion 1322. The second segment 1344 can be encircled by the open end 1314 and can extend from the proximal inversion 1322 to a distal inversion 1324. The third segment 1346 can be surrounded by the second segment 1344.

The tubular braid can be formed into a predetermined shape by first inverting the braid 1310 outwardly to separate the third segment 1346 from the second segment 1344 with a distal inversion 1324. Then, the second segment 1344 can be shaped over a form or mold. The form can be in the shape of a sack. Next, the braid 1310 can be inverted outwardly again to separate the second segment 1344 from the first segment 1342 with a proximal inversion 1322.

As further illustrated in FIG. 21A, the third segment 1346 can span from the distal inversion 1324 to the ball segment 1348. The first segment 1342, second segment 1344, and third segment 1346 can form a first portion of the tubular braid 1310. The ball segment 1348 can extend from a proximal portion of the third segment 1346 radially outward from a central axis of the tubular braid 1310 to form a substantially ellipsoid shape and converge at the pinched end 1312. A mold 1320 can be applied, and this form wherein the ball segment 1348 is shaped can be treated with heat in order to set the predetermined shape as depicted in FIG. 21B.

As seen in FIG. 21B, the ball segment 1348 can be pressed distally into the first portion of the tubular braid 1310. When the ball segment 1348 is pressed distally into the first portion of the tubular braid 1310, the ball segment 1348 can provide a radially outward force to appose the proximal inversion 1322. Further, when the ball segment 1348 is pressed distally into the first portion of the tubular braid 1310, the ball segment 1348 can be at least partially enclosed within the second segment 1344 distal to the proximal inversion 1322. The ball segment 1348 can also be fully enclosed within the second segment 1344 distal to the proximal inversion 1322. When the tubular braid 1310 is in the predetermined shape, the second segment 1344 can form a sack, and at least a portion of the third segment 1346 can positioned within the sack and at least a portion of the ball segment 1348 can be positioned external to the sack. The ball segment 1348 can occlude at least a portion of the proximal inversion 1322 to seal the opening created by the proximal inversion 1322.

Figure 22A:
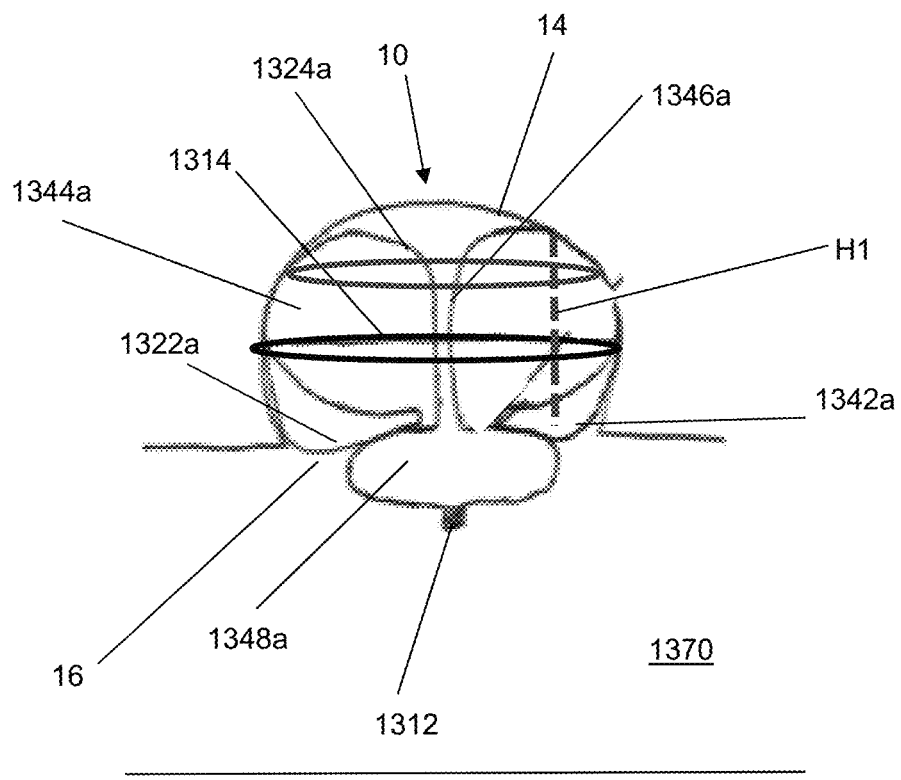
FIGS. 22A through 22C are illustrations of an implant having a tubular braid in an implanted shape according to aspects of the present invention.
Figure 22B:
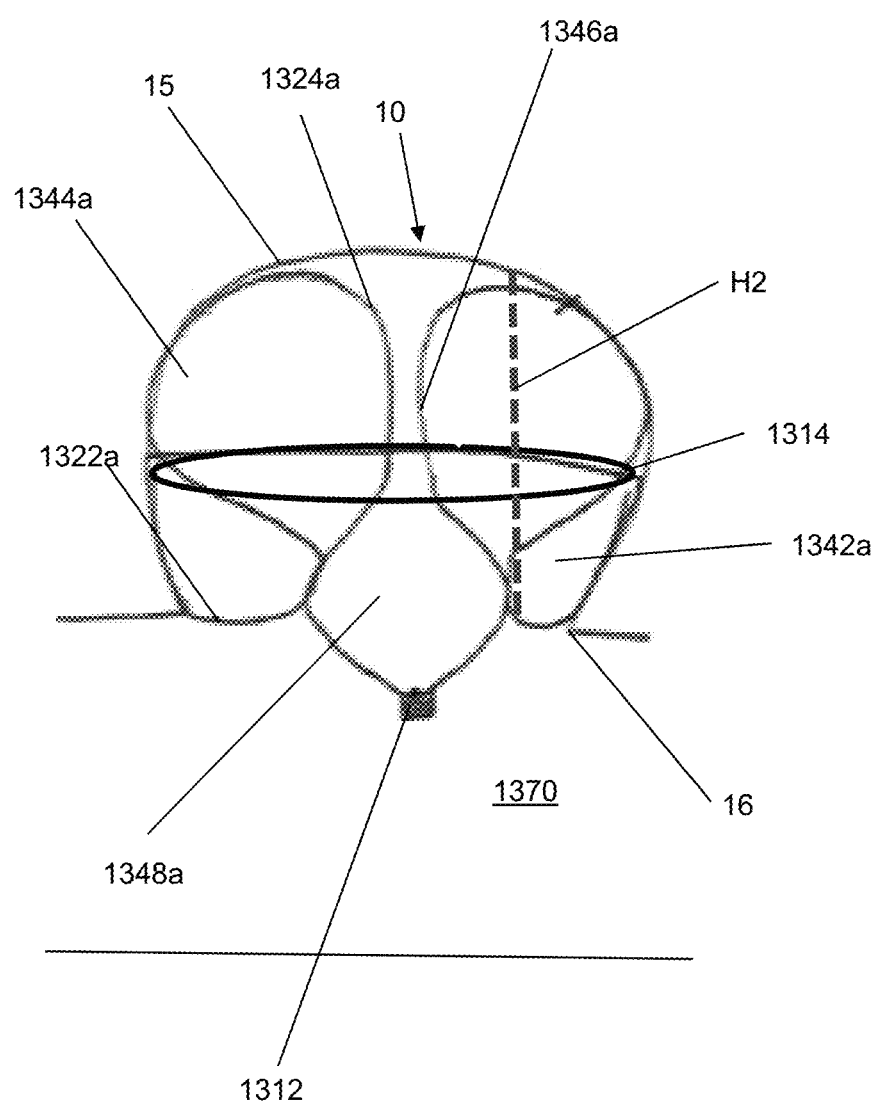
Figure 22C:
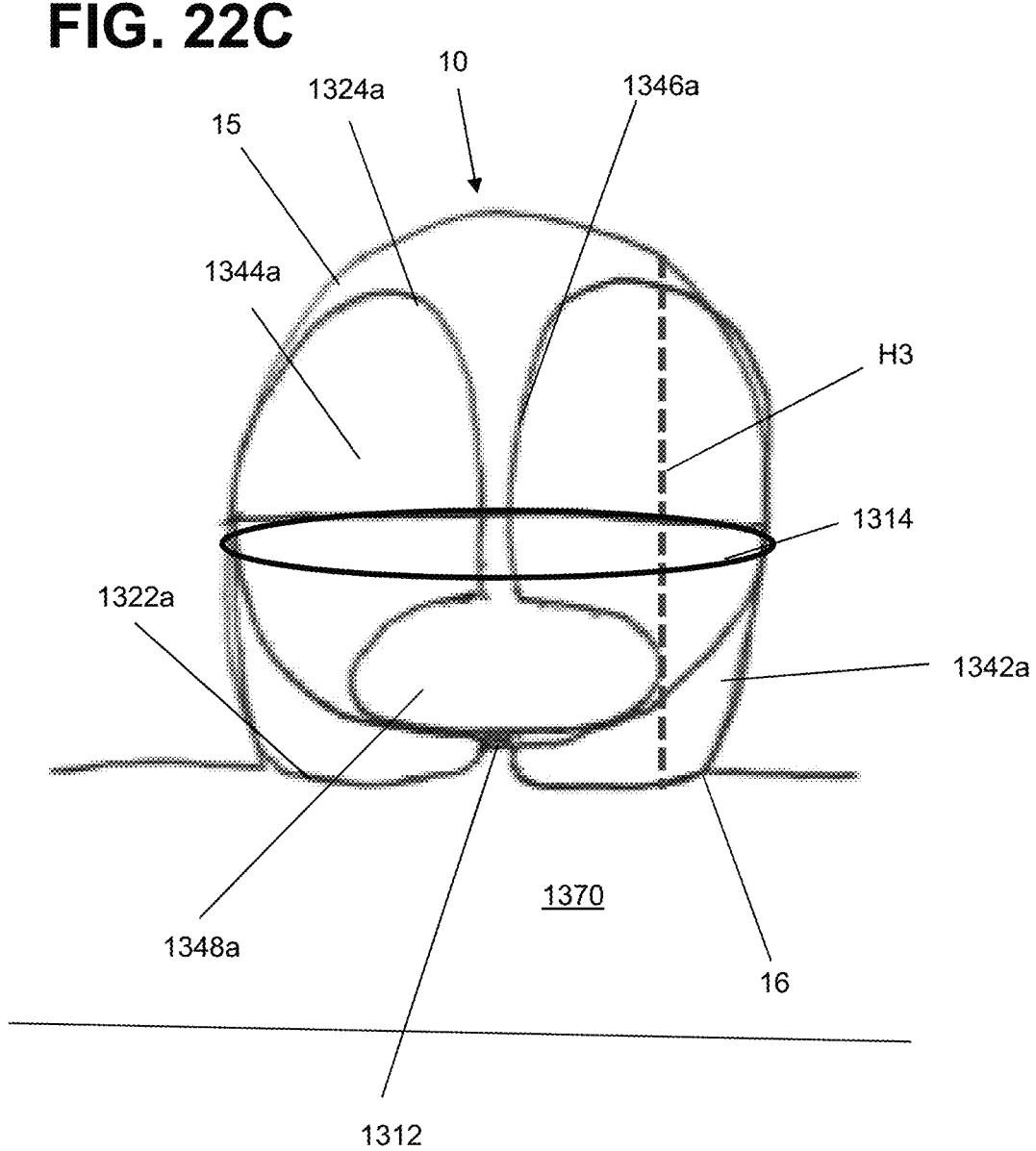

FIGS. 22A through 22C are illustrations of an example braided implant 1300 implanted within an aneurysm 10. The tubular braid 1310 can be radially or vertically compressed or extended compared to the predetermined shape to conform to aneurysms of varying sizes, heights, and shapes. As illustrated in FIG. 22A, when in the implanted shape in an aneurysm 10 with a height H1, the braid 1310 can have an outer layer 1342*a* corresponding to the first segment 1342 of the predetermined shape and positioned to contact an aneurysm wall 14 of the aneurysm 10, a proximal inversion 1322*a* corresponding to the proximal inversion 1322 of the predetermined shape and positioned to be placed approximate a neck 16 of the aneurysm 10, and a sack 1344*a* corresponding to the second segment 1344 of the predetermined shape and positioned to appose the outer layer 1342*a*. A distal inversion 1324*a* can correspond to the distal inversion 1324 of the predetermined shape, and a third segment 1346*a* can correspond to the third segment 1346 in the predetermined shape. The braid 1310 can also have a ball segment 1348*a* corresponding to the ball segment 1348 of the predetermined shape and extending from the third segment 1346*a* radially outward from a central axis to form a substantially ellipsoid shape and converge at the pinched end 1312. As described in FIG. 21B, the ball segment 1348*a* can be pressed distally into the first portion of the tubular braid 1310. Pressing the ball segment 1348*a* distally into the first portion of the tubular braid 1310 can result in multiple layers of braid 1310 seated at the neck 16 of the aneurysm 10. These multiple layers of braid 1310 can inhibit blood flow into the aneurysm 10 by better occluding the aneurysm neck 16, by better occluding the channel formed by the proximal inversion 1322*a*, or both.

As illustrated in FIG. 22A, when implanted, the ball segment 1348*a* can be positioned external to the aneurysm 10, extending across the aneurysm neck 16. The ball segment 1348*a* can occlude at least a portion of the aneurysm neck 16. The ball segment 1348*a* can also occlude at least a portion of the proximal inversion 1322*a* to seal the opening created by the proximal inversion 1322*a*.

FIG. 22B depicts an implant 1300 in an aneurysm 10 with a height H2. The height H2 of the aneurysm in FIG. 22B can be greater than the height H1 of the aneurysm in FIG. 6A. By pressing the ball segment 1348*a* into the first portion of the tubular braid 1310 within an aneurysm with a height H2, the first portion 1342*a* of the tubular braid 1310 can be moved further into the aneurysm 10 towards the distal portion of an aneurysm wall 15. The ball segment 1348*a* can occlude at least a portion of the neck 16 of the aneurysm 10. The ball segment 1348*a* can also occlude at least a portion of the proximal inversion 1322*a* to seal the opening created by the proximal inversion 1322*a*. Pushing the ball segment 1348*a* into the first portion of the braid 1310 can also appose the proximal inversion 1322 to provide a radially outward force against the proximal inversion 1322 so that the tubular braid 1310 apposes a wall 14 of the aneurysm 10 approximate a neck 16 of the aneurysm 10.

Alternatively, pushing the ball segment 1348*a* distally into the first portion of the tubular braid 1310 can push the third segment 1346*a* distally into the aneurysm towards a distal portion of the aneurysm wall 15, independent of distal movement of the outer layer 1342*a* and/or sack 1344*a*. This can extend the height of the implant 1300 to better conform to the height of the aneurysm H2. At least a portion of the ball segment 1348*a* can be enclosed by the sack 1344*a*. At least a portion of the ball segment 1348*a* can be positioned external to the sack 1344*a*.

As illustrated in FIG. 22C, the implant 1300 can be deployed within an aneurysm with a height H3 greater than H1 and H2 in FIGS. 22A and 22B respectively. As seen here, the ball segment 1348*a* can be pushed distally even further into the first portion of the tubular braid 1310 until it is completely enclosed within the sack 1344*a*. By pressing the ball segment 1348*a* into the first portion of the tubular braid 1310 within an aneurysm with a height H3, the first portion 1342*a* of the tubular braid 1310 can be moved towards the distal portion of an aneurysm wall 15. Alternatively, as described in FIG. 22B, pushing the ball segment 1348*a* distally into the first portion of the tubular braid 1310 can push the third segment 1346*a* distally into the aneurysm towards a distal portion of the aneurysm wall 15, independent of distal movement of the outer layer 1342*a* and/or sack 1344*a*. This can extend the height of the implant 1300 to better conform to the height of the aneurysm H3. The ball segment 1348*a* can occlude at least a portion of the aneurysm neck 16. The ball segment 1348*a* can also occlude at least a portion of the proximal inversion 1322*a* to seal the opening created by the proximal inversion 1322*a*. In this way, the implant 1300 can be used to treat implants of varying heights and widths depending on the positioning of the ball segment 1348 relative to the first portion of the braid 1310.

FIG. 23 is a flow diagram for a method 1400 for treating an aneurysm 10. The method 1400 can be utilized to treat aneurysms of varying sizes, heights, and shapes with a single device. Step 1410 positions a first portion of a tubular braided implant, the tubular braided implant having a tubular braid, an open end, and a pinched end, within a sac of the aneurysm such that the first portion circumferentially apposes walls within the sac. The first portion can include one or more inversions, including a distal inversion approximate a distal portion of the aneurysm wall. Step 1420 includes expanding a second portion of the tubular braided implant in connection with the first portion of the tubular braided implant radially to occlude a majority of the neck of the aneurysm. Step 1430 presses the second portion distally into the first portion to provide a radial force against the first portion towards the aneurysm wall approximate the neck of the aneurysm in a plane defining a boundary between the aneurysm and blood vessel branches. Lastly, Step 1440 moves the distal inversion toward a distal portion of the aneurysm wall as a result of pressing the second portion distally into the first portion.

The step 1410 of positioning the first portion of the tubular braided implant can further include positioning the open end of the tubular braided implant to circumferentially appose the aneurysm wall, positioning a proximal inversion in the first portion of the tubular braided implant approximate the neck of an aneurysm; and shaping a first segment of the tubular braid extending between the open end and the proximal inversion to appose an at least a portion of a wall of the aneurysm within the aneurysm's sac.

The step 1420 of expanding the second portion of the tubular braided implant can further include compressing the second portion along a central axis of the tubular braided implant such that the second portion forms a substantially ellipsoidal shape.

The step 1430 of pressing the second portion distally into the first portion can further include apposing at least a part of the first portion with the second portion to provide an outwardly radial force along a central axis of the tubular braided implant from the second portion to the first portion. The step 1430 of pressing the second portion distally can also involve pressing the second portion of the tubular braided implant against the proximal inversion in the first portion of the tubular braided implant until the second portion of the tubular braided implant is at least partially enclosed by the proximal inversion. The step 1430 of pressing the second portion distally can also disrupt the flow of blood into the aneurysm by placing multiple layers of braid approximate the neck of the aneurysm.

The method 1400 can further include shaping the tubular braided implant to a delivery shape with a single layer of braid sized to traverse a lumen of a microcatheter.

FIG. 24 is a flow diagram for a method of forming an occlusive device to treat an aneurysm. The method can include inverting a tubular braid comprising an open end and a pinched end to form a distal inversion (1510); inverting the tubular braid to form a proximal inversion by moving the open end over at least a portion of the braid (1520); shaping a first segment of the tubular braid extending between the open end and the proximal inversion (1530); shaping a second segment of the tubular braid extending between the proximal inversion and the distal inversion (1540); positioning the open end to encircle the second segment (1550); shaping a third segment extending from the distal inversion to the pinched end (1560); positioning the second segment to surround the third segment (1570); shaping a ball segment of the tubular braid extending from the third segment radially outward from a central axis to form a substantially ellipsoid shape and converge at the pinched end (1580); and applying a mold to the ball segment of the tubular braid and treating the ball segment with heat to conform the ball segment to the formed shape, the ball segment movable along a central axis of the tubular braid (1590).

The method 1500 can further include positioning the first segment, second segment, and third segment within an aneurysm, and advancing the ball segment distally into the proximal inversion. This step of advancing the ball segment distally into the proximal inversion can move the distal inversion towards a distal portion of a wall of the aneurysm, which can conform the device to the height of the aneurysm. In this manner, the device can be used to treat aneurysms of varying heights, shapes, and sizes.

The method 1500 can also include apposing the proximal inversion with at least a portion of the ball segment. The method 1500 can further include moving the ball segment to a position at least partially enclosed by the second segment distal to the proximal inversion. The method 1500 can also involve retracting the tubular braid until a desired position is achieved relative to the aneurysm.

In known treatments of wide neck aneurysms, the aneurysm is typically treated by placing embolic coils within the aneurysm sac and placing a stent within the parent blood vessel across the aneurysm neck. The stent is necessary in many cases to inhibit the embolic coils from entering the parent blood vessel. If embolic coils enter the parent blood vessel, the coils can obstruct the vessel and/or clots can form on the coils within the blood vessel and create an obstruction in the parent blood vessel. Braided aneurysm intrasaccular implants can be used to treat wide neck aneurysms without requiring a stent to secure the braided implant at the aneurysm neck. However, to achieve the forces necessarily to anchor braided implants in a wide neck bifurcation, the braid can be stiff and resistant to reshaping to an implanted shape that is significantly different than a predetermined shape. It can therefore be challenging, in some cases, to pack the aneurysm with a sufficient braid density to quickly and effectively induce blood stasis within the aneurysm sac. A braid made too soft can compact in shape and cause the aneurysm to recanalize as the implant is no longer sealing the neck of the aneurysm.

Aspects of the present invention are directed to address the above challenges. In examples presented herein, a tubular braided implant can include a braid that can be delivered as a single layer braid, can invert into itself during deployment to form at least two nested sacks, and can include additional braid material that can fill the innermost sack. The additional braid material can loop or coil like a ribbon and/or invert to form smaller and smaller nested sacks. An aspect of the present invention is to provide a structure that allows a sufficient amount of additional braid material to be placed into the innermost sack such that the aneurysm clots quickly for an effective treatment.

When used herein, the terms "tubular" and "tube" are to be construed broadly and are not limited to a structure that is a right cylinder or strictly circumferential in cross-section or of a uniform cross-section throughout its length. For simplicity, tubular structures are generally illustrated herein as having a substantially right cylindrical structure. However, a tubular structure can have a tapered or curved outer surface without departing from the scope of the present invention.

To meet the competing needs for braid stiffness to achieve secure anchoring within the aneurysm and braid softness to deform the braid to a high packing density within the aneurysm, the braid can be made such that portions of the braid pushed into the aneurysm when the aneurysm has a higher packing density are weaker compared to stiffer portions of the braid that expand to anchor the braid within the aneurysm. Stiffness/flexibility of the braid portions can be controlled by braid angle (e.g. picks per inch), strand diameter, number of strands, material of strands, and/or treatment (e.g. heat treatment) to modify strand material properties, etc. A stiffer portion can have a higher braid angle, a larger strand diameter, more strands, strands comprising a stiffer material, and/or strands treated to have greater stiffness compared to a weaker portion.

Stiffer portions of the braid can be positioned near a distal end of the braid when the braid is being delivered through a catheter so that the stiffer portions of the braid exit the catheter and expand to anchor in the aneurysm before the aneurysm is packed. Stiffer portions of the braid can be shaped in a predetermined shape by heat setting or other means such that when the stiffer portions, they expand toward the predetermined shape. The tendency of the stiffer portions of the braid to expand toward the predetermined shape can create sufficient force against the aneurysm walls to anchor the braid in the aneurysm sac. Weaker portions of the braid can be positioned near the proximal end of the braid when the braid is delivered through the catheter. Portions of the braid which have the most flexibility can be dynamically deformed to loop or nest within the aneurysm, folding within the stiffer, anchoring portions of braid.

In addition, or as a replacement for the braid material that fills the innermost sack, the implant can include an embolic coil that can loop within the innermost sack.

Examples presented herein generally include a braided implant that can secure within an aneurysm sac and occlude a majority of the aneurysm's neck. The implant can include a tubular braid having a stiffer portion and a weaker portion, at least the stiffer portion being set into a predetermined shape, the braid being compressible for delivery through a microcatheter, and the braid being implantable in an implanted position that is based on the geometry of the aneurysm in which the braid is implanted and based at least in part on the predetermined shape.

Figure 25:
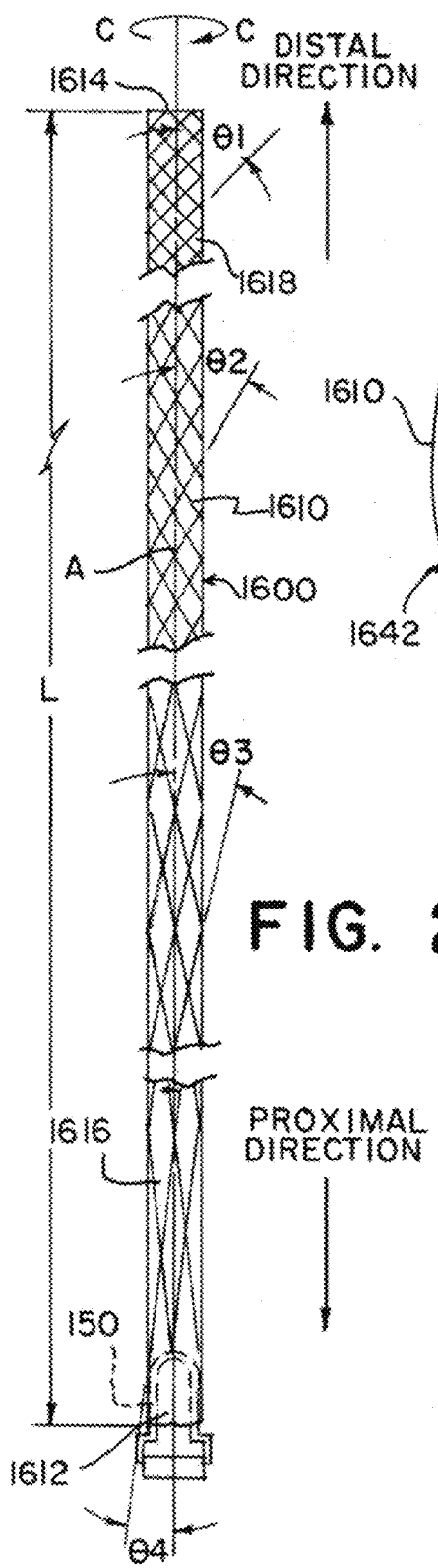
FIG. 25 is an illustration of an implant having a braid shaped for delivery through a catheter according to aspects of the present invention.

An example implant 1600, as illustrated in FIG. 25 can include a braid 1610 that can be shaped into a substantially tubular, single layer shape having a length L measured between each end 1612, 1614 and a variable stiffness along the length L. As illustrated, stiffness can be determined at least in part by braid angle $\theta1$, $\theta2$, $\theta3$, $\theta4$. For ease of discussion, weaker, more flexible portions of braid are illustrated as having a lower braid angle compared to stronger, stiffer portions of the braid; however, weaker and stiffer portions of the braids can differ in strand diameter, number of strands, material of strands, be treated to have differing stiffness/flexibility, and/or by other means as would be appreciated and understood by a person of ordinary skill in the art. Further, example implants comprising braid segments of differing stiffness can include two separate sections joined to form a braid, and the braid need not include the segments of differing stiffness as a contiguous braided tube.

In the single layer tubular shape illustrated in FIG. 25, the braid 1610 can have a circumference C that is substantially uniform along the length L. The tubular shape can have a central axis A extending along the length of the braid 1610. A braid angle $\theta1$, $\theta2$, $\theta3$, $\theta4$ can be measured by comparing the tangential trajectory of a braid strand to the central axis A as illustrated and as would otherwise be understood by a person of ordinary skill in the art according to the teachings herein.

The braid can include a number of strands, for example, from about 4 to about 96 strands, each extending from one braid end 1612 to the other 1614. As used herein, the terms "about" or "approximately" for any numerical values or ranges indicate a suitable dimensional tolerance that allows the part or collection of components to function for its intended purpose as described herein. The strands can wrap helically around the circumference C. The number of strands, angle of strands, diameter of the strands, material of strands, and material properties of strands, can all be factors in controlling material properties of the braid 1610, including porosity and flexibility. Braid strands can be woven such that about half of the strands wrap in a clockwise helix, the other half wraps in a counterclockwise helix, and the oppositely wrapping strands cross over and under each other in an alternating fashion. Constructed as such, portions of the braid having a higher braid angle can therefore having a higher density of strands compared to portions of the braid having lower braid angle. Higher strand density can result in a denser, stiffer braid portion.

The strands can be made from multiple alloys such as a nickel-titanium alloy, cobalt chromium alloys, platinum, nitinol, stainless steel, tantalum, or other alloys, or any other suitable biocompatible materials, or combination of these materials. Also, these materials can be absorbable or non-absorbable by the patient over time. Some or all of braid 1610 can be a multi-filament cylindrical mesh made preferably of nitinol with interwoven platinum filaments for radiopacity or Drawn Filled Tube (DFT) Nitinol with about 10 to about 40% platinum. The apertures in the mesh of braid 1610 can also create a substantially unitary framework or mesh. Thus, the apertures can have variable size, shape, or porosity, and may be uniformly or randomly spaced throughout the wall of the mesh of braid 1610. The apertures can provide the braid 1610 with flexibility and also assist in the transformation of the braid from the collapsed state to the expanded, deployed state, and vice versa.

The braid 1610 as illustrated in FIG. 25 depicts four braid angles $\theta1$, $\theta2$, $\theta3$, $\theta4$ that increase as measured from the proximal end 1612 of the braid 1610 to the distal end 1614 with the braid angle $\theta4$ in the proximal portion 1616 of the braid 1610 being the smallest, the braid angle $\theta3$ in the section immediate distal to the proximal portion 1616 being larger than the braid angle $\theta4$ in the proximal portion 1616, the braid angle $\theta2$ in the next distal section being larger than the angle $\theta3$ in the section immediately proximal to it, and the braid angle $\theta1$ in the distal most section 1618 of the braid 1610 being the largest. As would be appreciated and understood, the braid 1610 can include two or more sections having differing braid angles and thereby differing stiffness/flexibility. The braid can additionally include a continuous gradient change in braid angle and thereby continuous gradient change in stiffness/flexibility from one braid section to another, for instance the braid angle can change continuously from the proximal portion 1616 to the distal portion 1618.

The implant 1600 can be delivered to an aneurysm when the braid 1610 is sized to traverse a catheter. For instance, the braid 1610 can be delivered in the single-layer tubular shape as illustrated in FIG. 25 such that one end of the braid 1614 is a distal end positioned to exit the catheter before the remainder of the braid 1610 and the other end 1612 is a proximal end positioned to exit the catheter after the remainder of the braid 1610. Alternatively, the braid can be delivered in other shapes that include folds, inversions, and/or multiple layers. Regardless of the delivery shape, the braid 1610 can have a distal portion 1618 positioned to exit the catheter before the remainder of the braid 1610 and a proximal portion 1616 positioned to exit the catheter after the remainder of the braid 1610. The distal portion 1618 can have a high braid angle $\theta1$ such that the distal portion 1618 has sufficient stiffness to anchor the braid 1610 within the aneurysm. The proximal portion 1616 can have a low braid angle $\theta4$ such that the proximal portion has sufficient flexibility to collapse into an aneurysm sac containing the remainder of braid 1610. The implant 1600 can further include a detachment feature 150 configured to be detachably attached to an implant delivery system. The detachment feature 150 can be affixed to the braid 1610 at the proximal end 1612 of the braid 1610.

Figure 26:
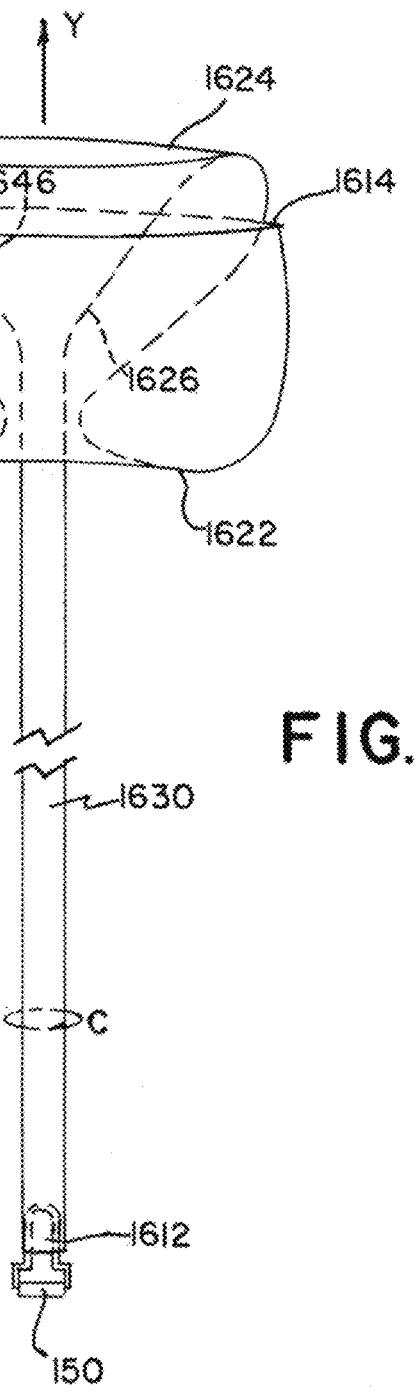
FIG. 26 is an illustration of an implant having a braid in a predetermined shape according to aspects of the present invention.

FIG. 26 illustrates a braid 1610 such as the braid 1610 illustrated in FIG. 25 shaped into a predetermined shape. The braid 1610 can include a memory shape material such as Nitinol, a Nitinol alloy, a polymer memory shape material, or other memory shape material having properties for reshaping as described herein. The braid 1610 can be set to the predetermined shape by heat setting or other means as appreciated and understood by a person of ordinary skill in the art. The braided segment 1610 can be collapsed from the predetermined shape to a deformed shape sized to traverse a microcatheter to an aneurysm. Upon contact with blood when exiting the microcatheter, the braid 1610 can move from the deformed shape toward the predetermined shape. The anatomy of the aneurysm and treatment site can inhibit the braid 1610 from moving to the predetermined shape such that when the braid 1610 is deployed, it can take on a deployed shape that is based in part on the predetermined shape and the shape of the anatomy in which the braid is implanted.

In the predetermined shape, the braid 1610 can include two inversions 1622, 1624 and a pinch point 1626 dividing the braid 1610 into four segments 1642, 1644, 1646, 1630. In the predetermined shape, the braid 1610 can have an outer segment 1642 extending from the open end 1614 of the braid 1610 to a first inversion 1622 of the two inversions 1622, 1624, a middle segment 1644 extending between the two inversions 1622, 1624, an inner segment 1646 extending from a second inversion 1624 of the two inversions 1622, 1624 to the pinched point 1626 of the braid 1610, and an elongated section 1630 extending from the pinch point 1626 to an opposite end 1612 of the braid 1610. When in the predetermined shape, the tubular braid 1610 can be substantially radially symmetrical around a central vertical axis y.

FIG. 26 illustrates a profile of each segment 1642, 1644, 1646, 1630. The detachment feature 150 is illustrated as a flat key that can be used with a mechanical implant delivery system (not illustrated). Example implant delivery systems are described, for instance, in U.S. Patent Application Publication Number 2019/0192162 and U.S. Patent Application Publication Number 2019/0328398 each incorporated herein by reference as if set for in their entireties herein. During delivery and/or positioning of the implant, the key 150 can be visualized radiographically. The key 150 can be released from the delivery system, thereby releasing the implant 1600 from the delivery system. When the implant is released, the key can remain attached to the implant.

The tubular braid 1610 can be formed into the predetermined shape by first pinching the braid 1610 at the pinch point 1626, then inverting the braid outwardly to separate the inner segment 1646 from the middle segment 1644 with an inversion 1624, then shaping the middle segment 1644 over a form to produce the substantially "S" shaped profile illustrated, and finally, inverting the braid 1610 outwardly again to separate the middle segment 1644 from the outer segment 1642 with another inversion 1622. Optionally, the braid can be trimmed at the open end 1614 and/or the proximal end 1612. The open end 1614 can be positioned to encircle the middle segment 1644. The open end 1614 can positioned within the middle third section of the braid's height as illustrated. Alternatively, the open end 1614 can be positioned elsewhere, such as near the distal inversion 1624.

The outer sack 1642 can correspond to the distal portion 1618 of the braid 1610 as illustrated in FIG. 25. The distal portion 1618 can have a substantially uniform braid angle θ1 along its length when the single layer tubular shape illustrated in FIG. 25 The braid 1610 can have an abrupt braid angle change at the proximal inflection 1622. The braid 1610 can have a graduated braid angle change through the middle section 1644 and inner section 1646. The tail 1630 can have a braid angle θ4 that is substantially consistent along the length of the tail 1630. The tail 1630 can correspond to the proximal portion 1616 of the braid 1610 in the single layer tubular shape as illustrated in FIG. 25.

Alternatively, sections 1642, 1644, 1646 distal to the pinch point 1626 can have a high braid angle θ1 that is consistent along the length of those sections 1642, 1644, 1646 when the braid 1610 is in a single layer tubular shape, the tail section 1630 can have a low braid angle θ4 consistent along its length, and the braid 1610 can have an abrupt change in braid angle at the pinch point 1626. The tail 1630 can be sufficiently flexible such that, when manipulated at an intravascular treatment site, it flattens to a ribbon shape and folds onto itself. Alternatively, braid 1610 can include an abrupt braid angle change at the proximal inflection 1622, at the distal inflection 1624, at the pinch point 1626, or any combination thereof.

Strands of the braid 1610 at the open end 1614 can be free, cut ends; or, alternatively, the strands at the open end 1614 be closed, meaning strands within the braid at the open end 1614 are attached to each other by glue, weld, etc. or the strands bend back at the open end 1614. Free cut ends can have an advantage of being easier to manufacture while the closed strand ends can have an advantage of being more atraumatic compared to the cut ends.

FIGS. 27A through 27I illustrate an implant 1600 such as the implant 1600 illustrated in FIGS. 25 and/or 26 being implant in an aneurysm 10 via a catheter 600. The size of the catheter 600 can be selected in consideration of the size, shape, and directionality of the aneurysm or the body lumens the catheter must pass through to get to the treatment site. The catheter 600 can have a total usable length from about 80 centimeters to about 170 centimeters. The catheter 600 can have an inner diameter ID of from about 0.015 to about 0.032 inches. The outer diameter OD can also range in size and may narrow at either its proximal end or distal end. At its proximal end 26, the catheter 600 can be manually operated by the end-user, and at its distal end can be operable, as illustrated, to be positioned at the neck 16 of the aneurysm 10. While the distal end of the catheter 600 can contain the implant 1600, the distal end can be varied in shape and can curve at an angle.

FIG. 27A illustrates the open end 1614 of the braid 1610 expanding within a sac 12 of the aneurysm 10 to contact walls 14 of the aneurysm 10. The section 1642' contacting the aneurysm wall 14 can correspond to the outer 1642 section in the predetermined shape illustrated in FIG. 26 and/or the distal, stiffer portion 1618 of the braid 1610 illustrated in FIG. 25. The implant 1600 can be selected for treatment such that the selected implant 1600 has an outer segment 1642 in the predetermined shape having a circumference greater than the circumference of the aneurysm sac 12, meaning the section 1642' of the braid 1610 contacting the aneurysm wall provides a force against the aneurysm wall 14 as it tends to expand to the predetermined shape. The implanted shape of the outer section 1642' can thereby be smaller in circumference than the predetermined shape of the outer section 1642.

FIG. 27B illustrates the braid 1610 inverting to form a proximal inversion 1622' in the implanted shape. The proximal inversion 1622' can correspond to the proximal inversion 1622 in the predetermined shape.

Figure 27C:
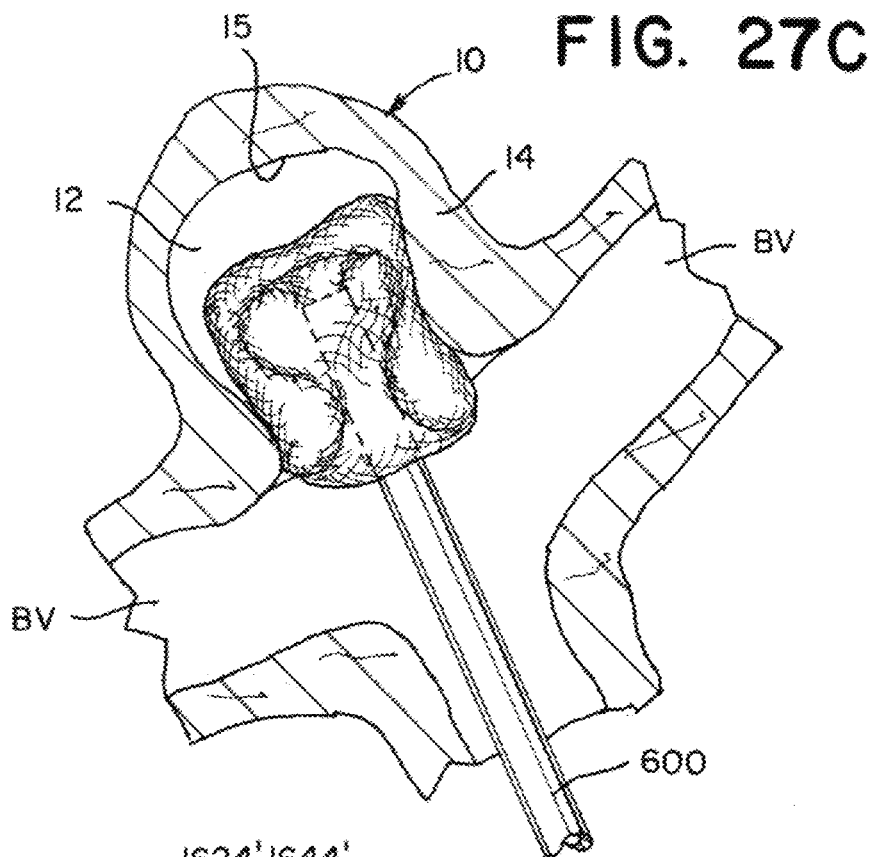

FIG. 27C illustrates the braid 1610 expanding within the outer section 1642'.

Figure 27D:
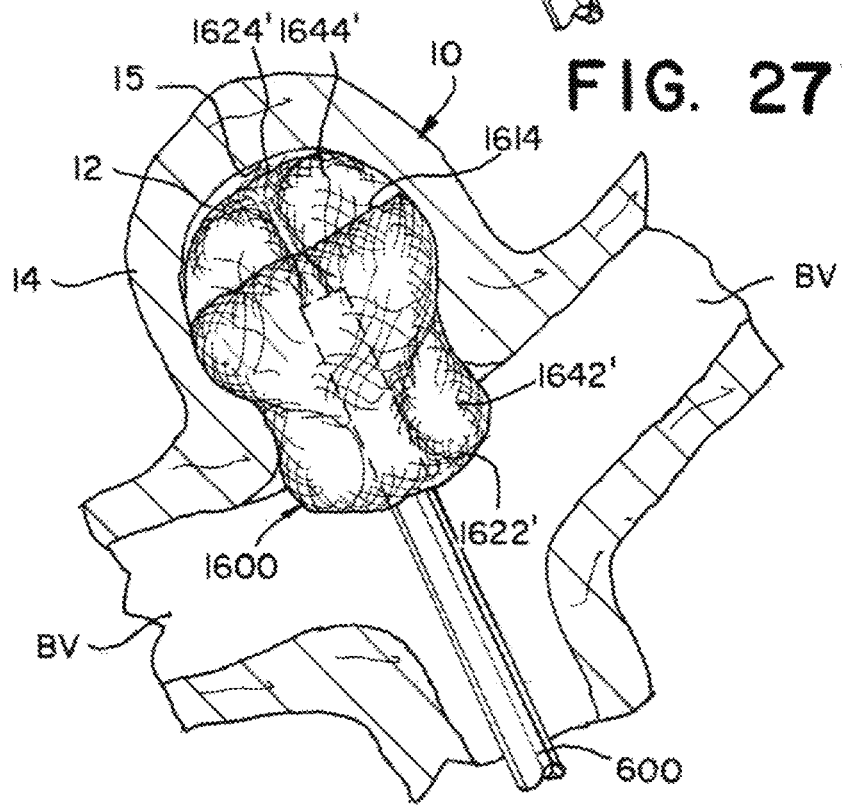

FIG. 27D illustrates the braid forming an inner sack 1644' inside of the outer section 1642'. A distal inversion 1624' is illustrated positioned near a distal portion 15 of the aneurysm wall 14. The distal inversion 1624' can correspond to a distal inversion 1624 of the braid 1610 in the predetermined shape. The inner sack 1644' can correspond to the middle segment 1644 in the predetermined shape illustrated in FIG. 26. The inner sack 1644' can correspond to the stiff, distal portion 1618 of the braid 1610 illustrated in FIG. 25 and/or a portion of the braid 1610 having less stiffness than the distal portion 1618. The inner sack 1644' can correspond to a portion of the braid 1610 having greater stiffness than the flexible proximal portion 1616 illustrated in FIG. 25.

FIG. 27E illustrates a collapsible portion 1646' of the braid 1610 further exiting the catheter 20 and expanding within the inner sack 1614'. The collapsible portion 1646' can correspond to the inner segment 1646 of the braid 1610 in the predetermined shape. The collapsible portion 1646' can correspond to the stiff, distal portion 1618 of the braid 1610 illustrated in FIG. 25 and/or a portion of the braid 1610 having less stiffness than the distal portion. The collapsible portion 1646' can correspond to a portion of the braid 1610 having greater stiffness than the flexible proximal portion 1616 illustrated in FIG. 25.

FIG. 27F illustrates the collapsible portion 1646' forming a dome near the distal inversion 1624'. A pinch point 1626' is illustrated on the proximal side of the dome formed by the collapsible portion 1646'. The pinch point 1626' in the implanted shape can correspond to the pinch point 1626 in the predetermined shape.

FIG. 27G illustrates a proximal tail 1630' of the braid 1610 flattening to a ribbon shape and folding within a space defined by the inner sack 1644' and the dome of the collapsible portion 1646'. The proximal tail 1630' can correspond to the proximal tail 1630 of the braid in the predetermined shape as illustrated in FIG. 26. The proximal tail 1630' can correspond to the flexible, proximal portion 1616 illustrated in FIG. 25.

FIG. 27H illustrates additional length of the proximal tail 1630' folding within the space defined by the inner sack 1644' and the dome of the collapsible portion 1646'.

Figure 27I:
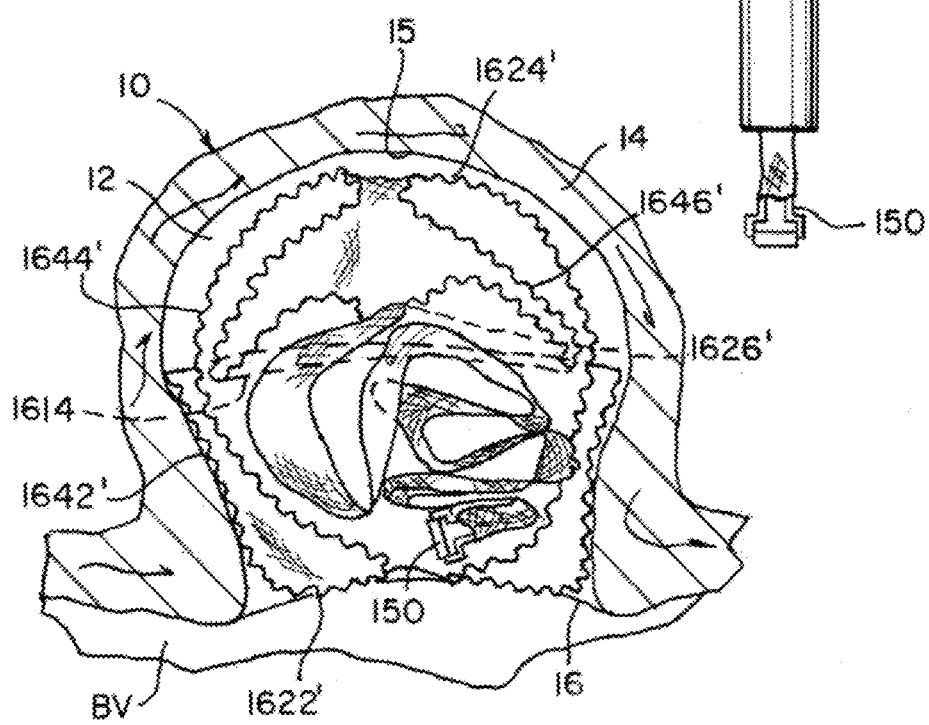

FIG. 27I illustrates the implant 1600 in a final implanted shape. The outer section 1642', inner sack 1644', and collapsible portion 1646' are illustrated in cross-section to better illustrate the folded ribbon shape of the proximal tail 1630'.

Figure 28:
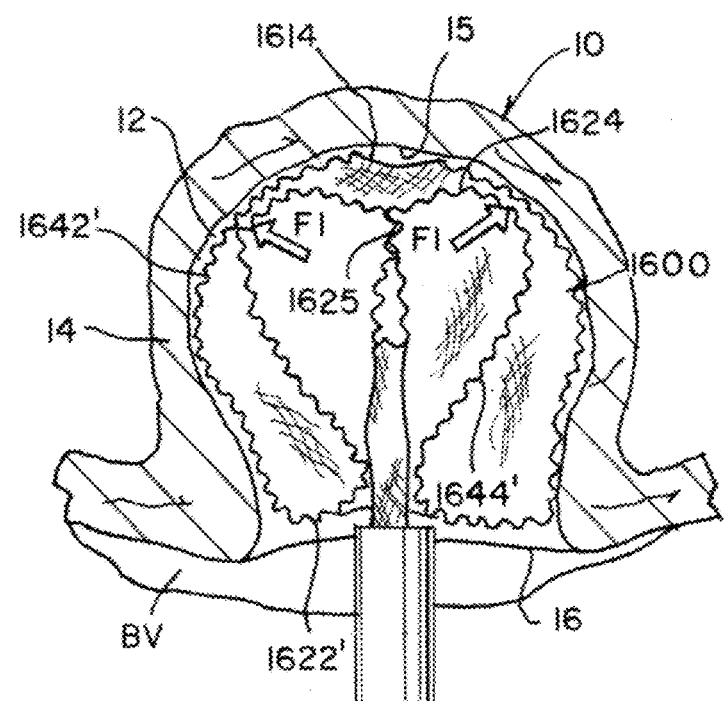
FIG. 28 is an illustration of an implant having a braid twisting near a distal inversion according to aspects of the present invention.

FIG. 28 illustrates an alternative implanted shape of a braid 1610. As illustrated in FIG. 28, the braid 1610 can include a twist 1625 near the distal inversion 1624'. Either with the twist 1625 as illustrated in FIG. 28, or without the twist, as illustrated in FIG. 27I, the inner sack 1644' can provide a force F1 pressing into the aneurysm wall 14 and/or the outer section 1642', depending on the coverage of the outer section 1642'. The outer section 1642' is also illustrated in an alternative configuration such that the open end 1614 is positioned approximate the distal portion 15 of the aneurysm wall 14.

Figure 29A:
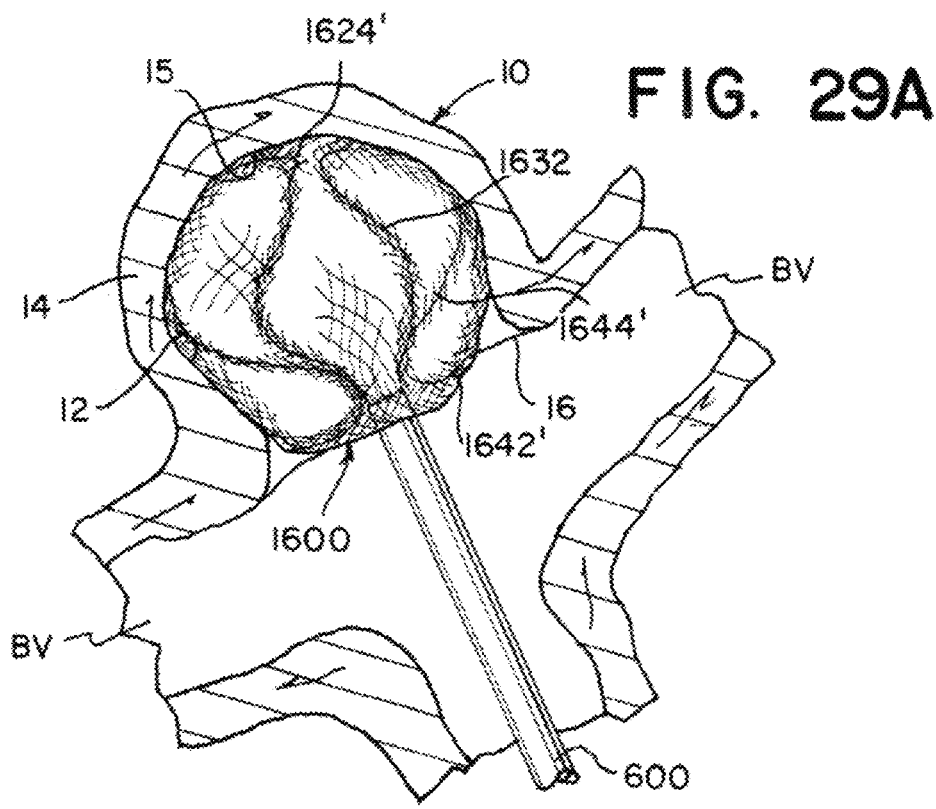
FIGS. 29A through 29B are illustrations of steps of an aneurysm treatment process according to aspects of the present invention.
Figure 29B:
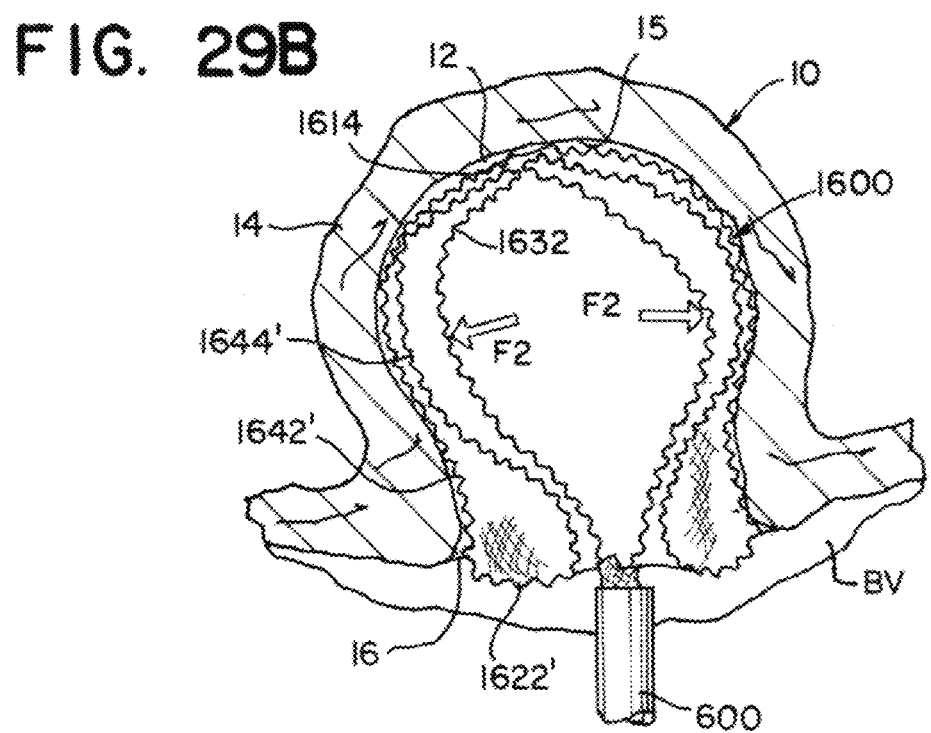

FIGS. 29A and 29B illustrate subsequent implantation steps of the implant 1600 illustrated in FIG. 28. FIG. 29A illustrates a second inner sack 1632 expanding within the aforementioned, first sack 1642'. FIG. 29B illustrates the second inner sack 1632 providing a second force F2 pressing into the first sack 1642'. The braid 1610 is illustrated in cross section in FIG. 29B. In subsequent implantation steps, the braid 1610 can form additional nested sacks. Additionally, or alternatively, the braid can collapse to form a ribbon shape and fold into a space defined by one or more nested sacks similar to as illustrated in FIGS. 27G through 27I.

FIG. 30 illustrates an alternative implant 1600a including a braid 1610 having two sections 1616, 1618 of differing braid angle θ1, θ4, an embolic coil 1660, and a detachment key 150. The embolic coil 1660 can be attached to a proximal end 1612 of the braid 1610. A proximal portion 1616 of the braid 1610 near the proximal end 1612 can have a small braid angle θ4. A distal portion 1618 of the braid 1610 near the distal end 1614 of the braid can have a larger braid angle θ4. The braid 1610 can be shaped into a single layer tubular shape as illustrated in FIG. 30. The braid can be shaped for delivery as described elsewhere herein.

FIG. 31 illustrates an alternative implant 1600a such as the implant 1600a illustrated in FIG. 30 having a braid 1610 in a predetermined shape. The predetermined shape can have four sections 1642, 1644, 1646, 1630, two inversions 1622, 1624, and a pinch point 1626 similar to as described in relation to FIG. 26. The embolic coil 1660 can extend from the tail section 1630 of the braid 1610. When implanted, the embolic coil 1660 can take the place of some or all of the tail portion 1630' of the implant 1600 illustrated in FIG. 27I.

FIG. 32 illustrates an implant 1600a such as the implant 1600a illustrated in FIG. 30 and/or FIG. 31 in an implanted shape. The braid 1610 can have an outer section 1642' and an inner sack 1644' when implanted similar as disclosed in relation to FIG. 27I and/or FIG. 28. The embolic coil 1660 can wind within the inner sack 1644'.

FIG. 33 is a flow diagram outlining example method steps for treating an aneurysm with an implant and/or system such as an example implant 1600, 1600a and/or system described herein, variations thereof, or alternative implant and/or system as would be appreciated and understood by a person ordinary skill in the art.

Referring to method 1700 outlined in FIG. 33, in step 1702 a tubular braid having a stronger section and a weaker section can be selected. The selected tubular braid can include an example tubular braid 1610 as described herein, a variation thereof, or an alternative thereto as would be appreciated and understood by a person of ordinary skill in the art. The stronger section can have a larger braid angle relative to the weaker section such that the strength of the braid sections is respectively determined at least in part by the respective braid angles. Additionally, or alternatively, one or both of the stronger and weaker sections can be treated (e.g. heat treated) to modify material properties of one or both of the sections such that difference in strength between the two sections is determined at least in part by the treatment. Additionally, or alternatively, the stronger section can have a greater number of strands compared to the weaker section such that the strength of the braid sections is respectively determined at least in part by the number of strands. Additionally, or alternatively, the strands in the stronger section can have a larger diameter compared to the diameter of the strands in the weaker section such that the strength of the braid sections is respectively determined at least in part of the diameter of the strands. Additionally, or alternatively, the strands in the stronger section and the weaker section can include differing materials such that the strength of the sections is respectively determined at least in part by the material properties of the strands.

In step 1704, the braid can be delivered through a microcatheter to an aneurysm. The braid can be detachably attached to an elongated delivery system. The implant (and thereby the braid) can be attached to the delivery system at a distal end of the delivery system. The delivery system and the implant can be positioned within the microcatheter such that the delivery system extends from a proximal end of the microcatheter. A user (e.g. physician) can deliver the implant through the microcatheter by manipulating the portion of the delivery system that extends out of the proximal end of the microcatheter. A user can place the implant similar to as illustrated in FIGS. 27A through 27I, FIG. 28, FIGS. 29A through 29B, and/or FIG. 32, otherwise described herein, or as otherwise understood by a person of ordinary skill in the art according to the teachings herein by manipulating the portion of the delivery system extending from the proximal end of the microcatheter.

In step 1706, the distal end of the braid can be positioned at a distal portion 15 of the aneurysm wall 14. The distal end of the braid can be positioned as illustrated in FIG. 28, FIGS. 29A through 29B, and/or FIG. 32. Alternatively, the distal end of the braid can be positioned elsewhere, for instance within a middle third of the aneurysm wall 14, about halfway between the distal portion 15 of the wall 14 and the aneurysm neck 16 as illustrated in FIGS. 27A through 27I.

In step 1708, the stronger section of the braid can be expanded to form an outer sack apposing the aneurysm wall 14. The outer sack can be shaped similar to the outer sack 1642' illustrated in FIG. 28, FIGS. 29A through 29B, and/or FIG. 32. Alternatively, the stronger section of the braid can be expanded to form a bowl shape similar to the outer section 1642' shape illustrated in FIGS. 27A through 27I.

In step 1710, a proximal inversion can be formed in the braid at the aneurysm's neck. The proximal inversion can be positioned similar to the proximal inversion 1622' illustrated in FIGS. 27A through 27I, FIG. 28, FIGS. 29A through 29B, and/or FIG. 32. The proximal inversion can be shaped similar to the proximal inversion 1622' illustrated in FIGS. 27A through 27I, FIG. 28, FIGS. 29A through 29B, and/or FIG. 32. The proximal inversion 1622' can define a boundary between the outer sack or outer section expanded in step 1708 and an inverted portion positioned within the outer sack or outer section.

In step 1712, the inverted portion can be expanded to form a sack inside the outer sack or outer section. The inverted portion can press against the outer sack (or section), thereby pressing the outer sack (or section) into the aneurysm wall 14. The inverted portion can form an inner sack 1644' such as illustrated in FIGS. 27A through 27I, FIG. 28, FIGS. 29A through 29B, and/or FIG. 32.

In step 1714, a distal inversion can be formed in the braid. The distal inversion can define a distal side of the inverted, inner sack expanded in step 1712. The distal inversion can define a boundary between the inner sack and an inner, non-inverted portion of the braid. The inner, non-inverted portion of the braid can include the weaker section of the braid.

In step 1716, the weaker section of the braid can be positioned in the inverted sack. The weaker section can be flattened to a ribbon shape and folded into the inverted sack. The weaker section can be flattened and folded such as illustrated in FIGS. 27G through 27I, as otherwise described herein, and/or as understood by a person of ordinary skill in the art according to the teachings herein. The weaker section can correspond to the tail section 1630, 1630' of the braid 1610.

Figure 34A:
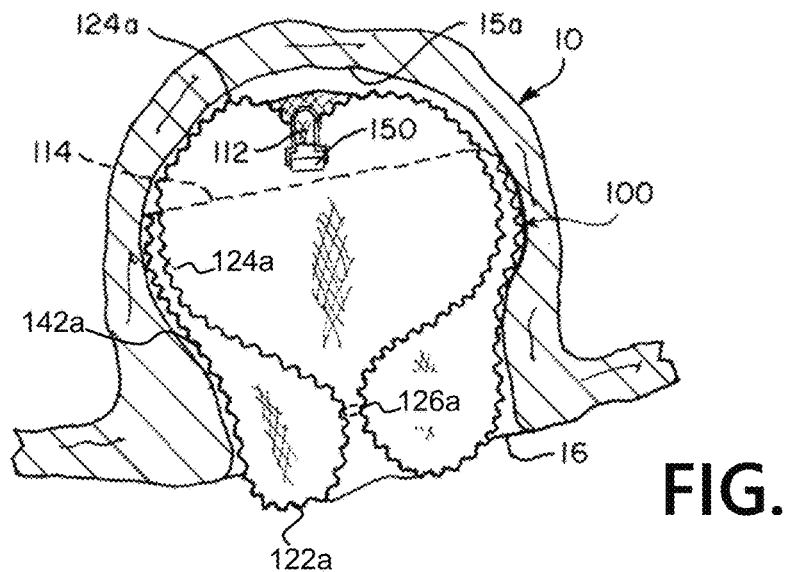
FIGS. 34A through 34D are illustrations of steps of an aneurysm treatment process according to aspects of the present invention.

FIGS. 34A through 34D are illustrations of steps of an aneurysm treatment process. FIG. 34A illustrates an implant 100 being implanted in an aneurysm 10. To achieve the implanted shape illustrated in FIG. 34A, the implant 100 can be implanted similar to as illustrated in FIGS. 3A through 3F or through similar methods for other example implants described herein. As implanted, the braid 110 includes a sack 144a. The braid can be delivered in a delivery configuration having an exterior surface and inverted to form the sack 144a so that the exterior surface of the braid in the delivery configuration corresponds to an interior surface of the sack 144a. The detachment feature 150 is detached so that the implant is positioned within the aneurysm 10 absent interaction with a delivery system or other implant manipulation apparatus. The braid can be allowed to remain self-anchored in the aneurysm 10 in preparation for steps illustrated in FIGS. 34B through 34D.

Figure 34B:
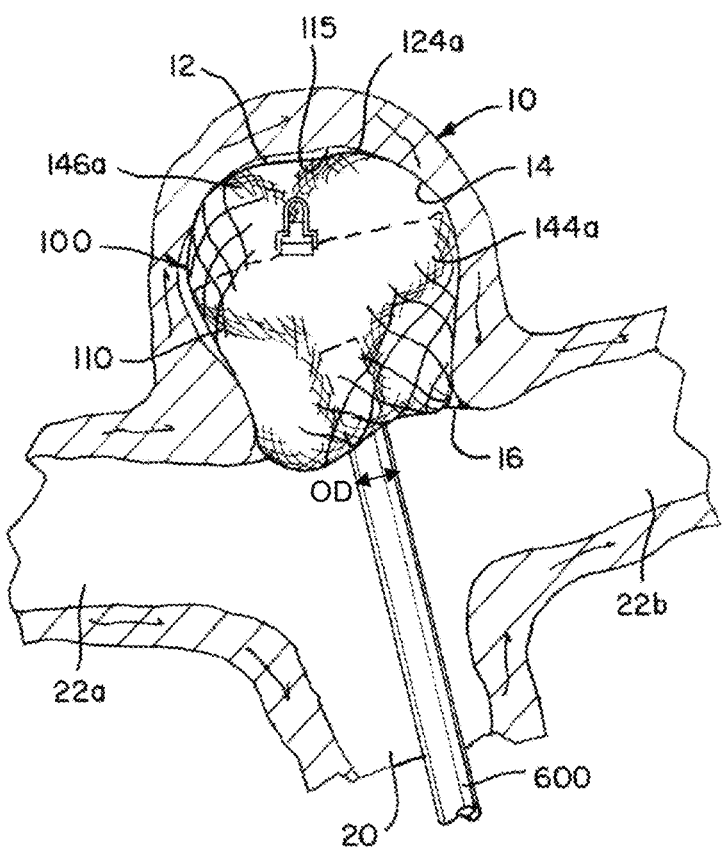

FIG. 34B illustrates a catheter 600 being inserted into a neck opening 126a of the implant 100. The catheter 600 can be the same catheter through which the implant 100 was delivered or a different catheter. The catheter 600 can have an outer diameter (OD) sized to be inserted through the neck opening 126a into the sack 144a of the braid 110. The neck opening 126a can be resilient so that it is capable of expanding to receive the catheter 600 and collapsing to a smaller diameter when the catheter 600 is removed. The braid 110 can include embolic material onto which thrombotic material may accumulate. The catheter 600 is preferably inserted into the neck opening 126a prior to thrombotic material accumulating to inhibit the neck opening 126a from expanding to receive the catheter 600.

Figure 34C:
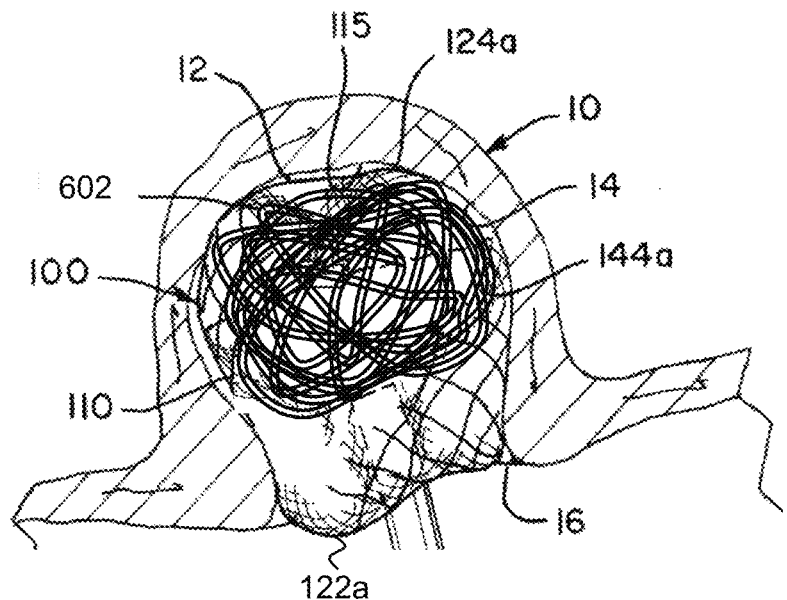

FIG. 34C illustrates embolic coils 602 being inserted into a sack 144a of the braid 110 via the catheter 600. The embolic coils 602 can at least partially fill the sack 144a of the implant 100. The embolic coils 602 can press outwardly to anchor the implant 100 into aneurysm walls 14. The sack 144a and outer layer 142a of the braid 110 can act as a container to inhibit the coils 602 from exiting the aneurysm sac 12. The coils 602 can aid in occluding the aneurysm 10 as there is more embolic material in the aneurysm. The coils 602 can also be used to inhibit compaction of the braid 110. This method can also be used if the aneurysm recanalizes, allowing the physician to place embolic material in areas that did not occlude. Other embolic material can be used in place of the embolic coil 602 such as foam, glue, or biodegradable material to aid in occlusion of the aneurysm 10 and/or resist compaction of the braid 110. In some examples, the braid 110 at the proximal inversion 122a can have a pore size that is sufficiently small to inhibit blood flow near the aneurysm neck 16 where the aneurysm 10 lacks coils 602. In this case, the method of treatment can cease without proceeding to the step illustrated in FIG. 34D.

Figure 34D:
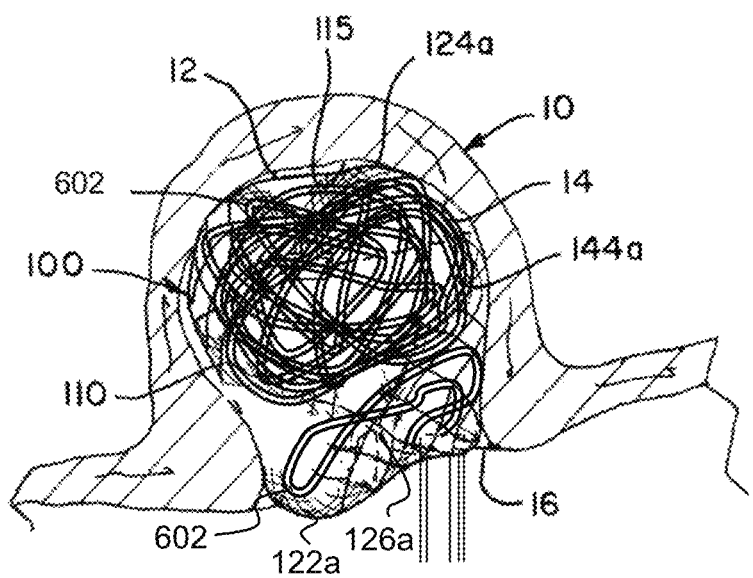

FIG. 34D illustrates the catheter 600 repositioned to extend through openings of the mesh of the braid 110 approximate the aneurysm neck 16, at the proximal inversion 122a of the braid 110. Embolic coils 602 are being inserted between the outer layer 142a and sack 144a. As illustrated, the braid 110, at the proximal inversion 122a, has a pore size approximately equal to the outer diameter OD of the catheter 600 or larger so that the catheter 600 can be inserted through the mesh at the proximal inversion 122a. Generally, a larger pore size can allow the braid 110 to have a smaller diameter during delivery and/or be more flexible compared to some braids having a smaller pore size. The larger pore size can therefore allow the braid 110 to traverse vasculature more easily than a braid having a smaller pore size. When coils 602 are relied upon to arrest blood flow into the aneurysm as illustrated, the braid 110 can be relied on primarily to cage the coils 602 and the ability of the braid 110 itself to arrest blood flow is less consequential.

The porosity of the braid 110 can be uniform or can vary along its length. Variation in pore sized can be accomplished by change in braid angle and/or variation in number of braid strands. For example, in a treatment that ceases at the step illustrated in FIG. 34C, the braid 110 can have small pores in a portion that includes the proximal inversion 122a and nearby braid that is likely to cross the aneurysm neck 16, and larger pores elsewhere. In this example, the braid 110 can be more easily delivered compared to a braid having uniform porosity with smaller sized pores at the proximal inversion 122a, and the small pores at the aneurysm neck 16 can be effective to arrest blood flow into the aneurysm 10. In another example, in a treatment that includes the step illustrated in FIG. 34D, the braid 110 can have large pores in the portion that includes the proximal inversion 122a and nearby braid that is likely to cross the aneurysm neck 16 and smaller pores at least in a portion of the braid including the distal inversion 124a and braid likely to contact the aneurysm wall 14. In this example, when the aneurysm is ruptured, the braid portion having smaller pores at the distal inversion 124a can be effective to clot the rupture and stop bleeding prior to delivery of the coils 602, while the braid portion at the proximal inversion 122a allows packing of coils 602 at the aneurysm neck 16. As another example, in a treatment that ceases at the step illustrated in FIG. 34C, the braid can have small pores at the proximal inversion 122a and the distal inversion 124a and larger pores elsewhere.

Although the implant 100 has a similar implanted shape to that illustrated in FIG. 1B, other implants having an opening into a sack can similarly receive embolic coils 602. The catheter 600 can be navigated around the compaction resistant post 248a, 446a, 846 of the implants 200, 400 illustrated in FIGS. 7B, and 9B to place embolic coils 602 into the respective sacks 244a, 444a and similarly for the implant 800 illustrated in FIG. 14. Embolic coils 602 can be implanted in lobes of the sack 344a, 944a of the implants 300, 900 illustrated in FIGS. 8B, 16A, and 16B. Embolic coils 602 can be implanted in the inner sack 544a of the implant 500 illustrated in FIG. 12C and similarly for the implant 700 illustrated in FIG. 13. The catheter 600 can be navigated around the ball segment 1348a to place embolic coils 602 within the sack 1344a of the implant 1300 illustrated in FIG. 22C. Embolic coils 602 can be added further fill the sack 1644' of implants 1600, 1600a illustrated in FIGS. 27I, 29B, and 32. Embolic coils 602 can be positioned within sacks 1844a, 1944a, 2044a of implants 1800, 1900, 2000 illustrated in FIGS. 35B, 36B, and 37B.

Figure 35A:
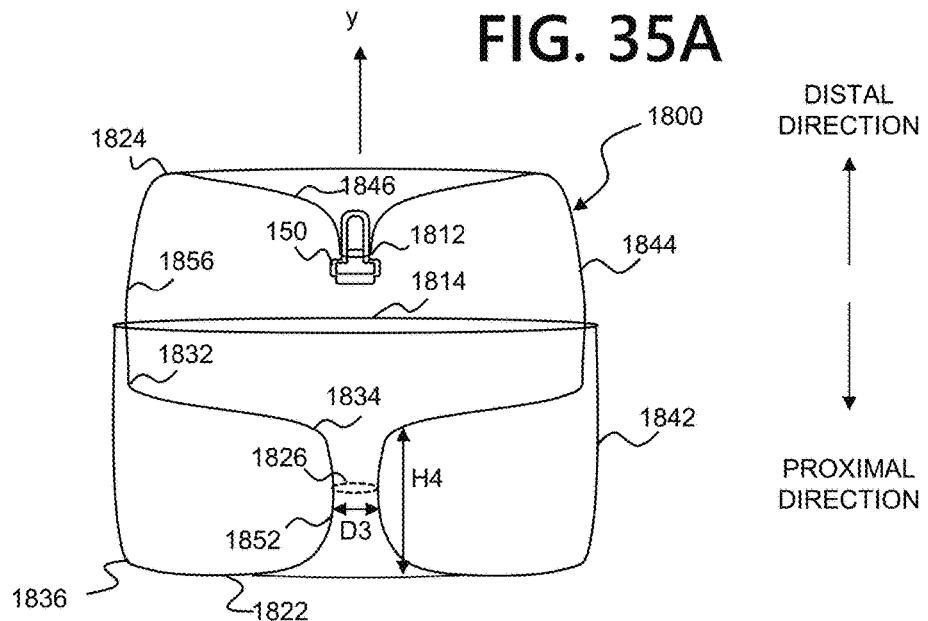
FIG. 35A is an illustration of an example implant having a tubular braid in another alternative predetermined shape according to aspects of the present invention.
Figure 35B:
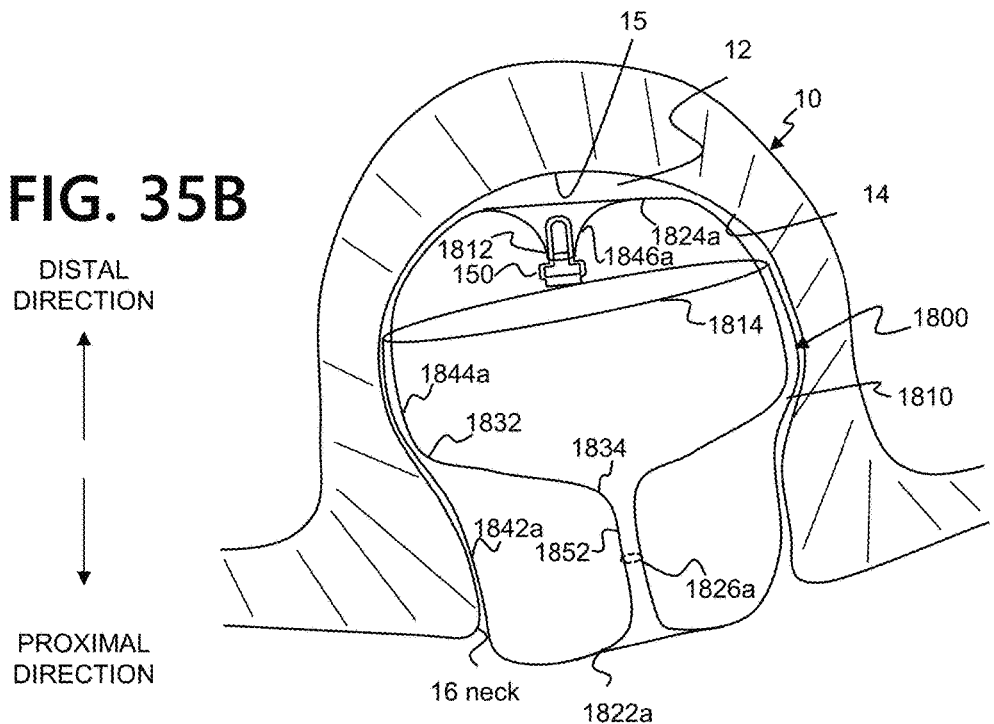
FIGS. 35B and 35C are illustrations of the example implant illustrated in FIG. 35A with the tubular braid in two possible implanted shapes, respectively according to aspects of the present invention.
Figure 35C:
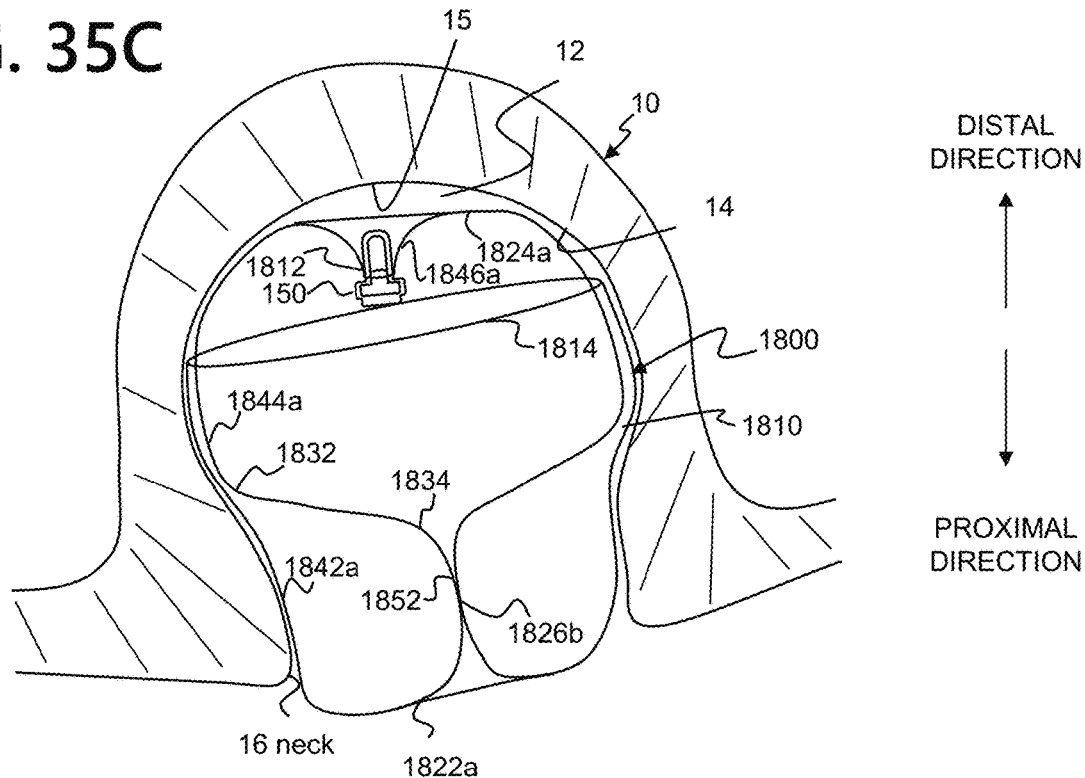
Figure 36A:
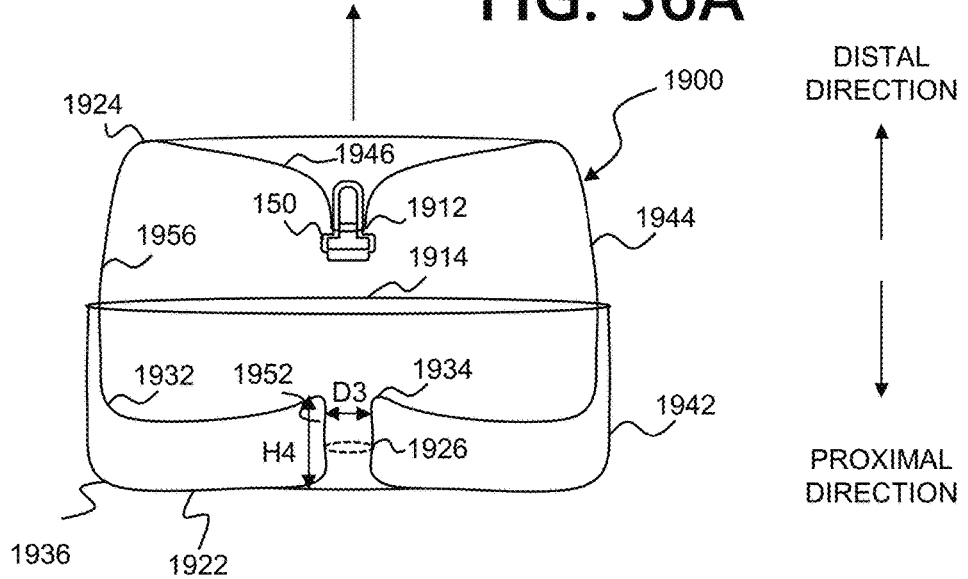
FIG. 36A is an illustration of an example implant having a tubular braid in another alternative predetermined shape according to aspects of the present invention.
Figure 36B:
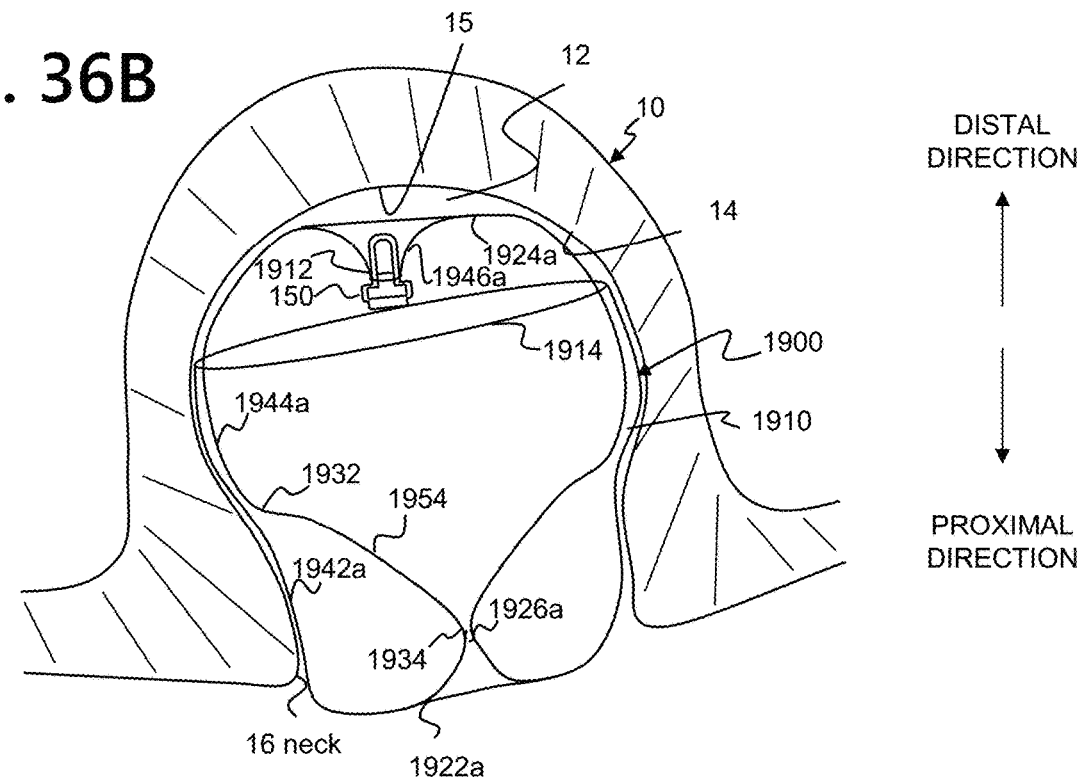
FIGS. 36B and 36C are illustrations of the example implant illustrated in FIG. 36A with the tubular braid in two possible implanted shapes, respectively according to aspects of the present invention.
Figure 36C:
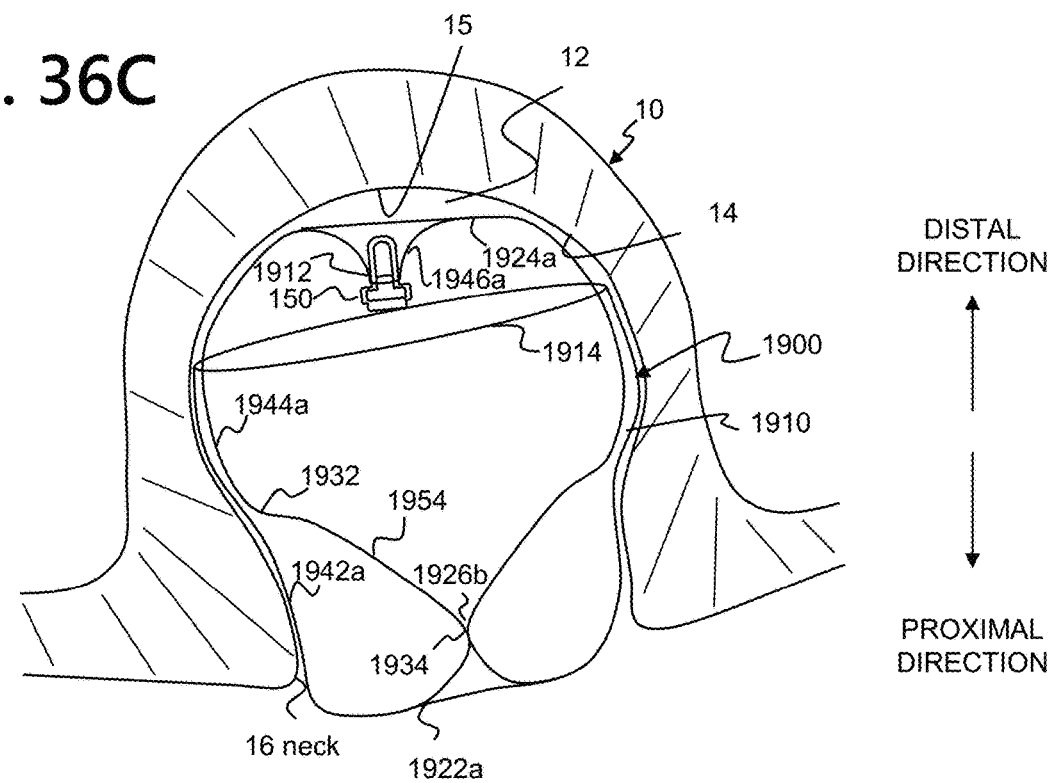
Figure 37A:
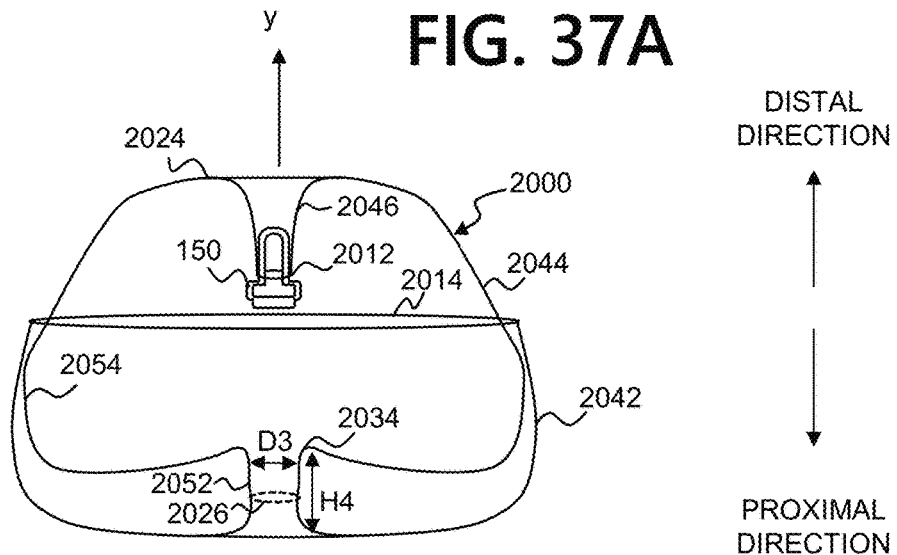
FIG. 37A is an illustration of an example implant having a tubular braid in another alternative predetermined shape according to aspects of the present invention.

FIGS. 35A, 36A, and 37A are each illustrations of a respective implant 1800, 1900, 2000 having another respective alternative predetermined shape. Variations in predetermined shape respectively result in differing implanted shapes as illustrated in FIGS. 35B, 35C, 36B, 36C, 37B and 37C. The implanted shapes illustrated in FIGS. 35C, 36C, and 37C include a twist at each of their respective neck openings 1826b, 1926b, 2026b while the implanted shapes illustrated in FIGS. 35B, 36B, and 37B lack such a twist at their respective neck openings 1826a, 1926a, 2026a. The twist can be incorporated into the shape of the predetermined shape (not illustrated) and/or can be accomplished by manipulating features of the braid such as braid angle or braid wire shape at the neck opening 1826, 1926, 2026.

Similar to the implant 100 illustrated in FIG. 6A, each implant 1800, 1900, 2000 as illustrated in FIGS. 35A, 35B, 36A, 36B, 37A, and 37B can each include a respective tubular braid 1810, 1910, 2010 having an open end 1814, 1914, 2014 and a pinched end 1812, 1912, 2012. Each implant 1800, 1900, 200 can include a detachment feature 150 attached to the braid 1810, 1910, 2010 at the pinched end 1812, 1912, 2012. The tubular braid 1810, 1910, 2010 can be formed in the respective predetermined shape, collapsed for delivery through a microcatheter, attached to a delivery system at the detachment feature 150, and implanted in a shape similar to as illustrated in FIGS. 35B, 35C, 36B, 36C, and 37C respectively.

When in the predetermined shape, the tubular braid 1810, 1910, 2010 of each respective implant 1800, 1900, 2000 can include two inversions 1822, 1824, 1922, 1924, 2022, 2024 dividing the braid 1810, 1910, 2010 into three segments 1842, 1844, 1846, 1942, 1944, 1946, 2042, 2044, 2046. In the predetermined shape, each respective braid 1810, 1910, 2010 can have an outer segment 1842, 1942, 2042 extending from the open end 1814, 1914, 2014 of the braid 1810, 1910, 2010 to one of the inversions 1822, 1922, 2022, an inner segment 1846, 1946, 2046 extending from the pinched end 1812, 1912, 2012 of the respective braid 1810, 1910, 2010 to the other of the inversions 1824, 1924, 2024, and a middle segment 1844, 1944, 2044 extending between the two inversions 1822, 1824, 1922, 1924, 2022, 2024. When in the predetermined shape, each tubular braid 1810, 1910, 2010 can be substantially radially symmetrical about a central vertical axis y. FIGS. 35A, 36A, and 37A each illustrate a profile of each segment 1842, 1844, 1846, 1942, 1944, 1946, 2042, 2044, 2046 for each respective braid 1810, 1910, 2010, and the detachment feature 150 is illustrated as a flat key that can be used with a mechanical implant delivery system (not illustrated).

The tubular braids 1810, 1910, 2010 can be formed into the predetermined shape similar to methods described elsewhere herein. Each tubular braid 1810, 1910, 2010 can include memory shape material that can be heat set to a predetermined shape, can be deformed for delivery through a catheter, and can self-expand to an implanted shape that is based on the predetermined shape and confined by the anatomy of the aneurysm 10 in which it is implanted.

The general dimensions of each implant 1800, 1900, 2000 in the predetermined shape can be described in relation to heights H1, H2, H3 and diameters D1, D2 as illustrated in FIG. 6A. In the implanted shapes illustrated in FIGS. 35B, 36B, and 37B, the aneurysm 10 has a diameter DA that is approximately equal to or smaller than the diameter D1 of the outer segment 1842, 1942, 2042 and the diameter D2 of the middle segment 1844, 1944, 2044 of the braids 1810, 1910, 2010 in their respective predetermined shapes.

Figure 37B:
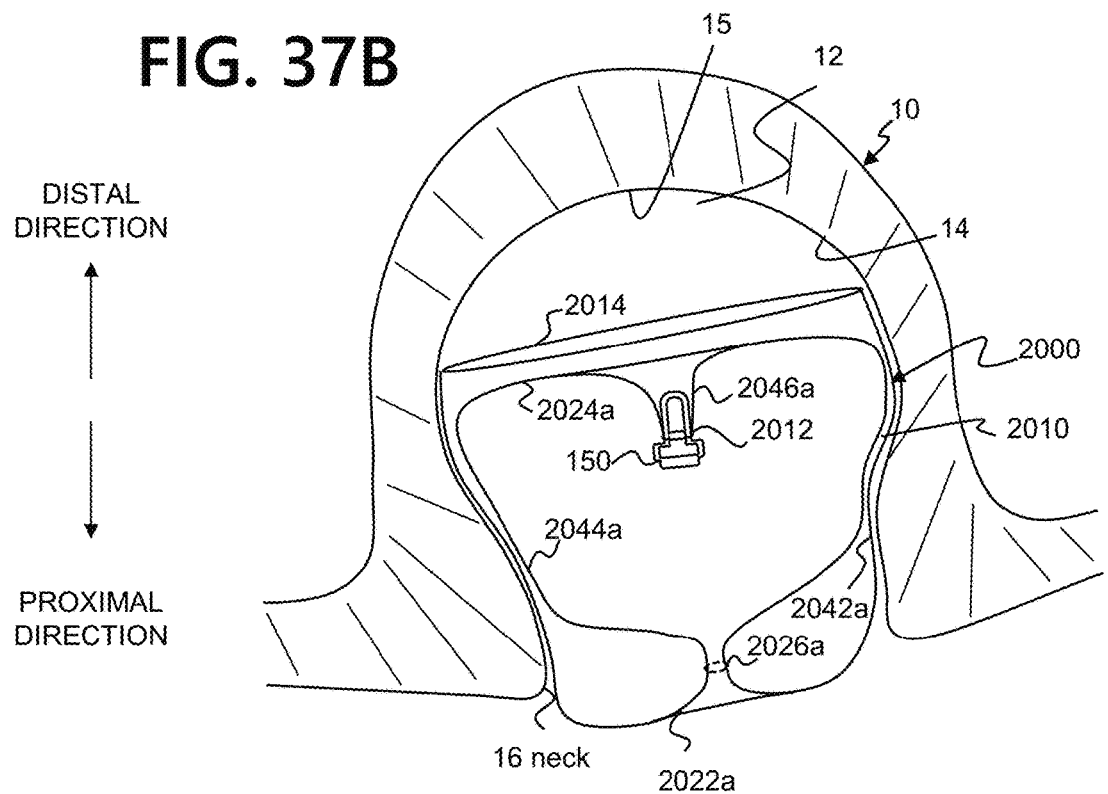
FIGS. 37B and 37C are illustrations of the example implant illustrated in FIG. 37A with the tubular braid two possible implanted shapes, respectively according to aspects of the present invention.
Figure 37C:
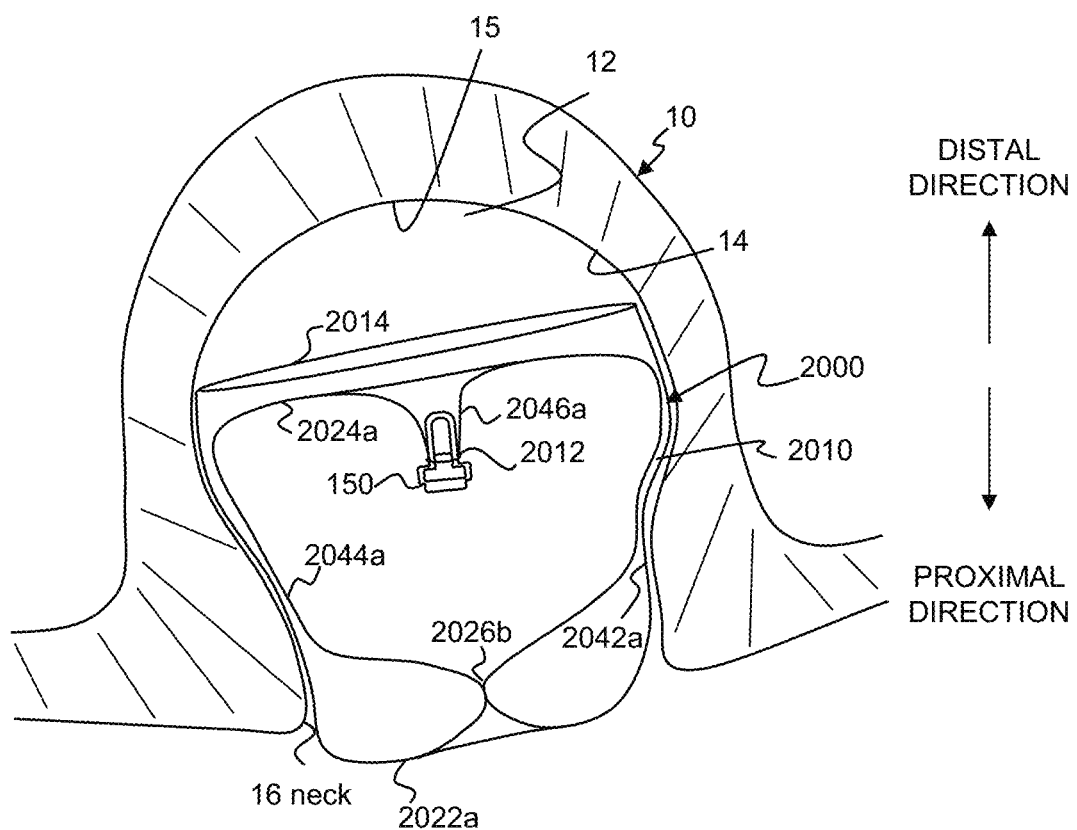

It can be advantageous to minimize a neck opening 1826, 1926, 2026 in the respective braid 1810, 1910, 2010 to maximize occlusion of an aneurysm neck 16 when the respective implant 1800, 1900, 2000 is implanted. Each braid 1810, 1910, 2010 is illustrated as having a tubular neck opening 1826, 1926, 2026 in the predetermined shape having a height H4 and a diameter D3. The neck openings 1826, 1926, 2026 can respectively be configured to constrict when the respective braid 1810, 1910, 2010 is implanted. As illustrated in FIGS. 35B, 36B, and 37B, the neck openings 1826a, 1926a, 2026a are constricted compared to their predetermined shape, and can be pushed open by the catheter 600 so that embolic coils 602 can be implanted in each respective braid sack 1844a, 1944a, 2044a similar to as illustrated in FIG. 34C. The neck openings 1826a, 1926a, 2026a can resiliently collapse once the catheter 600 is removed. As illustrated in FIGS. 35C, 36C, and 37C, the neck openings 1826b, 1926b, 2026b are twisted to further constrict the entrance to each respective braid sack 1844a, 1944a, 2044a. Preferably, the twisted constriction is resistant to opening. In some examples, the twisted neck opening 1826b, 1926b, 2026b can be so resistant to opening that a catheter 600 is not able to pass through the twisted neck opening 1826b, 1926b, 2026b into the braid sack 1844a, 1944a, 2044a. In such examples, where the braid 1810, 1910, 2010 is configured to cage embolic coils 602, the braid 1810, 1910, 2010 can include large pores through which the catheter 600 can be inserted to implant coils in the braid sack 1844a, 1944a, 2044a and/or between the sack 1844a, 1944a, 2044a and outer layer 1842a, 1942a, 2042a.

FIG. 35A illustrates an implant 1800 having a neck opening 1826 with height H4 than is elongated compared to the neck openings 1926, 2026 of the implants 1900, 2000 illustrated in FIGS. 36A and 37A. As a result, a braid segment 1852 surrounding the neck opening 1826 forms an elongated column when implanted as illustrated in FIG. 35B. Because the braid 1810 is embolic, as blood travels through the extended length of the columnar braid segment 1852, the braid segment can become clogged with thrombotic material to thereby promote venous stasis within the aneurysm 10. The middle segment 1844 can include bends 1832, 1834 of approximately 90° to cause a distal section 1856 of the middle segment 1844 to press into the aneurysm walls 14 and to cause the diameter D3 of the neck opening 1826 to collapse to a smaller neck opening 1826a when implanted. The braid 1810 can include an approximately 90° bend approximate the proximal inversion 1822 (in the predetermined shape) to cause the braid 1810 near the proximal inversion 1822a (when implanted) to be substantially parallel to the neck plane 18 (FIG. 6B) and to also cause the diameter D3 of the neck opening 1826 to collapse to a smaller neck opening 1826a when implanted. The implanted shape includes inversions 1822a, 1824a and layers 1842a, 1844a, 1846a respectively corresponding to inversions 1822, 1824 and segments 1842, 1844, 1846 of the predetermined shape.

FIG. 36A illustrates an implant 1900 having a predetermined shape similar to that illustrated in FIG. 35A with an exception that the height H4 of the neck opening 1926 is comparatively foreshortened. The foreshortened height H4 of the neck opening 1926 can cause the diameter D3 of the neck opening 1926a when implanted to be decreased smaller than the diameter of the neck opening 1826a of the implant 1800 illustrated in FIG. 35B, all other factors being equal.

The middle segment 1944 can include bends 1932, 1934 of approximately 90° to cause a distal section 1956 of the middle segment 1944 to press into the aneurysm walls 14 and to cause the diameter D3 of the neck opening 1926 to collapse to a smaller neck opening 1926a when implanted. The braid 1910 can include an approximately 90° bend approximate the proximal inversion 1922 (in the predetermined shape) to cause the braid 1910 near the proximal inversion 1922a (when implanted) to be substantially parallel to the neck plane 18 (FIG. 6B) and to also cause the diameter D3 of the neck opening 1826 to collapse to a smaller neck opening 1826a when implanted. The implanted shape includes inversions 1922a, 1924a and layers 1942a, 1944a, 1946a respectively corresponding to inversions 1922, 1924 and segments 1942, 1944, 1946 of the predetermined shape.

The predetermined shapes illustrated in FIGS. 35A and 36A have an outer profile that approximates a right cylinder. The respective braids 1810, 1910 can respectively have a proximal bend 1836, 1936 of approximately 90° near the proximal inversion 1822, 1922. The respective braids 1810, 1910 are illustrated as having an acute angle near the respective distal inversions 1824, 1924. Alternatively, the respective braids 1810, 1910 can include a distal bend approximately 90° near distal inversions 1824, 1924, shaped similarly to the respective proximal bends 1836, 1936.

FIG. 37A illustrates an implant 2000 having a foreshortened height H4 of the neck opening 2026 similar to that illustrated in FIG. 36A. FIG. 37A illustrates a braid 2010 having a pear or teardrop shaped profile. Alternatively, the braid 2010 can have a profile that approximates a sphere or some shape between the pear as illustrated and a sphere. Compared to the shapes illustrated in FIGS. 35A and 36A, the pear or teardrop shaped profile can provide an increased outward force against aneurysm walls 14 in the proximal portion of the aneurysm sac 12 (i.e. near the neck 16) and decreased outward force in the dome of the aneurysm sac 12 (i.e. near the distal wall 15). Increased outward force in the proximal portion can increase impaction resistance of the implant 2000. Reduced force at the dome can reduce risk of rupturing a fragile dome by the implant 2000.

The middle segment 2044 includes a bend 2034 separating a columnar segment 2052 from a sack-shaped segment 2054. Configured as such, the diameter D3 of the neck opening 2026 can collapse to a smaller neck opening 2026a when implanted. The implanted shape includes inversions 2022a, 2024a and layers 2042a, 2044a, 2046a respectively corresponding to inversions 2022, 2024 and segments 2042, 2044, 2046 of the predetermined shape. The middle layer 2044a can be positioned in closer proximity to the aneurysm neck 16 compared to some of the other example braids illustrated herein, including the implants 100, 1800, 1900 illustrated in FIGS. 1B, 35B, and 36B. Increased density of braid material at the aneurysm neck 16 can further inhibit blood flow into the aneurysm sac 12 and thereby promote venous stasis. The closer proximity of the middle layer 2044a to the aneurysm neck can further allow for the braid 2010 to more easily invert because there is less material that needs to be deployed out of the catheter 600 in order to perform the inversion step to invert the braid 2010 into itself.

Various features of the example implants, systems, and methods illustrated and described herein are combinable as understood by a person skilled in the pertinent art according to teachings herein. Not every combinable feature is expressly illustrated or stated for the sake of brevity.

Implants 100, 200, 300, 400, 500, 700, 800, 900, 1000, 1300, 1600, 1600a, 1800, 1900, 2000 can include a combination of round and flattened wires according to the principles illustrated and described in relation to FIGS. 15A-C and 16A-C.

The tubular braid 110, 210, 310, 410, 510, 560, 710, 760, 810, 860, 910, 1010, 1310, 1610, 1810, 1910, 2010 of the example implants 100, 200, 300, 400, 500, 700, 800, 900, 1000, 1300, 1600, 1600a, 1800, 1900, 2000 can include memory shape material that can be heat set to a predetermined shape, can be deformed for delivery through a catheter, and can self-expand to an implanted shape that is based on the predetermined shape and confined by the anatomy of the aneurysm in which it is implanted. Tubular braid can further include platinum wire strands, markers, or other radiopaque features.

The example implants 100, 200, 300, 400, 500, 700, 800, 900, 1000, 1300, 1600, 1600a, 1800, 1900, 2000 can rely on a radial outward force to anchor the implant within the sac of an aneurysm. To this end, the braid(s) 110, 210, 310, 410, 510, 560, 710, 760, 810, 860, 910, 1010, 1310, 1610, 1810, 1910, 2010 can be shaped to a predetermined shape having a diameter (diameter of outermost braid, radially, for implants having multiple braid layers) that is greater than its height (between distal most layer and proximal most layer for implants having multiple braid layers) so that the braid is radially constricted when implanted in an aneurysm. The ratio of diameter to height of the braid(s) in a respective predetermined shape can be within the range of 2:1 to 1:3 to treat aneurysms of many known sizes and shapes.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%.

The descriptions contained herein are examples of embodiments of the invention and are not intended in any way to limit the scope of the invention. As described herein, the invention contemplates many variations and modifications of the implant, including alternative materials, alternative geometries, alternative detachment features, alternative delivery systems, alternative means for forming a braid into a predetermined shape, alternative treatment methods, alternative number of braid layers, etc. These modifications apparent to those having ordinary skill in the art to which this invention relates are intended to be within the scope of the claims which follow.

What is claimed is:

1. A system comprising:
    a tubular braid comprising an open end, a pinched end, and a predetermined shape in which the braid comprises a first segment extending from the open end to a first inversion, a second segment extending from the first inversion to a second inversion and forming a sack comprising an opening approximate the first inversion, and a third segment surrounded by the second segment and extending from the second inversion to the pinched end;
    a catheter comprising a lumen therethrough, a distal end, and an outer diameter at the distal end being sized to be inserted into the sack through the opening of the sack; and
    an embolic coil detached from the tubular braid and positioned within the lumen and configured to exit the distal end of the catheter,
    wherein the tubular braid is stable in an implanted shape based on the predetermined shape when constricted by a substantially spherical cavity, and
    wherein, in the implanted shape, at least a portion of the first segment is configured to be positioned to contact a cavity wall of the substantially spherical cavity, a proximal inversion corresponding to the first inversion of the predetermined shape is configured to be positioned at an entrance to the substantially spherical cavity, the sack is configured to be positioned within the substantially spherical cavity, the opening of the sack is accessible at the entrance to the substantially spherical cavity, and the opening is configured to receive the distal end of the catheter into the sack and is resilient to expand to receive the distal end of the catheter and twist when the catheter is removed from the opening to thereby inhibit access to the sack via the opening.

2. The system of claim 1, wherein the embolic coil is sized to fit within the sack when the tubular braid is in the implanted shape.

3. The system of claim 1, wherein, in the implanted shape, the braid, approximate the proximal inversion, comprises a pore sized to allow the catheter to pass through the pore so that the distal end of the catheter is positioned between the first segment and the sack.

4. The system of claim 1, wherein, in the predetermined shape, the tubular braid is cylindrically symmetrical about a central axis and the second segment comprises a columnar section extending in a proximal direction from the sack, constricted about the central axis, and defining the opening of the sack.

5. The system of claim 1, wherein an outer profile of the tubular braid in the predetermined shape is approximately a right cylinder.

6. The system of claim 1, wherein an outer profile of the tubular braid in the predetermined shape is approximately pear shaped.

7. A tubular braid of an aneurysm implant, the tubular braid comprising:
    an open end;
    a pinched end;
    a predetermined shape in which the braid comprises a first segment extending from the open end to a first inversion, a second segment extending from the first inversion to the second inversion and forming a sack comprising an opening approximate the first inversion, and a third segment surrounded by the second segment and extending from the second inversion to the pinched end; and
    an implanted shape, based on the predetermined shape, in which the tubular braid is stable when constricted by a substantially spherical cavity, and in which at least a portion of the first segment is configured to be positioned to contact a cavity wall of the substantially spherical cavity, a proximal inversion corresponding to the first inversion of the predetermined shape is configured to be positioned at an entrance to the substantially spherical cavity, the sack is configured to be positioned within the substantially spherical cavity, the opening of the sack is twisted to thereby inhibit access to the sack via the opening.

8. The tubular braid of claim 7, wherein, in the predetermined shape, the tubular braid is cylindrically symmetrical about a central axis and the second segment comprises a columnar section extending in a proximal direction from the sack, constricted about the central axis, and defining the opening of the sack.

9. The tubular braid of claim 8, wherein, in the implanted shape, the columnar section is twisted about the central axis.

* * * * *